US008501719B2

(12) United States Patent  
Gleicher et al.

(10) Patent No.: US 8,501,719 B2
(45) Date of Patent: Aug. 6, 2013

(54) ANDROGEN TREATMENT IN FEMALES

(75) Inventors: Norbert Gleicher, Chicago, IL (US); David H. Barad, Closter, NJ (US); Dwyn V. Harben, Bryn Mawr, PA (US)

(73) Assignee: American Infertility of New York, New York, NY (US)

( * ) Notice: Subject to any disclaimer, the term of this patent is extended or adjusted under 35 U.S.C. 154(b) by 514 days.

(21) Appl. No.: 12/610,215

(22) Filed: Oct. 30, 2009

(65) Prior Publication Data

US 2010/0113407 A1    May 6, 2010

Related U.S. Application Data

(63) Continuation-in-part of application No. 12/575,426, filed on Oct. 7, 2009, and a continuation-in-part of application No. 12/123,877, filed on May 20, 2008, now Pat. No. 8,067,400, and a continuation-in-part of application No. 11/269,310, filed on Nov. 8, 2005, now Pat. No. 7,615,544.

(51) Int. Cl.
*A01N 45/00* (2006.01)
*A61K 31/56* (2006.01)

(52) U.S. Cl.
USPC .......................................... 514/169; 514/177

(58) Field of Classification Search
USPC .................................. 514/169, 177
See application file for complete search history.

(56) References Cited

U.S. PATENT DOCUMENTS

| | | | |
|---|---|---|---|
| 4,670,401 | A | 6/1987 | Cutler et al. |
| 4,931,403 | A | 6/1990 | Cutler et al. |
| 6,221,857 | B1 | 4/2001 | Vandenbergh et al. |
| 6,352,997 | B1 | 3/2002 | Waldstreicher et al. |
| 6,548,087 | B1 | 4/2003 | Kent et al. |
| RE39,920 | E | 11/2007 | Umansky et al. |
| 2006/0141499 | A1 | 6/2006 | Sher et al. |
| 2007/0155710 | A1 | 7/2007 | Gleicher et al. |
| 2007/0178478 | A1 | 8/2007 | Dhallan et al. |
| 2008/0269180 | A1 | 10/2008 | Gleicher et al. |
| 2009/0299645 | A1 | 12/2009 | Colby et al. |
| 2011/0020795 | A1 | 1/2011 | Gleicher et al. |

OTHER PUBLICATIONS

Muttukrishna et al. (The International Journal of Obstetrics and Gynaecology, 2005, vol. 112, p. 1384-1390).*
DHEA: Uses, Side Effects, Interactions and Warnings—WebMD (retrieved online Mar. 12, 2012).*
Damario, M. A., et al. "Dual suppression with oral contraceptives and gonadotrophin releasing-hormone agonists improves in-vitro fertilization outcome in high responder patients." Human Reproduction. 1997, 12, 2359-2365.
Visser, et al. "The applicability of the cumulative embryo score system for embryo selection and quality control in an in-vitro fertilization/embryo transfer programme " Human Reproduction, 1993, 8, p. 1723-1728.
Genazzani, et al. "Oral dehydroepiandrosterone supplementation modulates spontaneous and growth hormone-releasing hormone induced growth hormone and insulin-like growth factor-1 secretion in early and late postmenopausal women" Fertility and Sterility, 2001, 76, pp. 241-248.
Billig H, Furuta I, Hsueh AJ. Estrogens inhibit and androgen enhance ovarian granulose cell apoptosis. Endocrinology 1993;133:2204-12.
"Aging and infertility in women: a committee opinion." Fertility and Sterility, 2002; 78: 215-9.
Navot D, Bergh PA, Williams MA, et al. "Poor oocyte quality rather than implantation failure as a cause of age-related decline in female fertility." Lancet, 1991; 337 (8754): 1375-7.
Scott RT, Leonardi MR, Hofmann GE, Illions EH, Neal GS, Navot D. "A prospective evaluation of clomiphene citrate challenge test screening of the general infertility population." Obstet Gynecol, 1993; 82 (4 Pt 1): 539-44.
Scott RT, Jr., "Evaluation and treatment of low responders." Semin Reprod Endocrinol, 1996; 14(4): 317-37.
Scott RT, Jr., Hofmann, GE. "Prognostic assessment of ovarian reserve." Fertility and Sterility, 1995; 63(1): 1-11.
Ziebe S, Loft A, Peterson JH, et al. "Embryo quality and developmental potential is compromised by age." Acta Obstet Gynecol Scand, 2001; 80(2): 169-74.
Terriou P., Sapin C., Giorgetti C., Hans E., Spach JL, Rouller R. "Embryo score is a better predictor of pregananacy than the number of transferred embryos or female age." Fertility and Sterility, 2001; 75(3): 525-31.
Karande V., Morris R., Rinehart J., Miller C., Rao R., Gleicher N. "Limited success using the "flare" protocol in poor responders in cycles with low basal follicle-stimulating hormone levels during in vitro fertilization." Fertility and Sterility, 1997; 67(5): 900-3.
Schoolcraft W., Schienker T., Gee M., Stevens J., Wagley L. "Improved controlled ovarian hyper stimulation in poor responder in vitro fertilization patients with a microdose follicle-stimulating hormone flare, growth hormone protocol." Fertility and Sterility, 1997; 67(1): 93-7.
Toner JP, Flood JT. "Fertility after the age of 40." Obstet Gynecol Clin North Am, 1993; 20(2): 261-72.
Barad D GN. "Increased Oocyte Production after treatment with dehydroepiandrosterone." Fertility and Sterility, 2005;84: 756, e.1-756. (in press).

(Continued)

*Primary Examiner* — Mina Haghighatian
*Assistant Examiner* — Helen Chui
(74) *Attorney, Agent, or Firm* — David W. Denenberg; Davidoff Hutcher & Citron LLP

(57) ABSTRACT

The present invention is directed to a method of using dehydroepiandrosterone (DHEA) to treat a human female with diminished ovarian reserve. The method includes measuring a baseline follicle stimulating hormone (FSH) level of the human female, and when the baseline FSH level is below about 40.0 mIU/ml, administering about 75 milligrams of DHEA per day to the female for at least four months to treat ovarian follicles in at least one ovary of the female to improve human folliculogenesis during the at least four months. The present invention further is directed to a method of restoring the ovarian environment of an older human female to that of a younger human female. The method includes administering about 75 milligrams of DHEA per day to the female for at least four months.

7 Claims, 22 Drawing Sheets

OTHER PUBLICATIONS

Steer CV, Mills CL, Tan SL, Campbell S, Edwards RG. "The cumulative embryo score: a predictive embryo scoring technique to select the optimal number of embryos to transfer in an in-vitro fertilization and embryo transfer program." Human Reproduction, 1992; 7(1): 147-9.

Van Wagenen G, Simpson M. Embryology of the ovary and testis, *Homo sapiens* and Macaca mulatto. New Haven: Yale University Press: 1965.

Block E., "A quantitative morphological investigations of the follicular system in newborn female infants." Acta Anat (Basel), 1953; 17: 201-6.

Forabosco A, Sforza C, De Pol A, Vizzotto L, Marzona L, Ferrario VF. "Morphometric study of the human neonatal ovary." Anat Rec, 1991; 231(2): 201-8.

Gougeon A., "Dynamic of follicular growth in the human: a model from preliminary results." Human Reproduction, 1986; 1(2): 81-7.

Richards JS, Russell DL, RObker RL, DAjee M, Allliston TN. "Molecular mechanisms of ovulation and luteinization." Mol Cell Endocrinol 1998; 145(1-2): 47-54.

McGee EA, Hsueh AJW. "Initial and Cyclic Recruitment of Ovarian Follicles." Endocr Rev, 2002; 21(2): 200-14.

Hsueh AJ, Billig H, Tsafriri A. "Ovarian follicle atresia: a hormonally controlled apoptotic process." Endocr Rev, 1994; 15(6): 707-24.

Kalpia A, Hsueh AJ. "Regulation of ovarian follicle atresia." Annu Rev Physlol, 1997; 59: 349-63.

Robker RL, Richards JS. "Hormonal control of the cell cycle in ovarian cells: Proliferation versus differentiation." Biol Reprod, 1998; 59(3): 476-82.

Harlow C., Shaw H., Hiller S., Hodges J. "Factors influencing follicle-stimulating hormone-responsive steroid genesis in marmoset granulosa cells: Effects of androgens and the stage of a follicular maturity." Endocrinology, 1988; 122: 2780-7.

Dorrington JH, Moon YS, Armstrong DT. "Estradiol 17 [beta] biosynthesis in cultured granulosa cells from hypohysectomized immature rats; stimulation by follicle stimulating hormone." Endocrinology, 1975; 97(5): 1328-31.

Hillier SG, Whitelaw PF, Smyth CD. "Follicular oestrogen synthesis: The two-cell, two-gonadotrophin' model revisited." Molecular and Cellular Endocrinology, 1994; 100(1-2): 51-4.

Bonser J., Walker J., Purohit A., et al. "Human granulosa cells are a site of sulphatase activity and are able to utilize dehydroepiandrosterone sulphate as a precursor for oestradiol production." J Endorinol, 2000; 167(3): 465-71.

Ware VC. The role of androgens in follicular development in the ovary. I. A quantitative analysis of oocytes ovulation. J Exp Zool 1982;222:155-67.

Hillier SG. "Sex steroid metabolism and follicular development in the ovary." Oxford Reviews of Reproductive Biology, 1985; 7: 168-222.

Daniel Saj, Amstrong DT., "Androgens in the ovarian microenvironment." Seminars in Reproductive Endocrinology, 1986; 4(2): 89-100.

Gore-Langton R., Amstrong, D. "Follicular steroid genesis and its control. In: Knobil E, Neill J, eds." The Physiology of Reproduction, New York: Raven Press, 1988: 331-85.

Yan Z, Lee GY., Anderson E. Influence of dehydroepiandrosterone on the expression of insulin-like growth factor-1 during cystogenesis in polycystic rat ovaries and in cultured rat granulosa cells. Biol Reprod, 1997; 57(6): 1509-16.

Wang H., Andoh K., Hagiwara H., et al. "Effect of Adrenal and Ovarian Androgens on Type 4 Follicles Unresponsice to FSH in immature mice." Endocrinology, 2001; 142(11): 4930-6.

Hu Yoc, Wang P-H, Yeh S, et al. "Subfertility and defective folliculogenesis in female mice lacking androgen receptor." PNAS 2004; 101(31): 11209-14.

Tetsuka M., Miller SG. "Differential regulation of aromatase and androgen receptor in granulose cells." J Steroid Biochem Mol Biol, 1997; 61(3-6): 233-9.

Hickey TE, Marrocco DL, Gitchrist RB, Norman RJ, Armstrong DT. "Interactions between androgen and growth factors in granulosa cell subtypes of porcine antral follicles." Biol Reprod, 2004; 7(1): 45-52.

Harlow CR, Hillier SG, Hodges JK. "Androgen modulation of follicle-stimulation hormone-induces granulose cell steroid genesis in the primate ovary." Endocrinology, 1986; 119(3): 1403-5.

Vendola K., Zhou J., Wang J., Famuyiwa OA, Bievre M., Bondy CA. "Androgens promote oocyte insulin-like growth factor I expression and initiation of follicle development in primate ovary." Biol Reprod, 1999; 61(2): 353-7.

Horie K., Takakura K., Fujiwara H., Liao S., Mori T. "Immunohistochemical localization of androgen receptor in the human ovary throughout the menstrual cycle in relation to oestrogen and progesterone receptor expression." Human Reproduction, 1992; 7(2): 184-90.

Barbieri RL, Stuss PM, Powers RD., et al. "Association of body mass index, age, and cigarette smoking with serum testosterone levels in cycling women undergoing in vitro fertilization." Fertility and Sterility, 2005; 83(2): 302-8.

Mitwally MF, Casper RF. "Aromoatase inhibition improves ovarian response to folliclestimulating hormone in poor responders." Fertility and Sterility, 2002; 77(4); 776-80.

MacDougall M., Tan S., Balen A., Jacobs H. "A controlled studies, comparing patients with and without polycystic ovaries undergoing in-vitro fertilization." Hum Reprod, 1993; 8(2): 233-7.

Maciel Gar, Baracat EC, Benda JA, et al. "Stockpiling of transitional and classic primary follicles in ovaries of women with polycystic ovary syndrome." J Clin Endocrinol Metab, 2004; 89(11): 5321-7.

Amirikia H., Savoy-Moore RT, Sundareson AS, Moghissi, KS. "The effects of longterm androgen treatment on the ovary." Fertility and Sterility, 1986; 45(2): 202-8.

Van der Westhuizen S., van der Spuy ZM. "Ovarian morphology as a predictor or hormonal values in polycystic ovary syndrome." Ultrasound Obstet Gynecol. 1996; 7(5): 335-41.

Pache TD, Chadha S., Gooren LJ, et al. "Ovarian morphology in long-term androgentreated female to male transsexuals. A human model for the study of polycystic ovarian syndrome?" Histopathology, 1991; 19(5): 445-52.

Kroboth PD, Salek FS, Pittenger AL, Fabien TJ, Frye RF. "DHEA and DHEA-S: a review." J Cliin Pharmoacol, 1999; 39(4): 327-48.

Kaaks R., Berrino F., Key T., et al. "Serum sex steroids in premenopausal women and breast cancer risk within the European prospective investigation into cancer and nutrition (EPIC)." J Natl Cancer Inst, 2005; 97(10): 755-65.

International Searching Authority—European Patent Office (ISA/EP), International Search Report for PCT International Patent Application PCT/US2010/051776, Date of Mailing Feb. 9, 2011; 4 pages.

Database Medline, US National Library of Medicine, Bethesda, MD; Aug. 2009; "Dehydroepiandrosterone supplementation in assisted reproduction: rationale and results", XP002618305; 2 pages.

Gleicher et al.; Database Medline, US National Library of Medicine, Bethesda, MD; Sep. 2010; "Improvement in diminished ovarian reserve after dehydroepiandrosterone supplementation", XP002618306; 2 pages.

Gleicher et al; "Supplementation with dehydroepiandrosterone (DHEA) improves ovarian reserve, as reflected by anti-mullerian hormone levels", Fertility and Sterility, Elsevier Science vol. 92, No. 3 Sep. 1, 2009, pp. S54-S55.

Gleicher et al; "Improvement in diminished ovarian reserve after dehydroepiandrosterone supplementation", Reproductive Biomedicine Online, Reproductive Healthcare Ltd., GB, vol. 21, No. 3, Sep. 1, 2010; pp. 360-365.

Oostra et al. FMR1: A gene with three faces Biochimica et Biophysica Acta 1790 (2009) 467-477.

Dobrovic et al. DNA methylation, epimutations and cancer predisposition The International Journal of Biochemistry & Cell Biology 41 (2009) 34-39.

International Search Report and Written Opinion of the International Search Authority of International App. No. PCT/US2012/026587.

International Search Report and Written Opinion of the International Search Authority of International App. No. PCT/US2010/051776.

Database Medline [Online] US National Library of Medicine (NLM), Bethesda, MD, US; Aug. 2009, Mamas Leonidas et al: "Dehydroepiandrosterone supplementation in assisted reproduction: rationale and results:", XP002618305, Database accession No. NLM19610174 abstract & Current Opinion in Obstetrics & Gynecology Aug. 2009 LNKD-PUBMED:19610174, vol. 21, No. 4, Aug. 2009, pp. 306-308, ISSN: 1473-656X.
Gleicher N et al: "Supplementation with dehydroepiandrosterone (DHEA) improves ovarian reserve, as reflected by anti-mullerian hormone levels", Fertility and Sterility, Elsevier Science Inc, New York, NY, USA, vol. 92, No. 3, Sep. 1, 2009, pp. S54-S55, XP026543000, ISSN: 0015-0282, DOI: DOI: 10.1016/J. Fertnstert .2009.07.212 [retrieved on Aug. 28, 2009] abstract.
Database Medline [Online] US National Library of Medicine (NLM), Bethesda, MD, US; Sep. 2010, Gleicher N et al: "Improvement in diminished ovarian reserve after dehydroepiandrosterone supplementation." XP002618306, Database accession No. NLM20638339 abstract & Reproductive Biomedicine Online Sep. 2010 LNKD-PUBMED: 20638339, vol. 21, No. 3, Sep. 2010, pp. 360-365 ISSN: 1472-6491.
Gleicher N et al: "Improvement in dimished ovarian reserve after dehydroepiandrosterone supplementation." Reproductive Biomedicine Online, Reproductive Biomedicine Online, Reproductive Healthcare Ltd, GB, vol. 21, No. 3, Sep. 1, 2010, pp. 360-365 XP027238027, ISSN: 1472-6483 [retrieved on Aug. 25, 2010] abstract, fig. 2, p. 362, right column, paragraph 2, p. 364, right column, last para of text.
McClamrock HD, Adashi EY. "Gestational hyperandrogenism." Fertility and Sterility, 1992; 57(2): 257-74.
Sir-Petermann T., Maiqueo M., Angel B., Lara HE, Perez-Bravo F., Recabarren SE. "Maternal serum androgens in pregnant women with poycystic ovarian syndrome: possible implications in prenatal androgenization." Hum Reprod, 2002; 17(10): 2573-9.
Norbert Gleicher MD, David Barad MD MS Barad D, Gleicher N (2005) "Further Evidence that Dehydroepaindrosterone (DHEA) Substitution Improves Ovarian Function: Is 17, 20 Desmofase Deficiency the cause of premature ovarian aging?" "Increased oocyte production after treatment with dehydroepiandrosterone." Fertility and Sterility, In Press, (Included in Paper 1, #14 above).
Barad D, Gleicher N., (2005a) dehydroepiandrosterone (DHEA) adjuvant treatment of ovulation induction for in vitro fertilizations and embryo quality. Human Reproduction.
Consortium, Autoimmune Polyendocrinopathy—Cansasiasis—Ectodermal Dystrophy, (1997). An immune disease, APECED, caused by mutations in a novel gene featuring two PHP-type zinc-finger domains. Nat Genet, 17:399-405.
Garcia-Velasco JA, Moreno L, Pacheco A, Guillen A, Duque L, Requena A, Pellicer A. "The aromatase inhibitor letrozole increases the concentration of intraovarian androgens and improves in-vitro fertilization outcome in low responder patients: a pilot study" Fertility and Sterility, 2005; 84: 82-7.
Gleicher N., Barad D, Race based fertility therapy. "Ovarian Aging: Is there a norm?" Contemp Ob/Gyn, 2005; 50: 65-75. (Submitted for publication).
Grainer DA, Seifer DB, Frazier LM, Tjaden BL, Merril JC. "Racial disparity in clinical outcomes from women using advanced reproductive technology (ART): Analysis of 80, 196ART cycles from the SART database 1900 and 2000." Fertility and Sterility, 2004; 28/S-2: 0-93.
Purcell KJ, Schembi M, Shen S, Croughman M., Fujimoto VY. "Asian ethnicity is associated with reduced pregnancy outcome with in vitro fertilization." Fertility and Sterility, 2004; 28:2 2: 0-98.
Speroff L, Glass RH, Kase NG, "Postmenopausal hormone therapy." In Clinical Gynecology Endocrinology and Infertility, 1999. 6th ed.; Lippincott Williams & Wilkins, pp. 725-799.
Speroff L, Glass RH, Kase NG, "Normal and abnormal sexual development." Idem 1999a :pp. 339-379.
Speroff L., Glass RH, Kase NG. "Amenorrhea" Idem 1999b: pp. 421-485.
Winquivist O, enre-Medhin G, Fustafsson J, Ritzen EM, Lundkvist O, Karlson FA, Kampe O. "Identification of main gonadal autoantigens in patients with adrenal insufficiency associated ovarian failure." J Clin Endocrinol Metab, 1995; 80: 1717-23.
Lutz et al. PNAS, 2001; 98: 13728-13733.
Hammes S.R. Molecular Endocrinology, "Steroids and oocyte maturation—a new look at an old story," 2004; 18(4): 769-775 (minireview).
Morales et al. Journal of Clincal Endocrinology and Metabolism, "Effects of replacement dose of dehydroepiandrosterone in men and women of advancing age" 1994; 78: 1360-1368.
Muasher S.J. "Treatment of Low Responders," Journal of Assisted Reproduction and Genetics, 1993; 10: 112-114.
Lewin et al. Journal of Assisted Reproduction and Genetics, 1994; 11: 357-373 (review).
Barad et al. "Dehydroepiandrosterone (DHEA) Pre-Treatment and Ovulation Induction for In-Vitro Fertilization among Women with a History of Decreased Ovarian Reserve" Fertility and Sterility, 2005; 84: Suppl. 1, S42 (Abstract).
Hugues J.N. "Current Practices and Controversies in Assisted reproduction: Meeting report Medical, Ethnic, and Social Aspects of Assisted Reproduction" World Health Organization, 2001; Sep. 17-21, pp. 102-125.
Weering et al. Human Reproduction, 2001; 16: 1537-1538 (Letters to the Editor).
Gougeou A. Dynamics of human follicular growth: morphologic, dynamic and functional aspects. In Leung PKC, Adashi EY eds; The Ovary; 2nd ed.; Elsevier Academic Press, San Diego, CA, 2004; pp. 25-43.
Fraisse T, Ibecheole V, Streuli I, Bischof P, deZiegler D. Undetectable serum-anti-Müllerian hormone levels and occurrence of ongoing pregnancy. Fertil Steril 2008;89 (2):723:e9-11.
Grant et al. "Follicular fluid steroid levels and subsequent sex of bovine embryos." Journal of Experimental Zoology, 2005; 303A: 1120-1125.
Barad DH, Oktay K, Weghofer A, Goyal A, Gleicher N. How predictive for pregnancy is very low anti-Müllerian hormone? Hum Reprod; Submitted for publication.
Macklou NS, Fauser BC. "Aspects of ovarian follicle development throughout life." Horm Res 1999; 83(2): 302-8.
Gleicher N., et al. Preliminary evidence that dehydroepiandrosterone (DHEA) increases the chance for the transfer of euploid embryos in women with diminished ovarian reserve. Hum Reprod—Submitted for priblication.
Gleicher N, Barad DH. "The effect of dehydroepiandrosterone on diminished ovarian reserve." Hum Reprod, 2006; 21 (S-1): i69.
Barad DH, Gleicher N,. "The effect of dehydroepiandrosterone on oocyte and embryo yields, embryo grade and cell number in IVF." Hum Reprod 2006; 21: 2845-9.
Brill H, et al. "Dehydroepiandrosterone supplementation and pregnancy outcome: Effect on pregnancy rate and speed of conception." Fertility and Sterility, 2006: (Suppl 1) In press.
Lossi K., et al. Androgen priming using aromatase inhibitor and hCG during early-follicular-phase GnRH antagonist down-regulation in modified antagonist protocols. Hum Reprod Advanced Access, Jun. 19, 2006.
Hsueh AJ, et al. "Gonadal cell apoptosis." Recent Prog Horm Res 1996; 51:433-55.
Weghofer A., et al. "Aneuploidy rates in embryos from women with prematurely declining ovarian function." Fertility and Sterility, In revision.
Munne S., et al. "Embryo morphology, developmental rates and maternal age are correlated with chromosome abnormalities." Fertility and Sterility, 1995; 64: 382-91.
Wu JM, et al. "Ovarian aging and menopause: current theories, hypotheses, and research models." Exp Biol Med 2005; 230:818-28.
Munne S., et al. "Referring Centers PGD Group. Preimplantation genetic diagnosis significantly reduces pregnancy loss in infertile couples: a multicenter study." Fertility and Sterility 2005; 85:326-32.
Barad DH, et al. Evidence towards an empiric definition of premature aging ovaries. Fertility and Sterility (Suppl 1) In Press.
Gleicher N., Barad D., "Premature ovarian aging and ovarian resistance in young women. Clinical Profile and IVF outcomes." Fertility and Sterility In Press.
Taranissi M., et al. "Influence of maternal age on the outcome of PGD for aneuploidy screening in patients with recurrent implantation failure." Reprod Biomed Online, 2005; 10: 628-32.
McNatty, KP., et al. "The microenvironment of the human antral follicle: interrrealtionships among the steroid levels in antral fluid, the population of granulose cells and the status of the oocyte in vivo and in vitro." J Clin Endocrinol Metab, 1979; 49: 851-60.

Andersen CY. "Characteristics of human follicular fluid associated with successful conception after in vitro fertilization." J Clin Endocrinol Metab, 1993; 77:1227-34.

Hillier SG, et al., "Location and developmental regulation of androgen receptor in primate ovary." Hum Reprod, 1997; 12: 107-11.

Weil S, et al. "Androgen and follicle-stimulating hormone interactions in primate ovarian follicle development." J Clin Endocrinol Metab, 1999; 84: 2951-6.

Krysko DV, Diez-Fraile A, Criel G, Svistunov AA, Vandenabeele P, D'Herde K. Life and death of female gametes during oogenesis and folliculogenesis. Apoptosis 2008;13:1065-87.

Otala M, Määkinen S, Tuuri T, Sjöberg J, Pentikäainen V, Matikainen T, Dunkel L. Effects of testosterone, dihydrotestosterone,and 17 beta-estardiol on human ovarian tissue survival in culture. Fertil Steril 2004 (Suppl 3): 84: 1077-1085.

Grant VJ. "Sex predetermination and the ethics of sex selection." Hum Reprod, 2006; 21: 1659-61.

Hardy ICW. "The birds and the wasps: a sex ratio meta-analysis." Trend Ecol Evol, 2002; 17: 207.

Conover Do, Van Voorhees DA. "Evolution of a balance sex ration by frequency-dependent selection in a fish." Science, Dec. 1990I 250: 1556-8.

Komdeur J, et al. "Pre-ovulation control of hatchling sex ratio in the Seychelle warbles." Proc Biol Sci, 2002; 269: 1967-72.

Veiga JP, et al. "Experimentally increased testosterone affects social rant and primary sex ratio in the spotless starling." Hoem Behave 2004; 46:47-53.

Krackow S., Potential mechanisms for sex ratio adjustment in mammals and birds. Biol Rev Camb Pholos Soc, 1995; 70:225-41.

Bouissou MF. "Effects of testosterone propionate on dominance relationships in a group of cows." Horm Bahav, 1978; 11:388-400.

Udry JR, et al. "Androgen effects on women have gendered behavior." J Biosoc Sci, 1995; 27:359-368.

Grant VJ, France JT. "Dominance and testosterone in women." Biol Psychol, 2001; 58:41-47.

Azziz R, et al. "Androgen excess in women: experience with over 1000 consecutive patients." J Clin Endocrinol Metab, 2004; 89: 453-62.

Gleicher N. "An evolutionary concept of polycystic ovarian disease: does evolution favour reproductive success over survival?" Reprod Biomed Online, 2006; 12:587-9.

Visser et al. "The applicability of the cumulative embryo score system for embryo selection and the quality control in an in-vitro fertilization/embryo transfer programme." Human Reproduction, 1993; 8:1719-1722.

Committee on Gynecologic Practice of American College of Obstetricians and Gynecologists; Practice Committee of American Society for Reproductive Medicine. Age-related fertility decline: a committee opinion. Fertil Steril 2008;90:486-7.

Letters to the editor, augmentation of ovarian response by dehydroepiandrosterone (comments from Peter R. Casson, John E. Buster and Sandra A. Carson.) http://humrep.oupjournals.org/cgi/content/full/16/7/1538, Jul. 20, 2004.

Acupuncture May Improve Success Rate of Test-Tube Pregnancies, Acupuncture Today, Jul. 2002, vol. 3, Issue 07.

Gleicher, et al. Update on In Vitro Fertilization approaches, US Obstetrics and Gynecology, vol. 3, Issue 2, (Dec. 10, 2010).

Al-Inany HG, Abou-Setta AM, Aboulghar M. Gonadotropin-releasing hormone antagonists for assisted conception. Cochrane Database Syst Rev 2006;19:pCD0011750.

Malizia BA, Hacker ME, Penzias A. Cumulative live-birth rates after in vitro fertilization. N Engl J Med 2009;360:236-43.

Franco JG, JR, Baruffi RL, Mauri AL, Petersen CG, Felipe V, Cornicelli J, Cavagna M, Oliveira JB. GnRH agonist versus GnRH antagonist in poor ovarian responders: a meta-analysis. Reprod Biomed Online 2006;13 (5): 618-627.

Gleicher N, Ryan E, Weghofer A, Oktay K, Blanco-Mejia S, Barad DH. Dehydroepiandrosterone (DHEA) supplementation in women with diminished ovarian reserve reduces miscarriages. Fertil Steril (in press), (2007; 88: 90-4).

Huirne JA, Homburg R, Lambalk CB. Are GnRH antagonists comparable to agonists for use in IVF? Hum Reprod 2007;22:2805-2813.

Lossl K, Yding Andersen C, Loft A, Freiesleben NLC, Bangsbøll S, Nyboe Andersen A. Short-term androgen priming by use of aromatase inhibitor and hCG before controlled ovarian stimulation for IVF. A randomized controlled trial. Hum Reprod 2008.

Roest J, van Heusden AM, Mous H, Zeilmaker GH, Verhoeff A. The ovarian response as a predictor of successful in vitro fertilization treatment after the age of 40 years. Fertil Steril 1996;66:969-973.

Taniguchi F, Couse JF, Rodriguez KF, Emmen JM, Poirier D, Korach KS. Estrogen receptor-alpha mediates an intraovarian negative feedback loop on thecal cell steroidogenesis via modulation of Cyp17a1 (cytochrome P450, steroid 17alpha hydroxylase/17,20 lyase) expression. FASEB J 2007;21:586-595.

Massin N, Cedrin-Durnerin I, Coussieu C, Galey-Fintaine J, Wolf JP and Hugues J-N (2006) Effects of transdermal testosterone application on the ovarian response to FSH in poor responders undergoing assisted reproduction technique—a prospective, randomized, double-blind study. Hum Reprod 21,1204-1211.

Larsen PR, Kronenberg HM, Melmed S, Polonsky KS. Williams textbook of endocrinology. 10th ed. Philadelphia: Saunders, 2003: 637-8.

van Kasteren YM, Schoemaker J. Premature ovarian failure: a systematic review on therapeutic interventions to restore ovarian function and achieve pregnancy. Hum Reprod Update 1999;5:483-92.

Meskhi A, Seif MW. Premature ovarian failure. Curr Opin Obstet Gynecol 2006;18:418-26.

The Practice Committee of the American Society for Reproductive Medicine. Current evaluation of amenorrhea. Fertil Steril 2006;86 (Suppl 4):148-55. Mamas L. Comparison of fallopian tube sperm perfusion and intrauterine tuboperitoneal insemination: a prospective study. Fertil Steril 2006;85:735-40.

Anasti JN. Premature ovarian failure: an update. Fertil Steril 1998;70:1-15.

Hamilton BE, Martin JA, Sutton PD. Births: preliminary data for 2003. Natl Vital Stat Rep 2004:53:1-17. Pinborg A, Hougaard C, Nyboe Andersen A, Molbo D, Schmidt L. Prospective longitudinal cohortstudy on cumulative 5-year delivery and adoption rates among 1338 couples initiating infertility treatment. Hum Reprod 2009;24:991-9.

van Rooij IA, Broekmans FJ, Scheffer GJ, Looman CW, Habbema JD, de Jong FH, Fauser BJ, Themmen AP, te Velde ER. Serum antimullerian hormone levels best reflect the reproductive decline with age in normal women with proven fertility: a longitudinal study. Fertil Stril 2005;83:979-87.

Gleicher N, Ryan E, Weghofer A, Oktay K, Blanco-Mejia S, Barad DH. Dehydroepiandrosterone (DHEA) reduces miscarriage rates in women with diminished ovarian reserve: A multicenter study. Fertil Steril 2008;90 (Suppl 1): S258-0.

Tremellen KP, Kolo M, Gilmore A, Lekamge DN. Anti-mullerian hormone as marker of ovarian reserve. Aust N Z J Obstet Gynaecol 2005;45:20-4.

La Marca A, Volpe A. Anti-Müllerian hormone (AMH) in female reproduction: is measurement of circulating AMH a useful tool? Clin Endocrinol (Oxf) 2006;64:603-10.

Gnoth C, Schuring An, Friol K, Tigges J, Mallmann P, Godehardt E. Relevance of anti-Mullerian hormone measurement in routine IVF program. Hum Reprod 2008;23:1359-65.

Barad DH, Weghofer A, Gleicher N. Comparison of anti-Mölleria hormone (AMH) and follicle stimulating hormone (FSH) a predictors of ovarian function. Fertil Steril. Feb. 11, 2009.

Rohr J, Allen EG, Charen K, Giles J, He W, Domingues C, Sherman SL. Anti-Mullerian hormone indicates early ovarian decline in fragile X mental retardation (FMR1) permutation carriers: a preliminary study. Hum Reprod 2008;23:1220-5.

Kevenaar ME, Meerasahib MF, Kramer P, van de Lang-Born BMN, de Jong FH, Groome NP, Themmen APN, Visser JA. Serum AMH levels reflect the size of the primordial follicle pool in mice. Endocrinology 2006;147:3228-34.

Faddy MJ. Follicle dynamics during ovarian ageing. Mol Cell Endocrinol 2000;163:43-8.

Mamas L, Mamas E. Premature ovarian failure and dehydroepiandrosterone. Fertil Steril 2009;91:644-6.

Ryan EAJ, Claessens EA, Blanco Mejia S. The sex-ratio of offspring born to women, using dehydroepiandrosterone (DHEA) to improve ovarian response. Fertil Steril 2008;90 (Suppl 1):S116-7.

Casson PR, Santoro N, Elkind-Hirsch K, et al. Postmenopausal dehydroepiandrosterone administration increases free insulin-like growth factor-I and decreases high density lipoprotein: a six-month trial. Fertil Steril 1998;70:107-10.

Casson PR, Linday MS, Pisarska MD, Carson SA, Buster JE: Dehydroepiandrosterone supplementation augments ovarian stimulation in poor responders: a case series. Hum Reprod 2000,15:2129-2132.

Barad DH, Gleicher N: Increased oocyte production after treatment with dehydroepiandrosterone. Fertil Steril 2005, 84:756.e1-3.

Barad D, Gleicher N: Effect of dehydroepiandrosterone on oocyte and embryo yields, embryo grade and cell number in IVF. Hum Reprod 2006,21:2845-2949.

Barad D, Brill H, Gleicher N: Update on the use of dehydroepiandrosterone supplementation among women with diminished ovarian function. J Assist Reprod Genet 2007, 24:629-634.

Casson PR, Santoro N, Elkind-Hirsch K, Carson SA, Hornsby PJ, Abraham G, Buster JE. Postmenopausal dehyroepiandrosterone administration increases free insulin-like growth factor-I and decreases high-density lipoprotein: a six-month trial. Fertil Steril 1998, 70:107-10.

Gleicher N, Weghofer A, Barad D: Increased euploid embryos after supplementation with dehydroepiandrosterone (DHEA) in women with premature ovarian aging. Fertil Steril 2007,88 (Suppl 1):S232.

Morales C, Sánchez A, Bruguera J, Margarit E, Borrell A, Borobio V, Soler A. Cytogenetic study of spontaneous abortions using semi-direct analysis of chorionic villi samples detects the broadest spectrum of chromosome abnormalities. Am J Med Genet 2008, 146A:66-70.

te Velde ER, Pearson PL. The variability of female reproductive ageing. Hum Reprod Update 2002, 8:141-154.

Pal L, Santoro N. Age-related decline in fertility. Endocrinol Metab Clin North Am 2003, 32:669-688.

Gleicher N, Weghofer A, Barad D. Preimplantation genetic screening (PGS), "established" and ready for prime time? Fertil Steri. 2008, 89:780-788.

Barad DH, Weghofer A, Gleicher N. Age-specific levels for basal follicle-stimulating hormone assessment of ovarian function. Obstet Gynecol 2007, 109:1404-1410.

Wright VC, Chang J, Jeng G, Chen M, Macaluso M. Assisted reproduction technology surveillance—United States, 2004; MMWR Surveill Summ 2007, 56:1-22.

Levi AJ, Raynault MF, Bergh PA, Drews MR, Miller BT, Scott RT.Jr. Reproductive outcome in patients with diminished ovarian reserve. Fertil Steril 2001, 76:666-669.

Golbus MS, Loughman WD, Epstein CJ, Halbasch G, Stephens JD, Hall BD. Prenatal genetic diagnosis in 3000 amniocenteses. N Engl J Med 1979, 300:157-163.

Gianaroli L, Magli MC, Ferraretti AP, Munè S. Preimplantation diagnosis for aneuploidies in patients undergoing in vitro fertilization with a poor prognosis: identification of the categories for which it should be proposed. Fertil Steril 1999,72:837-844.

Magli MC, Gianarol L, Ferraretti AP. Chromosomal abnormalities in embryos. Mol Cell Endocrinol 2001, 183 Suppl 1: S29-34.

Munnè S, Chen S, Coils P, Garrisi J, Zheng X, Cekleniak N, Lenzi M, Hughes P, Fischer J, Garrisi M, Tomkin G, Cohen J. Maternal age, morphology, development and chromosome abnormalities in over 6000 cleavage-stage embryos. Reprod Biomed Online 2007,74:628-634.

Weghofer A, Barad D, Li J, Gleicher N. Aneuploidy rates in embryos from women with prematurely declining ovarian function: a pilot study. Fertil Steril 2007, 88:90-94.

Gleicher N, Barad D. "Ovarian age based" stimulation of young women wih diminished ovarian reserve results in excellent pregnancy rates with in vitro fertilization. Fertil Steril 2006, 86:1621-1625.

Kumbak B, Oral E, Kahraman S, Karlikaya G, Garagozoglu H. Young patients with diminished ovarian reserve undergoing assisted reproductive treatments: a preliminary report. Reprod Biomed Online 2005, 11:294-299.

Gleicher N, Weghofer A, Barad D. Too old for IVF: are we discriminating against older women? J Assist Reprod Genet 2007, 24:639-644.

Gianaroli L, Magli MC, Ferraretti AP, Tabanelli C, Trombetta C, Boudjema E The role of preimplantation diagnosis for aneuploidies. Reprod Biomed Online 2004, 4 Suppl 3:31-36.

Practice Committees of the Society for Assisted Reproductive Technology and American Society for Reproductive Medicine. Preimplantation genetic testing: a Practice Committee opinion. Fertil Steri. 2007, 88:1497-1504.

Devroey P, Fauser BCJM. Preimplantation aneuploidy screening: a research tool for now. Lancet 2007, 370:1985-1986.

Ben-Rafael Z, Fateh M, Flickinger GL, Tureck R, Blasco L, Mastroani L Jr. Incidence of abortion in pregnancies after in vitro fertilization and embryo transfer. Obstet Gynecol 1988, 71:297-300.

Ventura SJ, Mosher WD, Curtin SC, Abma JC, Henshaw S. Highlights of trends in pregnancies and pregnancy rates by outcome: estimates for the United States, 1976-96. Natl Vit Stat Rep 1999, 15:47:1-9.

Blohm F, Fridén B, Milsom I. A prospective longitudinal population-based study of clinical miscarriage in an urban Swedish population. BJOG 2008, 115:176-182.

Hodges CA, Ilagan A, Jennings D, Keri R, Nilson J, Hunt PA. Experimental evidence that changes in oocyte growth influence meiotic chromosome segregation. Hum Reprod 2002, 17:1171-80.

Chung, CC et al, "Age is a better predictor of pregnancy potential than basal follicle-stimulating hormone levels in women undergoing in vitro fertilitzation." Fertility and Sterility. Jan. 2003, pp. 63-68. vol. 79. No. 1, Elsevier Science Inc. USA.

Munne, S. et al., "Improved implantation after preimplantation genetic diagnosys of aneuploidy," Reproductive BioMedicine Online, May 2003, pp. 91-97, vol. 7, No. 1.

Giranaroli, L. et al., "Will preimplantation genetic diagnosis assist patients with a poor prognosis to achieve pregnancy?" Human Reproduction, 1997, pp. 1762-1767, vol. 12. No. 8. European Society for Human Reproduction and Embryology, Belgium.

Karande, V and Gleicher, N., "A rational approach to the management of low responders in in-vitro fertilization" Human Reproduction and Embryology, Belgium.

Paulus, W., et al., "Influence of acupuncture on the pregnancy rate in patients who undergo assisted reproduction therapy." Fertility and Sterility, Apr. 2002, vol. 77, No. 4, 721-724.

Frattarelli and Petterson, "Effect of androgen levels on in vitro fertilization cycles," Fertility and Sterility , Jun. 2004, vol. 81, No. 6, Elsevier Science Inc. U.S.A.

Faddy, M.J., "Follicle dynamics during ovarian ageing,"Molecular and Cellular Endocrinology, 2000, pp. 42-48, vol. 163, Elsevier Science Ireland Ltd.

Folicori, M. "The role of luteinizing hormone in folliculogenesis and ovulation induction," Fertility and Sterility, Mar. 1999, pp. 405-414, vol. 71, No. 3, Elsevier U.S.A.

Franks, S. et al, "Follicular dynamics in the polycystic ovary syndrome,"Molecular and Cellular Endocrinology, 2000, pp. 49-52, vol. 163. Elsevier Science Ireland Ltd.

Burger, H. "Androgen production in women," Fertility and Sterility, Apr. 2002, pp. S3-S5. vol. 77, No. 4, Suppl. 4, Elsevier Science Inc. USA.

Anderson, E. "Polycystic ovarian condition in the dehydroepiandrosterone-treated rat model: hyperandrogenism and the resumption of meiosis are major initial events associated with cytogenesis of antral follicles," Anatomical Record, 249, pp. 44-53, 1997. Wiley-Liss, Inc.

Johnson, J. et al., "Gemline stem cells and follicular renewal in the postnatal mammalian ovary," Nature Mar. 2004, pp. 145-150, vol. 428, Nature Publishing Group, Boston Massachusetts.

Haning, R. et al., "Plasma dehydroepiandrosterone sulfate serves as a prehormone for 48% of follicular fluid testosterone during treatment with menotropins," Journal of Clinical Endicrinology and Metabolism, 1993, pp. 1301-1307, vol. 76, No. 5, JCE & M, USA.

Casson, P. et al. "Postmenopausal dehydroepiandrosterone administration increases free insulin-like growth factor-I and decreases high-density lipoprotein: a six month trial," Fertility and Sterility Jul. 1998, pp. 107-110, vol. 70, No. 1.

Kloza, B. et al. "New fertility boost," ScienCentral News Oct. 13, 2004, pp. 1-4, ScienCentral Inc., USA.

Orvieto, R, et al. "Results of in vitro fertilization cycles in women aged 43-45 years," Gynecol. Endocrinology 2003, pp. 75-78., vol. 18, No. 2.

Kupesic, S., et al. "Three-dimensional ultrasonographic ovarian measurements and in vitro fertilitzation outcome are related to age," Fertility and Sterility, 1999, pp. 190-197. vol. 79. No. 1.

Kroboth PD, et al., "DHEA and DHEA-S: a review," Journal of Clinical Parmacol., 1999 pp. 327-348, vol. 39, No. 4.

Roy, S., et al., "The effect of dehydroepiandrosterone and D4-androstenendione on the reproductive organs of female rate: Production of cystic changes in the ovary," Nature 162 pp. 42-43, vol. 196, (Oct. 6, 1962).

Amirikia, H., et al., "The effects of long term androgen treatment on the ovary." Fertility and Sterility, 1986. pp. 202-208. vol. 45, No. 2.

Hofmann, G.E., et al. "High-dose follicule-stimulating hormone (FSH) ovarian stimulation in low-responder patients for in vitro fertilization" Journal of in vitro Fertilization and Embryo Transfer, 1989, 6, 285-289.

Surrey, E. S., et al. Clinical and endocrine effects of amicrodose GnRH agonist flare regimen administered to poor responders who are undergoing in vitro fertilization. Fertility and Sterility, 1998, 69, 419-424.

* cited by examiner

FIG. 1

| DHEA use | Cycle | Date | Cycle FSH mI/Uml | Day 3 Estradiol pg/ml | Peak Estradiol pg/ml | Total Oocytes # | Total Oocytes Mean ± SD[1] | Mature oocyte # | 2pn | Day 3 embryos # | Cryopreserved Mean ± SD[2] |
|---|---|---|---|---|---|---|---|---|---|---|---|
| Early[3] | 1 | 09/03 | 10.59 | 18 | 330 | 1 | 2 ± 1.4 | | 1 | 1 | 2.0 ± 1.4 |
| | 2 | 11/03 | 8.11 | 48 | 619 | 3 | | 3 | 3 | 3 | |
| Mid | 3 | 12/03 | 1.99 | 26 | 975 | 5 | 5.7 ± 1.2 | 5 | 5 | 5 | 5.3 ± 0.6 |
| | 4 | 01/04 | 15.18 | 5 | 908 | 7 | | 7 | 6 | 6 | |
| | 5 | 02/04 | 3.43 | 76 | 901 | 5 | | 5 | 5 | 5 | |
| Late | 6 | 03/04 | 4.96 | 70 | 3251 | 13 | 16.0 ± 3.0 | 12 | 9 | 9 | 10.0 ± 1.0 |
| | 7 | 05/04 | 1.70 | 42 | 3150 | 16 | | 12 | 10 | 10 | |
| | 8 | 06/04 | 2.42 | 75 | 5055 | 19 | | 16 | 13 | 11 | |

[1] (*early* & *mid*) vs. *late*, $p = 0.0001$; *early* vs. *mid*, ns; Linear trend across group $F=51.9$; 1 df; $p = 0.001$
[2] (*early* & *mid*) vs. *late*, $p < 0.001$; *early* vs. *mid*, $p = 0.01$; Linear trend across group $F=82.3$; 1 df; $p < 0.001$
[3] DHEA treatment began 2 weeks before the start of the second cycle on October 6, 2003.

Adrenal function of 17, 20 desmolase (P450c17) \*

\*Modified from Speroff et al., (1999a); Cytochrome P450 is a generic term used for a group of oxidative enzymes active in steroidogenesis. P450c17 is the enzyme mediating 17-hydroxylas and 17, 20- lyase.

FIG. 11

| | IVF Patients (n=288) | | | All Patients (n=778) | | |
|---|---|---|---|---|---|---|
| | Mean | 95% CI | | Mean | 95% CI | |
| Age (years) | 35.7 | 34.9 - 36.4 | | 35.7 | 35.2 - 36.1 | |
| BMI | 24.9 | 23.7 - 26.1 | | 24.3 | 23.6 - 25.0 | |
| | n | % | | n | % | |
| Race | | | | | | |
| African | 40 | 13.9% | | 90 | 11.6% | |
| Asian | 55 | 19.1% | | 160 | 20.6% | |
| Caucasian | 193 | 67.1% | | 528 | 67.8% | |
| Diagnosis | | | | | | |
| Oocyte Donors | 23 | 8.0% | | 81 | 10.4% | |
| Infertility Patients | 265 | 92.0% | | 697 | 89.6% | |
| DOR/POA | 148 | 51.4% | | 381 | 54.7% | |
| Male infertility | 40 | 13.9% | | 118 | 17.0% | |
| Tubal infertility | 58 | 20.2% | | 143 | 20.5% | |
| Other | 19 | 6.6% | | 54 | 7.8% | |

FIGURE 12

| | Age (Years) | | | | | | | |
|---|---|---|---|---|---|---|---|---|
| | < 30 (n=31) | | 30 – 34 (n=45) | | 35 to 40 (n=122) | | >40 (n=8) | |
| | Mean | 95% CI | Mean | 95% CI | Mean | 95% CI | Mean | 95% CI |
| AMH (ng/mL) | 3.8 | 3.1 - 4.6 | 2.0* | 1.5 - 2.7* | 0.9* | 0.8 - 1.1* | 0.4* | 0.2 - 1.0* |
| FSH (IU/mL) | 6.4 | 5.7 - 7.1 | 7.9 | 7.4 - 8.5 | 8.1 | 7.7 - 8.5 | 10.0 | 9.1 - 10.9 |
| Estradiol (pg/mL) | 47.4* | 40.5 - 55.6* | 46.9* | 41.8 - 52.7* | 53.5* | 48.1 - 59.6* | 60.1 | 14.9 - 105.4 |

* Back- transformed after logarithmic transformation

AMH levels decrease significantly between age categories (p<0.001), while FSH increases (p = p<0.001) and estradiol remains unchanged.

FIGURE 13

OOCYTE YIELDS

| Age (years) | Low (<95% CI) as-AMH | | | Normal (95% CI) as-AMH | | | High (>95% CI) as-AMH | | |
|---|---|---|---|---|---|---|---|---|---|
| | n IVF cycles | Mean | 95% CI | n IVF cycles | Mean | 95% CI | n IVF cycles | Mean | 95% CI |
| <30 | 20 | 11.0(b,c) | 7.9 - 14.0 | 12 | 17.5(a) | 12.1 - 22.9 | 15 | 15.9(a) | 12.4 - 19.5 |
| 30 - 34 | 30 | 6.1(c) | 4.5 - 8.3 | 12 | 10.3(c) | 7.6 - 13.1 | 25 | 18.6(a,b) | 14.7 - 22.5 |
| 35 - 39 | 80 | 4.4(b,c) | 3.6 - 5.5 | 33 | 6.8(a) | 5.5 - 8.1 | 48 | 9.6(a) | 8.4 - 11.1 |
| > 40 | 8 | 2.6 | 1.3 - 4.0 | 0 | - | - | 4 | 5.8 | -1.4 - 12.9 |

Superscripts denote significant difference (p < 0.05) from designated column within age categories:
(a) – denotes low *as*-AMH;
(b) – denotes normal *as*-AMH;
(c) – denotes high *as*-AMH Total oocytes yields in women with *as*-normal and high AMH were significantly higher than those in women *as*-low AMH (F= 78.9, df 1; p < 0.00001)

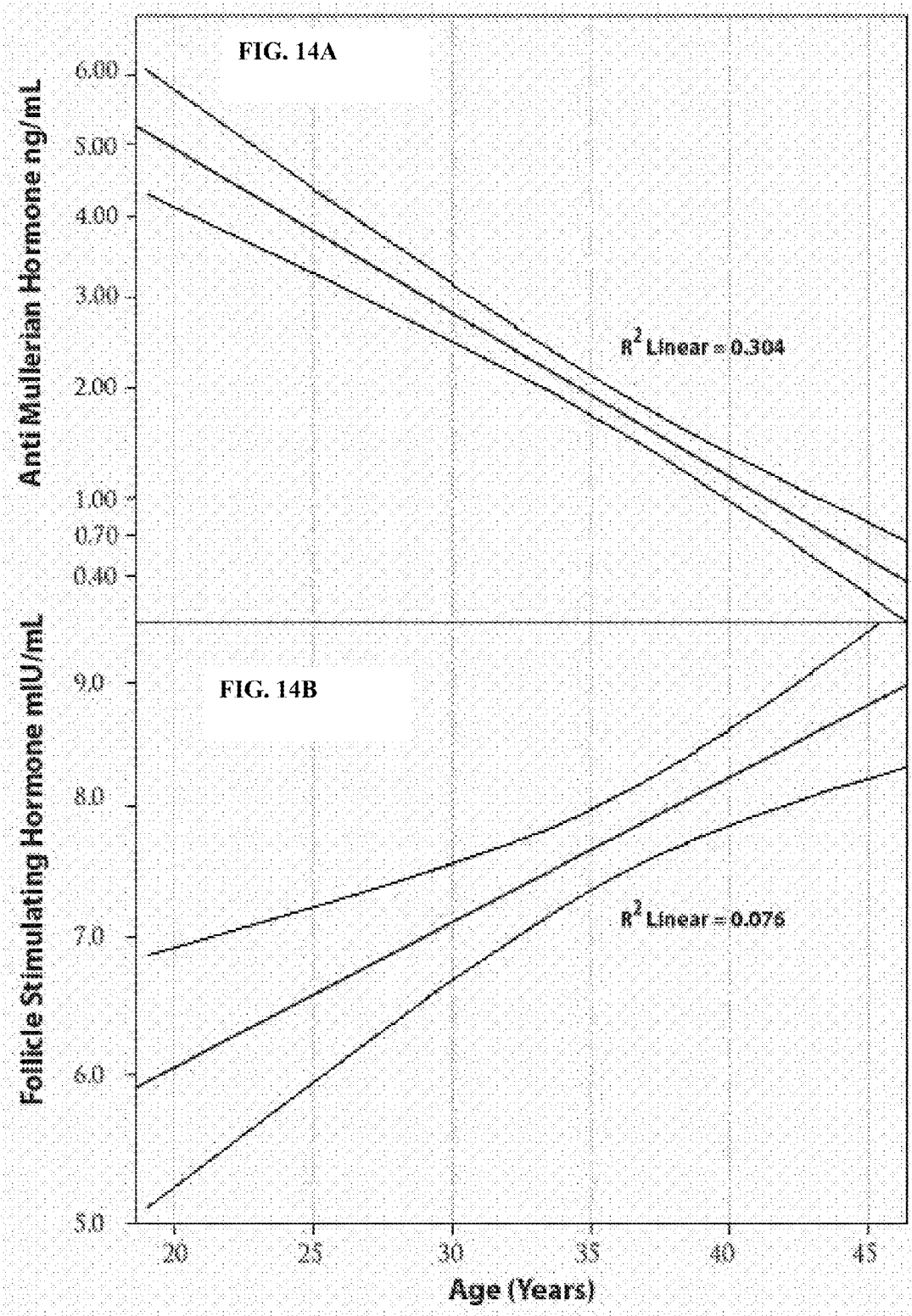

FIG. 17

|  | Pre-DHEA | Post-DHEA | p- value |
|---|---|---|---|
| Cycle cancellations (%) | 32.0 | 4.3 | 0.02 |
| Number oocytes | 3.4 ± 0.5 | 4.4 ± 0.5 | <0.05 |
| Fertilized oocytes (n) | 1.4 ± 0.3 | 3.0 ± 0.5 | <0.001 |
| (%) | 39 | 67 | <0.001 |
| Day 3 blastomeres | 3.4 ± 0.4 | 4.7 ± 0.5 | 0.01 |
| embryo grade | 2.9 ± 0.1 | 3.4 ± 0.1 | 0.02 |
| Cumulative embryo score/oocytes | 8.4 ± 1.5 | 16.1 ± 1.6 | 0.001 |
| Number of transferred embryos | 1.4 ± 0.2 | 2.4 ± 0.3 | 0.005 |
| Normal day 3 embryos | 1.2 ± 0.2 | 2.7 ≤ 0.4 | 0.001 |

FIG. 18

| DHEA effects |
|---|
| Pregnancies/live births at all AMH levels; Not even undetectable levels of AMH, therefore, preclude pregnancies/live births; |
| Pregnancies lowest [1] at AMH levels <0.1 (undetectable) -0.4 ng/mL, intermediate [2] at AMH 0.41-1.05 ng/ML and high [3] ≥ AMH 1.06 ng/mL |
| Spontaneous miscarriage rates lowest [4] at AMH ≤ 0.4 ng/mL and 1.06 ng/mL; Highest [5] at AMH 0.41-1.05 ng/mL. |
| Live births rates uniformly low [6] at AMH <0.1-1.05 ng/mL and high [7] at AMH ≥ 1.6 ng/mL; |
| AMH increases in parallel with length of DHEA supplementation; |
| This increase is more pronounced in younger POA than older DOR patients; |
| Improvement in AMH levels with DHEA supplementation is highly predictive of pregnancy success |

[1] Approximately 5 % per cycle, 10 % cumulative; [2] Approximately 10 % per cycle and 17 % cumulative; [3] Approximately 28 % per cycle and 42% cumulative. [4] Approximately <15 %; [5] Approximately 50%; [6] Approximately 4 % per cycle, 7 % cumulative; [7] Approximately 22 % per cycle, 32 % cumulative

ANDROGEN TREATMENT IN FEMALES

This application is a continuation-in-part of application Ser. No. 11/269,310, filed on Nov. 8, 2005, and Ser. No. 12/123,877, filed on May 20, 2008, and Ser. No. 12/575,426, filed on Oct. 7, 2009, which are incorporated by reference in their entirety.

BACKGROUND OF THE INVENTION

1. Field of the Invention

The present invention relates to the field of reproductive technology.

2. Description of the Related Art

The application of assisted reproductive technology has revolutionized the treatment of all forms of infertility. The most common assisted reproductive technology is in vitro fertilization (IVF), in which a woman's eggs are harvested and fertilized with a man's sperm in a laboratory. Embryos grown from the sperm and eggs are then chosen to be transferred into the woman's uterus. Assisted reproductive technology in women depends on ovarian stimulation and concurrent multiple oocyte development, induced by exogenous gonadotropins.

Infertile women are often treated with gonadotropin treatments such as gonadotropin-releasing hormone (GnRH) flare protocols. Estrogen pre-treatment with concomitant growth hormone (GH) treatment is sometimes used in an effort to try and amplify intra-ovarian insulin-like growth factor-I (IGF-I) paracrine effect, which is expressed by granulosa cells and enhances gonadotropin action. However, the clinical utility of combined GH/ovarian stimulation is limited and responses are not dramatic.

Dehydroepiandrosterone (DHEA) is secreted by the adrenal cortex, central nervous system and the ovarian theca cells and is converted in peripheral tissue to more active forms of androgen or estrogen. DHEA secretion during childhood is minimal but it increases at adrenarche and peaks around age 25, the age of maximum fertility, only to reach a nadir after age 60. There is evidence to support use of exogenous DHEA to increase ovulation stimulation in older women who respond poorly to gonadotropin treatments.

Women with diminished ovarian function have decreased egg production and the eggs that are produced usually are of a poor quality. Further, women with diminished ovarian function tend to encounter difficulty becoming pregnant with or without IVF and experience long time periods to conception and/or have an increased possibility of miscarriage.

Women with diminished ovarian function have largely been considered to be untreatable.

BRIEF SUMMARY OF THE INVENTION

The present invention is directed to a method of using dehydroepiandrosterone (DHEA) to treat a human female with diminished ovarian reserve. The method includes measuring a baseline follicle stimulating hormone (FSH) level of the human female, and when the baseline FSH level is below about 40.0 mIU/ml, administering about 75 milligrams of DHEA per day to the female for at least four months to treat ovarian follicles in at least one ovary of the female to improve human folliculogenesis during the at least four months.

The present invention further is directed to a method of restoring the ovarian environment of an older human female to that of a younger human female. The method includes administering about 75 milligrams of DHEA per day to the female for at least four months.

The present invention also is directed to a method of treating a human female with diminished ovarian reserve. The method includes administering about 75 milligrams of dehydroepiandrosterone (DHEA) per day to the female for at least four months to expose ovarian follicles of the female to DHEA to improve human folliculogenesis during the at least four months and evaluating whether the female is pregnant. When the female is not pregnant, continue administering about 75 milligrams per day of DHEA to the female until the female becomes pregnant. When the female is pregnant, stop administering DHEA to the female.

BRIEF DESCRIPTION OF THE DRAWINGS

FIG. 1 is a table showing improved ovulation induction with DHEA.

FIG. 11 is a table showing patient characteristics.

FIG. 12 is a table showing hormone levels among 206 patients with normal baseline FSH.

FIG. 13 is a table showing oocyte yields among patients reaching IVF.

FIG. 14A is a graph showing as-AMH levels (Anti Mullerian Hormone ng/ml).

FIG. 14B is a graph showing as-FSH levels (Follicle Stimulating Hormone mIU/ml).

FIG. 17 is a table showing comparisons of pre- and post-DHEA cycles in 25 women with DOR.

FIG. 18 is a table showing effectiveness of DHEA supplementation in IVF pregnancies based on AMH.

DETAILED DESCRIPTION OF THE INVENTION

Figure 2:
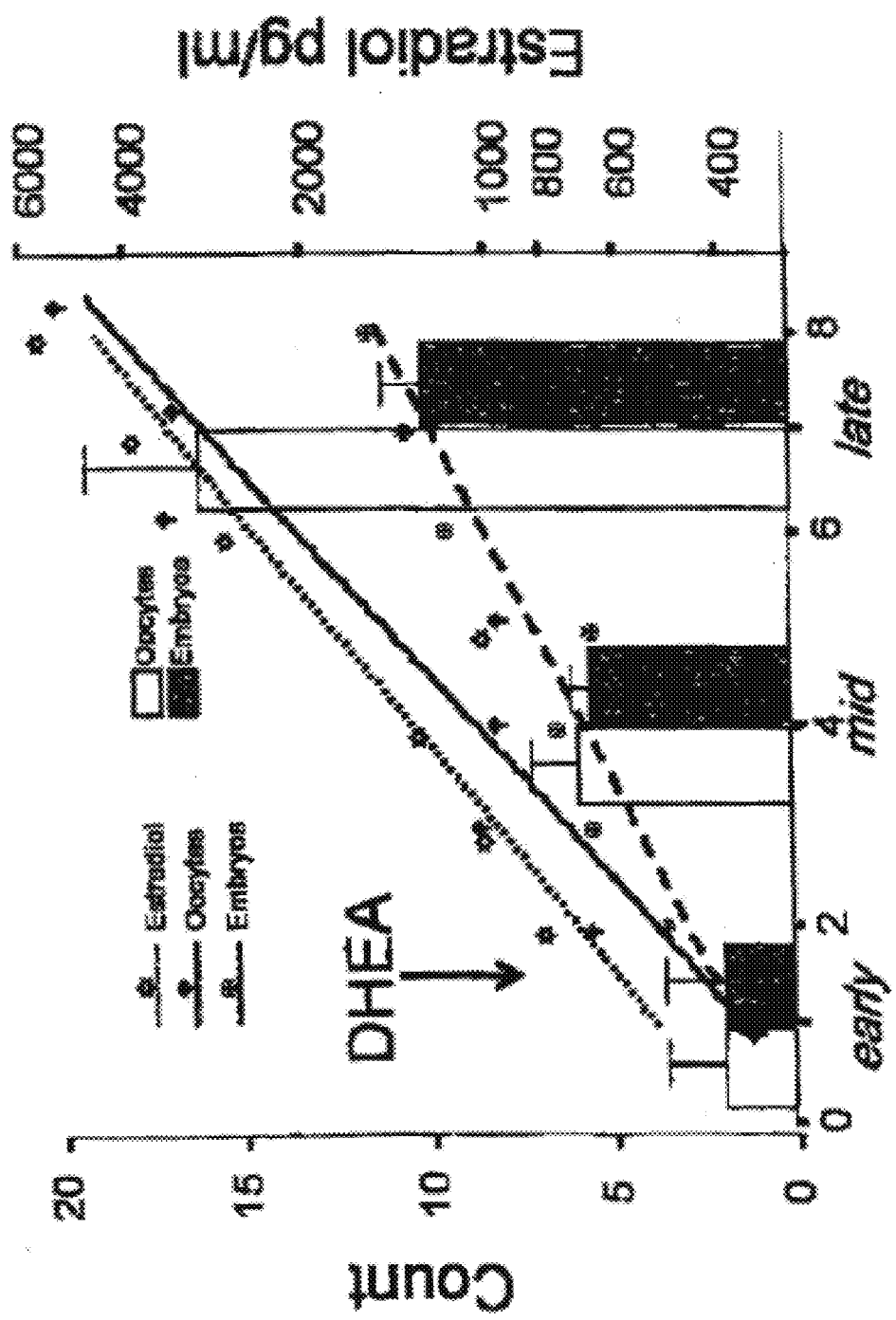
FIG. 2 is a graph showing an increase in the number of fertilized oocytes resulting from oocytes harvested from women with DHEA treatment.

When attempting in vitro fertilization (IVF), older women produce few oocytes and yield few normal embryos, even when exposed to maximal gonadotropin stimulation. The decreased ability of older women to respond to ovulation inducing medications is evidence that ovarian reserve declines with age. Even with IVF cycles, older women produce few oocytes and yield few normal embryos when exposed to maximal gonadotropin stimulation. This change in ovarian responsiveness is known as diminished ovarian reserve or diminished ovarian function.

To improve the number of eggs, the quality of eggs, the number of embryos, the quality of the embryos, spontaneous pregnancy rates, IVF pregnancy rates, cumulative pregnancy rates and time to conception, to reduce the miscarriage rates, and to increase the male/female birth ratio, DHEA is administered for at least two months to a human female in a therapeutically effective amount. Preferably, the human female is a premenopausal human female. The human female may have diminished ovarian reserve. DHEA may be administered to a human female at a dose of between about 50 mg/day and about 100 mg/day, preferably between about 60 mg/day and about 80 mg/day, and in one study about 75 mg/day. Further, DHEA may be administered in a time-release formulation, over the course of the day, or in a single dose. For example, the about 75 mg/day could be administered in a single dose of 75 mg or could be administered as 25 mg three times throughout the day. DHEA is preferably administered orally, although DHEA may be administered or delivered via other methods, such as, but not limited to, intravenously and/or topically. DHEA has a statistically significant effect on the above-mentioned factors after about 2 months of use, but its effect may continue to increase to about four months or about 16 weeks, preferably about four consecutive months or about 16 consecutive weeks, and further may continue past four months of use.

The effects of DHEA increase over time, and may reach peaks after approximately four to five months of supplementation. It is suggested that peaks may occur at four to five months because this time period is similar to the time period of a complete follicular recruitment cycle. Further, the effect of DHEA is suggested to reduce chromosomal abnormalities and thus substantially decreasing miscarriage rates in human females.

I. Improvements in Ovulation

Treatments with an androgen, alone or in conjunction with other hormones, increase a woman's response to ovulation induction, measured in both oocyte and embryo yield. Androgens may be, for example, dehydroepiandrosterone (DHEA) or testosterone. DHEA treatment may be an adjunct to ovulation induction. DHEA taken orally for at least about one month, preferably for about four months, before optionally initiating gonadotropin treatment, may prepare the ovaries for gonadotropin stimulation. A large response may be obtainable by combining gonadotropins and DHEA in treatment for at least about a four month period before an IVF cycle.

Young ovaries are characterized by large numbers of antral follicles and a low rate of atresia. In contrast, older ovaries have few antral follicles, high rates of atresia and exhibit increasing "resistance" to ovulation induction. Older women have decreased oocyte quantity and quality, produce fewer high quality embryos and have lower implantation and pregnancy rates. Most follicular atresia occurs after the primordial follicle resumes growth but before it is gonadotropin responsive enough for recruitment. An induced delay in onset of atresia may salvage follicles for possible ovulation. Interestingly, such an "arrest" of the atretic process has been noted among anovulatory women with polycystic ovary syndrome (PCO). For these women follicles remain steroidogenicaly competent and show evidence of increased aromatase activity compared to like-sized follicles from normal ovaries. Follicular hypersecretion of DHEA, which is typical of PCO, is associated with increased aromatase activity. The increased yield of oocytes and embryos experienced by patients undergoing DHEA treatment may correspond to this underlying physiological process.

II. Improvements to Cumulative Embryo Score

DHEA use beneficially effects oocyte and embryo quality. The observation that DHEA treatment is associated with improved cumulative embryo scores infers that such treatment leads to improved embryo and egg quality. This suggestion is further supported by strong trends towards improved euploidy in embryos and improved pregnancy rates.

DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA has a statistically significant effect on cumulative embryo score after about 2 months of administration, but its effect may continue to increase to about four months, or about 16 weeks, and further may continue past four months of use.

Cumulative embryo score is determined by scoring day 3 embryos and multiplying the number of cells in the embryo by the embryo grade. Embryo grade is a judgment of the embryologist on embryo quality from 1 to 5. Most good embryos are scored 4, with 5 reserved for exceptional embryos. The grade is based on the uniformity of the cells, the color and consistency of the cytoplasm, and the amount of fragmentation. Normal embryos are less than 5% fragmented. A woman with three eight cell embryos each with a grade of four would have a cumulative embryos score of 96, the product of 3×8×4.

A cumulative embryo score for women prior to DHEA use may have been about 34. A cumulative embryo score after DHEA use of at least about four consecutive months may be at least about 90, preferably at least about 95, and in one study at least about 98. The increase in cumulative embryo score may be at least about 56, preferably at least about 60, and in one study about 64. The difference in the cumulative embryo score prior to DHEA use and the cumulative embryo score after DHEA use is statistically significant, p<0.001. The mean increase in embryo score was about 57+/−14.7 after about 16.1 weeks of DHEA administration. As such, DHEA treatment significantly improves the cumulative embryo score.

III. Increase in the Number of Fertilized Oocytes

DHEA treatment significantly increased the number of fertilized oocytes produced by women. DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA may have an effect on the number of fertilized oocytes after about 4 consecutive weeks. However, DHEA has a significant effect on the number of fertilized oocytes after about 8 weeks or about 2 months of administration, and its effect may continue to increase to about four months, and further may continue past four months of use. Specifically, DHEA treatment has a statistically significant effect after about at least 16 weeks or about at least 4 months of administration.

Figure 3:
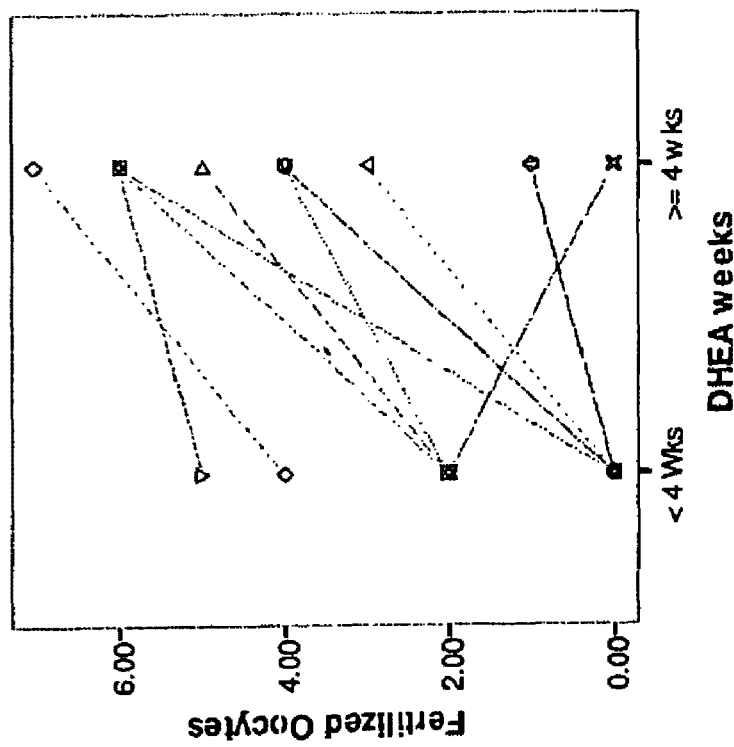
FIG. 3 is a graph showing an increase in the number of fertilized oocytes resulting from oocytes harvested from women with at least 4 weeks of DHEA treatment.

The number of fertilized oocytes produced by women significantly increased after at least about 4 months of consecutive DHEA treatment in 12 women, even though slight improvements were shown after at least about four weeks of consecutive DHEA treatment, as shown in FIG. 3. As shown in FIG. 3, paired comparisons of fertilized oocytes from women having less than about four consecutive weeks of DHEA treatment to the same women having at least about four consecutive weeks of DHEA treatment showed an increase of about 2 fertilized oocytes, or a median increase of about 2.5 fertilized oocytes. The number of fertilized oocytes may show more significant increase after at least about 4 months of DHEA treatment, and may show maximal increase after at least about eight months of DHEA treatment.

IV. Increase in the Number of Day 3 Embryos

DHEA treatment significantly increased the number of day 3 embryos produced by women. DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA may have an effect of day 3 embryos after about 4 consecutive weeks. However, DHEA has a significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

Figure 4:
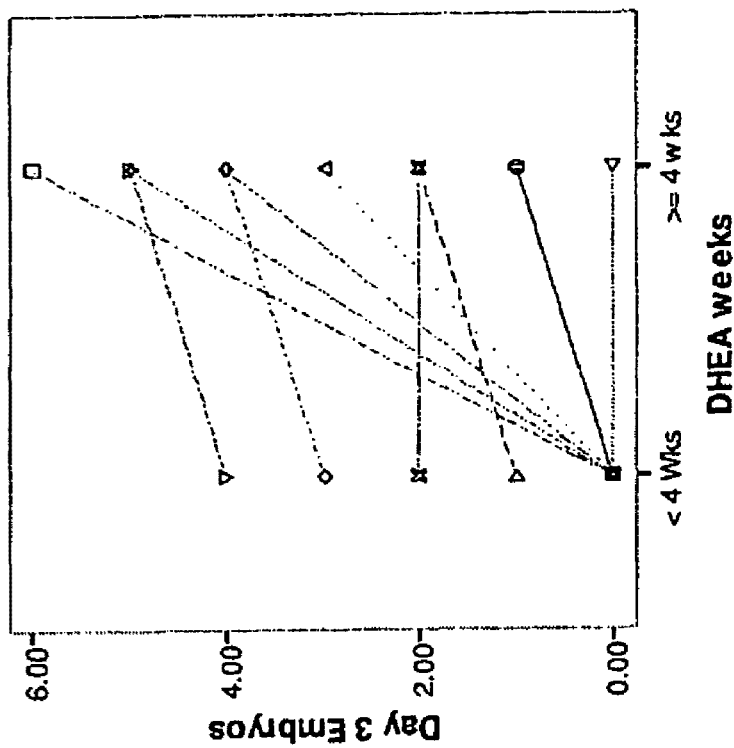
FIG. 4 is a graph showing an increase in the number of day three embryos resulting from oocytes harvested from women with at least 4 weeks of DHEA treatment.

The number of day 3 embryos produced by women also may significantly increase after at least about four months of consecutive DHEA treatment in 12 women, even though slight increases may be shown after at least about 4 weeks of DHEA treatment, as shown in FIG. 4. All of the day 3 embryos included in the study were normal based on their appearance and on the number of cells, i.e. at least four cells. Paired comparisons of fertilized oocytes from women having less than about four consecutive weeks of DHEA treatment to the same women having at least about four consecutive weeks of DHEA treatment may show an increase of about 1 day 3 embryo, and in the study summarized in FIG. 4, an increase of about 2 day 3 embryos. While the number of day 3 embryos produced slightly increased after at least 4 weeks of DHEA treatment, more significant increase occurs after at least about 4 months of DHEA treatment, and maximal increase may occur after at least about eight months of DHEA treatment.

V. Increase in the Number of Euploid Oocytes

DHEA may improve the number of euploid embryos and embryo transfers in women with diminished ovarian reserve (DOR). Pretreatment with DHEA, for at least about one month, preferably at least about four months, in women may increase oocyte and embryo quantity, egg and embryo quality, cumulative pregnancy rates, pregnancy rates with IVF and time to pregnancy.

DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA may have an effect after about 4 consecutive weeks. However, DHEA has a significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

The prevalence of aneuploidy in embryos, produced through IVF, from 27 consecutive IVF cycles in women with DOR who also had undergone preimplantation genetic diagnosis (PGD) was evaluated. Amongst those cycles, 19 had entered IVF without DHEA treatment and eight had received DHEA supplementation for at least four weeks prior to IVF start.

DHEA treatment may result in higher oocyte numbers (10.4±7.3 vs. 8.5±4.6) increasing from about 8.5 to about 10.4. A significantly larger number of DHEA treated IVF cycles (8/8, 100%) had at least one euploid embryo for transfer than in untreated cycles (10/19, 52.6%; Likelihood ratio, p=0.004; Fisher's Exact Test, p=0.026). Neither absolute numbers of euploid embryos after DHEA nor percentages of euploid embryos differed significantly in this case, however, between untreated and treated patients.

As women age, there is a substantial decline in euploidy rates in embryos produced. Thus, the increase in euploidy results in older women is dramatic evidence of the effectiveness of DHEA in improving embryo quality, and pretreatment with DHEA of women with DOR may significantly increase their chances for the transfer of at least one euploid embryo.

VI. Improvements to Ovarian Function

DHEA may have beneficial effects on ovarian function and oocyte and embryo quality. DHEA substitution may rejuvenate certain aspects of ovarian function in older ovaries. Since DHEA declines with age to a very significant degree, intraovarian DHEA deficiency may be causally related to the ovarian aging process.

Figure 5:
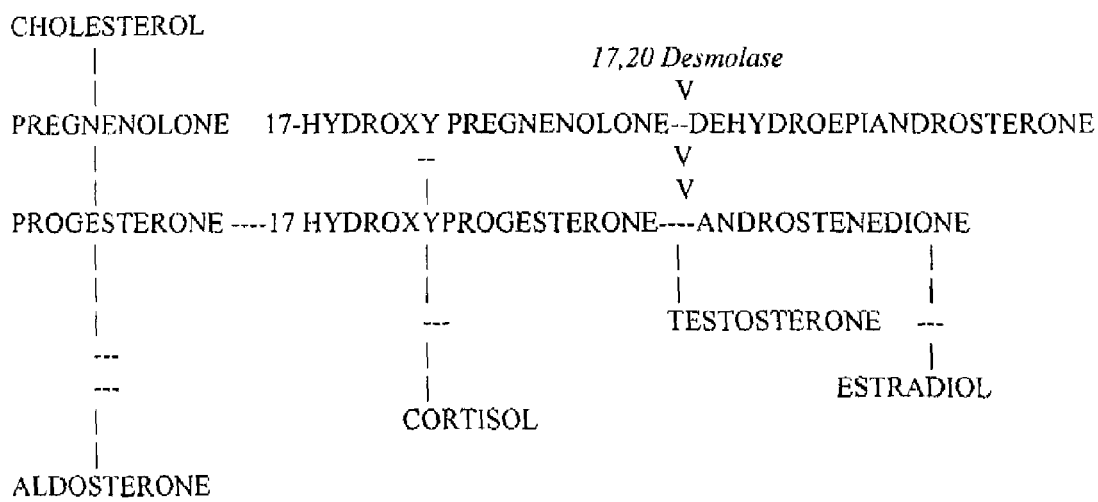
FIG. 5 is a chart showing chemical pathways of adrenal function.

FIG. 5 shows the pathways for normal adrenal function. As shown in FIG. 5, the adrenal enzyme 17,20-desmolase may be responsible for the conversion of 17-hydroxy pregnenolone into DHEA (and the conversion of 17-hydroxyprogesterone into androstenedione) which, based on the two-cell two-gonadotropin theory, may serve in the ovary as a precursor substrate for estradiol and androgens. A patient (Patient B), described further in Example 5 herein, with abnormal 17,20-desmolase (P450c17) function may have a hormone profile characterized by persistently low DHEA, androstenedione, testosterone and estradiol levels, but normal aldosterone and cortisol levels. Patient B exhibited some of the classical signs of prematurely aging ovaries which include ovarian resistance to stimulation, poor egg and embryo quality and prematurely elevated FSH levels.

The decrease in DHEA levels with advancing female age may be an inherent part of the ovarian aging process and may, at least in part, and on a temporary basis, be reversed by external DHEA substitution. This case demonstrates that low DHEA levels are, indeed, associated with all the classical signs of (prematurely) aging ovaries. While association does not necessarily suggest causation, the observed sequence of events in this patient supports the notion that low DHEA levels adversely affect ovarian function.

Patient B was initially thought to have largely unexplained infertility. Approximately 10 percent of the female population is believed to suffer from premature aging ovaries and this diagnosis is often mistaken for unexplained infertility (Nikolaou and Templeton, 2003, Gleicher N, 2005). Patient B later developed signs of prematurely aging ovaries and, finally, showed elevated FSH levels. In the time sequence in which all of these observations were made, Patient B followed the classical parallel premature aging curve (Nikolaou and Templeton, 2003; Gleicher N, 2005).

Once substituted with oral DHEA a reversal of many findings characteristic of the aging ovary was noted. DHEA treatment includes administering a dose of between about 50 mg/day and about 100 mg/day, preferably between about 60 mg/day and about 80 mg/day, and in one study about 75 mg/day to a human female. The DHEA dose could be administered as a single dose or as multiple doses over the course of a day. Particularly, the DHEA treatment may be administered to a premenopausal woman with diminished ovarian function. DHEA may have an effect after about 4 consecutive weeks. However, DHEA has a significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

After DHEA administration, Patient B's DHEA and dehydroepiandrosterone sulfate (DHEAS) levels normalized. In subsequent natural cycles an apparently normal spontaneous follicular response was observed, with normal ovulatory estradiol levels in a patient with persistently low estradiol levels before DHEA treatment.

DHEA deficiency may be a cause of female infertility and may be a possible causative agent in the aging processes of the ovary. The case study involving Patient B also presents further confirmation of the value of DHEA substitution whenever the suspicion exists that ovaries may be lacking of DHEA substrate. Since the process is familial (Nikolaou and Templeton, 2003), it is reasonable to assume that, like other adrenal enzymatic defects, 17,20-desmolase deficiency may occur either in a sporadic or in an inherited form. As both forms will result in abnormally low DHEA levels, both may lead to phenotypical expression as premature ovarian aging.

VII. Increase in Spontaneous Conceptions

Additionally, with DHEA treatment, there may be an unexpectedly large number of spontaneous conceptions in women waiting to go into an IVF cycle. DHEA treatment includes administering a dose of between about 50 mg/day and about 100 mg/day, preferably between about 60 mg/day and about 80 mg/day, and in one study about 75 mg/day to a human female. Particularly, the DHEA treatment may be administered to a premenopausal woman with diminished ovarian function. DHEA may have an effect after about 4 consecutive weeks. However, DHEA has a more significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

The DHEA treatment may be at least about 2 weeks before spontaneous conception occurs. In the population of women who are waiting to go into IVF, the spontaneous pregnancy rate is a fraction of about 1% per month. However, in the population of women who have been on DHEA treatment, there were 13 spontaneous pregnancies out of 60 women. As such, DHEA treatment increases spontaneous pregnancies in one study at least about 21 fold. This provides evidence that DHEA works not only in conjunction with gonadotropin stimulation of ovaries, but also without gonadotropin stimulation of ovaries.

VIII. Increase in Male Fetus Sex Ratio

A further effect of DHEA treatment is raising androgen levels in a female to increase the male fetus sex ratio. The gender of offspring may not be solely determined by chance. More highly androgenized female mammals give birth to more male offspring. Androgens, such as DHEA, may be utilized and an elevated baseline level of above about 250 ng/dl, preferably above about 350 ng/dl, may be sufficient. Infertile women with diminished ovarian reserve established a human model to investigate this theory. Data obtained from this model support an effect of androgenization on gender not through a follicular selection mechanism but rather through different mechanisms than previously theorized as evidenced by occurring after the preimplantation embryo stage.

Routine treatment protocol involves administering about 25 mg of micronized, pharmaceutical grade DHEA, TID, to a human female to uniformly raise levels of unconjugated DHEA above 350 ng/dl and, therefore, raise baseline testosterone. In six pregnancies spontaneously conceived, the distribution between female and male offspring was equal, at three and three, respectively. In contrast, in the remaining 15 offspring, which were products of pregnancies achieved through IVF, the distribution was 12 males and 3 females (p=0.035). Amongst women undergoing IVF and PGD, 53 embryos were analyzed from 17 IVF cycles, all having undergone ICSI. The gender distribution was not significantly skewed, with 27 being male and 26 female.

The data, demonstrating a strong trend towards both significance overall and significance (p=0.035) amongst IVF patients, suggest that gender determination may be influenced through hormone environments. The even distribution of gender (27 male and 26 female) in this group of patients argues against a selection process towards male, which is driven by the follicular environment, as has been previously suggested. The even distribution of gender in preimplantation embryos, seen in the control group, also speaks against such an effect.

The only remaining conclusion from the here presented data is that female androgenization affects gender selection after the preimplantation embryo stage and that, by definition, identifies the stage of androgenic influence on gender at or after implantation. All but one IVF cycles in study and control groups underwent ICSI, which requires the removal of granulose cells from the oocyte. One hypothesis is that such a removal may render the local environment more favorable towards the implantation of male than female embryos. A second hypothesis would suggest a similar effect, based on the difference in hormonal milieu in the luteal phase between IVF and spontaneous conception cycles, with the former uniformly supported by progesterone and the latter only sporadically, or not at all. The data provides evidence that the androgenization of females may increase the prevalence of male offspring, especially with IVF.

IX. Increase in Pregnancy Rates

An additional benefit of DHEA treatment is an unexpectedly high number of pregnancies in women, particularly in women with diminished ovarian function. DHEA supplementation is also associated with increased cumulative pregnancy rates and a shorter interval to pregnancy among women with evidence of decreased ovarian function entering evaluation and treatment for infertility.

DHEA treatment includes administering a dose of between about 50 mg/day and about 100 mg/day, preferably between about 60 mg/day and about 80 mg/day, and in one study about 75 mg/day to a human female. Further, DHEA may be administered in a time-release formulation, over the course of the day, or in a single dose. For example, the about 75 mg/day could be administered in a single dose of 75 mg or could be administered as 25 mg three times throughout the day. Particularly, the DHEA treatment may be administered to a premenopausal woman with diminished ovarian function. DHEA may have an effect after about 4 consecutive weeks. However, DHEA has a significant effect after about 8 weeks or about 2 months of administration, but its effect may continue to increase to about four months, and further may continue past four months of use. Specifically, DHEA treatment has a statistically significant effect after about at least 16 weeks or about at least 4 months of administration.

A case control study of 190 women over 30 years old with diminished ovarian function were studied between 1999 and December 2005. The study group included 89 patients with a mean age of about 41.6 who used supplementation of about 75 mg daily of oral, micronized DHEA for up to four months prior to entry into IVF. The control group composed 101 patients with a mean age of about 40.0 who received infertility treatment but did not use DHEA. The primary outcome was clinical pregnancy after the patient's initial visit.

Ovarian stimulation was identical for study and control groups and consisted of microdose agonist flare, followed by maximal dosage gonadotropin stimulation, using about 300-450 IU of FSH and about 150 IU of HMG. Study patients received DHEA continuously until a positive pregnancy test was obtained or until the patient dropped out of treatment.

Using a developed Cox proportional hazards model, the proportional hazards of pregnancy among women using DHEA was compared with the controls group. The results were that cumulative clinical pregnancy rates were significantly higher in the study group (25 pregnancies of 89 patients for 28% vs. 11 pregnancies of 101 patients for 11%; relative hazard of pregnancy in study group (HR 3.8; 95% CI 1.2 to 11.8; p<0.05)). Specifically, about 28% of the patients that received DHEA achieved a clinical pregnancy, and about 11% of the patients that did not receive DHEA achieved clinical pregnancy. As such, DHEA treatment increases the percentage of clinical pregnancies between about 130% and about 180%, preferably between about 140% and about 170%, and in one study about 157%. As such, DHEA treatment increases clinical pregnancies by at least about 150%.

Further, the results of this study show a statistically significant percentage of women that achieved clinical pregnancy only with DHEA treatment. See Table 8 in Example 7 herein. Table 8 shows 25 of 89 women in the DHEA treated group achieving clinical pregnancy, including 6 of 16 with no other treatment other than DHEA, and 6 of 9 women had intrauterine insemination (IUI/COH) but no IVF. About at least one-half of the patients (or at least about 50% of the patients), a total of 12 out of the 25 women (about 6 of 16 women with no other treatment, and about 6 of 9 women treated with intrauterine insemination) that established pregnancy did so spontaneously (i.e., with no IVF treatment). As such, DHEA treatment also increases the percentage of clinical pregnancies and significantly reduces the cumulative time to pregnancy.

Along with increased clinical pregnancies, women in this study, with a mean age of about 41.6, which were treated with DHEA had decreased miscarriage rates. Specifically, approximately 36% of the women in the control group (4 of 11 women) that did not receive DHEA had miscarriages and, in comparison, only approximately 20% of the women in the DHEA-treated group (5 of 25 women) had miscarriages. As such, DHEA treatment decreased the miscarriage rate between about 30% and about 60%, preferably between about 40% and about 50%, and in one study about 44%. DHEA treatment decreases the miscarriage rate by at least about ⅓, and preferably by at least about ½.

The data, described further herein, provides evidence that the DHEA supplementation improves spontaneous pregnancy rates, IVF pregnancy rates, cumulative pregnancy rates, and decreases the time interval to pregnancy.

X. Decrease in Miscarriage Rates

Supplementation with dehydroepiandrosterone (DHEA) as described herein below decreases miscarriage rates in infertile women with diminished ovarian reserve. DHEA administration, for an average of at least 2 months, decreases the miscarriage rate. DHEA treatment includes administering a dose of between about 50 mg/day and about 100 mg/day, preferably between about 60 mg/day and about 80 mg/day, and in one study about 75 mg/day to a human female. Further, DHEA may be administered in a time-release formulation, over the course of the day, or in a single dose. For example, the about 75 mg/day could be administered in a single dose of 75 mg or could be administered as 25 mg three times throughout the day. Particularly, the DHEA treatment may be administered to a premenopausal woman with diminished ovarian function. DHEA may have an effect after about 4 consecutive weeks. However, DHEA has a more significant effect after about 8 weeks or about 2 months of administration, but its effect may continue to increase to about four months, and further may continue past four months of use. Specifically, DHEA treatment has a statistically significant effect after at least about 16 weeks or at least about 4 months of administration, and preferably, DHEA treatment is administered for at least about 16 consecutive weeks or at least about 4 months.

About 85% of miscarriages are due to chromosomal abnormalities. As such, decreasing the miscarriage rates in women may indicate a decrease in aneuploidy rates.

After about at least two months of prior DHEA supplementation, the rate of clinical miscarriages in 73 pregnancies, established at two independent fertility centers in the United States (U.S.) and Canada, was compared to the national U.S. miscarriage rates, reported for in vitro fertilization (IVF) pregnancies for the year 2004.

The reduction in miscarriage rates in DHEA pregnancies at both centers were similar (15.0% and 15.2%) for a combined reduction in miscarriage rates of about 15.1%. The Mantel-Haenszel common odds ratio (and 95% CI) for the odds of miscarriage with DHEA supplementation, stratified by age, was significantly lower relative to the odds of miscarriage in the general U.S. IVF population [0.49 (0.25-0.94; p=0.04)]. Miscarriage rates after DHEA supplementation was lower at all ages than the 2004 US national averages, but the difference was more pronounced above age 35 years.

More specifically, DHEA treatment decreases the miscarriage rate for women under the age of about 35 between about 5% and about 25%, preferably between about 10% and about 20%, and in one study about 15.7%. DHEA treatment decreases the miscarriage rate for women under the age of about 35 by at least about one-seventh. Further, DHEA treatment decreases the miscarriage rate for women between the ages of about 35 and about 37 between about 50% and about 70%, preferably between about 55% and about 65%, and in one study about 60.8%. DHEA treatment decreases the miscarriage rate for women between the ages of about 35 and about 37 by at least about one-half. Also, DHEA treatment decreases the miscarriage rate for women between the ages of about 38 and about 40 between about 20% and about 40%, preferably between about 25% and about 35%, and in one study about 31.6%. DHEA treatment decreases the miscarriage rate for women between the ages of about 38 and about 40 by at least about ¼, and preferably by at least about ⅓. Additionally, DHEA treatment decreases the miscarriage rate for women between the ages of about 41 and about 42 between about 30% and about 60%, preferably between about 40% and about 50%, and in one study about 45.3%. DHEA treatment decreases the miscarriage rate for women between the ages of about 41 and about 42 by at least about ⅓, and preferably by at least about ½. Further, DHEA treatment decreases the miscarriage rate for women over the age of about 42 between about 40% and about 60%, preferably between about 45% and about 55%, and in one study about 50.1%. DHEA treatment decreases the miscarriage rate for women over the age of about 42 by at least about ½.

DHEA supplementation is associated with a significantly decreased miscarriage rate in women, especially above the age of about 35. DHEA treatment decreases the miscarriage rate for women over the age of about 35 by at least about 30% or at least about ⅓. Supplementation with DHEA reduces the miscarriage risk in this high risk population to levels reported for the general population.

This observation supports a beneficial effect of DHEA on aneuploidy rates. DHEA treated women with diminished ovarian reserve, who produce few embryos, only rarely qualify for preimplantation genetic screening. Data accumulation on embryo aneuploidy rates is, therefore, difficult. Because embryo aneuploidy rates are reflected in miscarriage rates, by demonstrating a remarkable reduction in miscarriage rates, there is circumstantial evidence that DHEA supplementation may reduce the rate of aneuploid embryos in infertile women.

XI. More on Decreasing Miscarriage Rates

Dehydroepinadrosterone (DHEA) supplementation improves pregnancy chances in women with diminished ovarian reserve (DOR) by possibly reducing aneuploidy. Since a large majority of spontaneous miscarriages are associated with aneuploidy, one can speculate that DHEA supplementation may also reduce miscarriage rates.

We retroactively compared, utilizing two independent statistical models, miscarriage rates in 73 DHEA supplemented pregnancies at two independent North American infertility centers, age-stratified, to miscarriages reported in a national U.S. in vitro fertilization (IVF) data base.

After DHEA supplementation the miscarriage rate at both centers was 15.1% (15.0% and 15.2%, respectively). For DHEA supplementation Mantel-Hanszel common odds ratio (and 95% confidence interval), stratified by age, was significantly lower, relative to odds of miscarriage in the general IVF control population [0.49 (0.25-0.94; p=0.04)]. Miscarriage rates after DHEA were significantly lower at all ages but most pronounced above age 35 years.

Since DOR patients in the literature are reported to experience significantly higher miscarriage rates than average IVF patients, the here observed reduction in miscarriages after DHEA supplementation exceeds, however, all expectations. Miscarriage rates after DHEA not only were lower than in an average national IVF population but were comparable to rates reported in normally fertile populations. Low miscarriage rates, comparable to those of normal fertile women, are statistically impossible to achieve in DOR patients without assumption of a DHEA effect on embryo ploidy. Beyond further investigations in infertile populations, these data, therefore, also suggest the investigations of pre-conception DHEA supplementation in normal fertile populations above age 35 years.

XII. Improvement in Ovarian Reserve

Our study presents the first objective evidence that supplementation with dehydroepiandrosterone (DHEA) of women with diminished ovarian reserve (DOR) improves ovarian reserve at all ages.

Our objective was to determine whether supplementation with dehydroepiandrosterone (DHEA) of women, suffering from diminished ovarian reserve (DOR), objectively improves ovarian reserve, based on anti-Miillerian hormone levels (AMH).

120 consecutive women, presenting with DOR were patients in this study. We administered DHEA to each patient to improve ovarian reserve.

DHEA administration, for an average of at least about 1 month, improves ovarian reserve. Preferably, DHEA administration lasts for between about 15 days to about 150 days, more preferably between about 25 days and 130 days, and in one study between about 30 days and about 120 days (mean 73 days±27 days).

DHEA administration also includes administering a dose of between about 50 mg/day and about 100 mg/day, preferably between about 60 mg/day and about 80 mg/day, and in one study about 75 mg/day to a human female. Further, DHEA may be administered in a time-release formulation, over the course of the day, or in a single dose. For example, the about 75 mg/day could be administered in a single dose of about 75 mg or could be administered as about 25 mg three times throughout the day. Particularly, the DHEA treatment may be administered to a premenopausal woman with diminished ovarian function. DHEA may have an effect after about 4 consecutive weeks. However, DHEA has a more significant effect after about 8 weeks or about 2 months of administration, but its effect may continue to increase to about four months, and further may continue past four months of use. Specifically, DHEA treatment has a statistically significant effect after at least about 16 weeks or at least about 4 months of administration, and preferably, DHEA treatment is administered for at least about 16 consecutive weeks or at least about 4 months.

Our main outcome measure was AMH levels in relationship to DHEA supplementation over days of DHEA supplementation using linear regression and, in longitudinal evaluation, by examining the interaction between days of DHEA treatment and pregnancy success in respect to changes in AMH levels.

Our results were that AMH levels significantly improved after DHEA supplementation over time (p=0.002). Age (p=0.007) and length of treatment (p=0.019) were independently associated with increasing AMH. Women under about age 38 years demonstrated higher AMH levels and improved AMH proportionally more than older females. Longitudinally, AMH levels improved by approximately 60 percent from 0.22±0.22 ng/ml to 0.35±0.03 ng/ml (p<0.0002).

Women who reached IVF experienced a 23.64% clinical pregnancy rate. Those who conceived improved AMH significantly more than women who did not (p=0.001).

In sum, DHEA supplementation significantly improves ovarian reserve with DOR. Additionally, improvement increases with longer DHEA supplementation and is more pronounced in younger women under age about 38 years.

XIII. Age-specific anti-Müllerian Hormone (AMH): Utility of AMH at Various Ages

Anti-Müllerian hormone (AMH) is increasingly recognized for better specificity in reflecting ovarian reserve (OR) than follicle stimulating hormone (FSH). Like FSH, AMH, however changes with advancing female age. Normal levels should, therefore, vary at different female ages.

We, therefore, established so-called age-specific (as-) AMH levels in four age groups and investigated whether oocytes number, obtained at IVF, differed based on whether a patient's as-AMH was in as-range, below it or above it.

AMH demonstrated, once again, its better specificity in comparison to FSH by showing narrower normal ranges at all ages. Moreover, as-AMH allowed for discrimination of oocytes yields at all ages. This study confirms AMH as a better reflection of OR in comparison to FSH. Moreover, AMH has the additional advantage of not only being able to predict diminished ovarian reserve (DOR) and low oocytes yields but also high oocytes yield, risk for polycystic ovarian syndrome and ovarian hyperstimulation. It, therefore, appears particularly suitable in the investigation of OR in younger women.

Abstract of Age-Specific Anti-Müllerian Hormone

We assessed whether age-specific (as-) cut offs for anti-Müllerian hormone (AMH) have higher specificity in reflecting ovarian reserve (OR) than non-age-specific (nas-) AMH values. as-AMH values were defined in 778 consecutive infertility patients by establishing as-95% confidence intervals (CI) of AMH at various ages.

Ocytes yields were then compared at various ages in women with normal and abnormal as-AMH. AMH decreased with advancing female age (p<0.0001), differed significantly in each of four selected age categories (p<0.001) and ranges of as-AMH were at all ages narrower than for as-FSH. In 288 women who reached in vitro fertilization (IVF), as-AMH, after adjustment for age, was statistically predictive of oocytes yields if abnormally low (<95% CI) or high (>95% CI). Normal and abnormally elevated as-AMH combined, demonstrated 5.4-times (95% CI 4.1-6.8) greater oocytes yields than abnormally low as-AMH. Like as-FSH, as-AMH better reflects OR than nas-ovarian reserve testing. In contrast to as-FSH, as-AMH, however, defines risk towards diminished OR (DOR) and high oocytes yields (i.e., potential hyperstimulation syndrome, OHSS) and, therefore, may be a particularly useful OR test in younger women in whom DOR is most frequently overlooked, and who are at highest risk for OHSS. See at least Example 10, below.

XIII. Review, Summary and New Findings on Dehydroepiandrosterone (DHEA) Supplementation in Women with Diminished Ovarian Reserve (DOR)

A. Overview

Context: As women above age 40 have become the most rapidly growing age group giving birth, treatment of diminished ovarian reserve (DOR) has assumed GREATER importance. Dehydroepinadrosterone (DHEA) supplementation is increasingly utilized for this purpose. A review of published literature is presented.

Evidence Acquisition: PubMed, Cochrane and Ovid Medline were searched between 1995 and 2009 under the following strategy: [<dehydroepiandrosterone or DHEA or androgens or testosterone> and <ovarian reserve or diminished ovarian reserve or ovarian function>]. Bibliographies of relevant publications were further explored for additional relevant citations.

Evidence Synthesis: In absence of prospectively randomized studies, other study formats offer evidence that DHEA supplementation of women with DOR to significant degrees improves ovarian function parameters, increases pregnancy chances and, likely by reducing aneuploidy, reduces miscarriage rates. DHEA effects increase with length of supplementation.

Conclusions: DHEA effects point towards a revised concept of ovarian aging, which suggests that medications may restore aged ovarian environments towards "younger ages," allowing recruited primordial follicles to mature at improved environmental conditions. Primordial oocytes, therefore, likely do not age, as currently believed, but ovarian environments do. DHEA may, therefore, be only the first, amongst other future drugs, capable of, at least partially, restoring ovarian environments for folliculogenesis in women with DOR, in the process reducing aneuploidy, improving pregnancy chances and reducing miscarriages.

B. Historic Developments

Peter R. Casson and associates, at John E. Buster's group (Baylor Medical College, Houston, Tex.) were the first to suggest therapeutic benefits from dehydroepiandrosterone (DHEA) supplementation in women with diminished ovarian reserve (DOR). This group of investigators had a long-standing interest in DHEA and contributed many important, initial observations, which often were not immediately recognized for their potential clinical significance.

They first reported that micronized DHEA offers the potential of postmenopausal steroidal replacement, adjunctive to estrogen. In adrenal and ovarian steroidogenesis, DHEA is an intermediate product in the conversion of cholesterol to the sex hormones, testosterone and estradiol. They, however, demonstrated that in postmenopausal women this conversion is not symmetrical and favors androgens. While testosterone after DHEA supplementation increases, estradiol remains low. In further exploring androgen deficiency in menopause, they then demonstrated that DHEA has immunomodulatory effects, an observation now well recognized and therapeutically explored in treating autoimmune diseases.

The same group later demonstrated that vaginally administered DHEA, while delivering equivalent hormone, substantially diminishes bioconversion in comparison to oral micronized product. They followed up by showing that abnormally low DHEA secretion is potentiated by ovarian hypertstimulation, an observation to be discussed in more detail below.

Returning to DHEA as potential postmenopausal steroid replacement, they demonstrated that DHEA was well tolerated and increased IGF-1 levels. Recurrent themes of their research were the need to address adrenal cortical changes in aging women, and compensating with DHEA supplementation.

This work led to the above noted case series of women with poor response to ovarian stimulation with gonadotropins, in which Casson and associates reported improvements in ovarian response after DHEA supplementation. Their rational for this study was the previously observed increase in IGF-1 after DHEA supplementation (8). Since growth hormone had been suggested to improve oocytes yields via IGF-1, they speculated that DHEA may be able to achieve similar effects.

Like other achievements by this group, this small case series went largely unnoticed. Even the authors, themselves, did not further follow up. It was left to a 43 year old patient at our center, years later, to rediscover the paper when searching the literature for remedies that may help her overcome severe DOR and resistance to ovarian stimulation. She in a first in vitro fertilization (IVF) cycle, for the purpose of fertility preservation, had produced only one egg and one embryo, and had been advised to consider oocytes donation.

The patient, an attorney and banker without medical training, based on review of the literature, identified various potential remedies to improve her response to stimulation. She chose DHEA, as she later told us, because it was the only medication she could purchase without prescription and, therefore, without our knowledge. In the United States (U.S.), despite being a mild androgen, DHEA is, paradoxically, considered a food supplement and available over the counter, without prescription. See at least Example 1.

To our surprise (and unaware of her DHEA supplementation), the patients in her second IVF cycle produced three oocytes and three embryos of excellent quality. We, therefore, no longer refused further cycles. She underwent a total of nine consecutive IVF cycles, and we reported her extraordinary experience.

Figure 19:
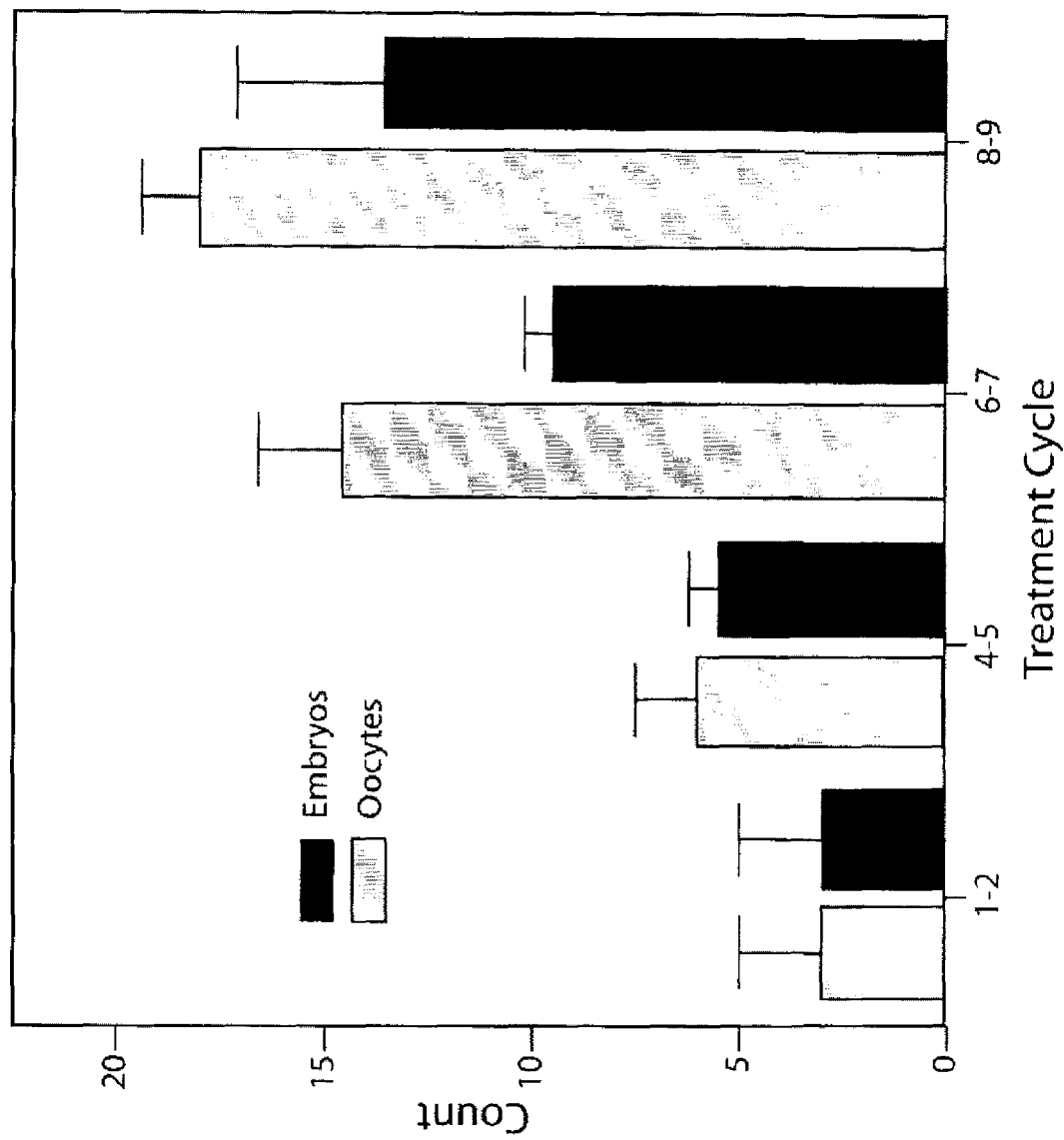
FIG. 19 is a figure showing oocyte and embryo counts in an index patient.

FIG. 19 is a graph showing oocyte and embryo counts in an index patient. The patient underwent nine consecutive IVF cycles and increased oocytes and embryo yields from cycle to cycle, starting with one egg and embryo, respectively, and ending up with 17 oocytes and 16 embryos in her ninth cycle. Gonadotropin stimulation was reduced in her last cycle for concerns about possible ovarian hyperstimulation. The patients advised us of her DHEA supplementation only after her sixth cycle.

In recognition of this patient's contribution to the DHEA research at our center, going forward, she will be designated as the center's index patient. As FIG. 19 demonstrates, she from cycle to cycle increased oocyte and embryo yields. In her ninth cycle, by now 44 years old, her gonadotropin dosage had to be reduced because of concerns about hyperstimulation. In that cycle, 17 oocytes were retrieved and 16 embryos were produced. To assess potential pregnancy chances better, preimplantation genetic diagnosis (PGD) was performed to determine the degree of aneuploidy in her embryos. Amongst 10 embryos nine were reported aneuploid. The one euploid embryo was cryopreserved.

It was not until after the patient's sixth IVF cycle that she made us aware of her DHEA supplementation. By that point we were wondering how a woman in her mid-40s, from cycle to cycle, could improve oocyte and embryo yields to such a degree. Once informed about the DHEA supplementation, we initiated a structured clinical investigation of DHEA supplementation in women with DOR.

An attempt at prospectively randomizing patients had to be abandoned for lack of recruitment. Women with DOR almost uniformly refused randomization (trial number NCT00419913). Considering that such patients often have limited time left to conceive, this should not surprise. European colleagues, initially convinced they would be able to recruit better, attempted randomization in a multi-center effort, in cooperation with our Center. This trial involved IVF centers in Austria, Switzerland and the Czech Republic, and also had to be abandoned for lack of recruitment. As of this point no prospectively randomized study of DHEA supplementation in women with DOR has been reported. Best available evidence, therefore, so far relies on other study formats than prospectively randomized trials. Available DHEA data, as of this point, are limited to observational, cohort and case control studies. Those are reviewed in the following section.

C. Reported Clinical Experiences

Increase in Oocytes and Embryo Yields

Casson and associates, in their initial report, did not outright suggest a DHEA benefit on DOR. Instead, they claimed that DHEA supplementation may augment ovarian stimulation with gonadotropins in poor responders and results in improved oocytes yields. This conclusion was reached in six IVF cycles based on investigation of only five proven poor responders, under the age 41 years, and with baseline follicle stimulating hormone (FSH) under 20 mIU/ml. After receiving 80 mg of micronized DHEA for two months, all study subjects demonstrated improved responsiveness in comparison to a prior unsupplemented cycle, characterized by increased peak estradiol and improved peak estradiol/gonadotropin dosage ratios. In addition, one patient delivered a twin pregnancy.

Likely due to the small study size and the chosen study format, this paper received no follow up attention. The next published report on DHEA supplementation appeared a full five years later and described our experience with the earlier noted index patient. Like Casson et al, we, too, were, first and foremost, impressed by the observed improvement in oocytes yields, which seemed far greater than initially reported by the Baylor group. Indeed, considering the length of observation and number of repeat cycles in our index patient (FIG. 19), we felt that the longitudinal observation of this single patient offered even stronger support for a positive DHEA effect on oocytes numbers. A statistical error, like return to median, in our observation seemed less likely than in an observational study, where patients, in only two observations, served as their own controls.

We were also impressed by the continuous improvement in oocyte (and embryo) numbers with increasing length of DHEA supplementation and speculated about possible causes: DHEA over time could have cumulative benefits and/or could have synergistic effects with gonadotropin stimulation, which our index patient underwent practically month after month in pursuit of nine consecutive cycles. Cumulative effects over time would suggest a DHEA effect on follicular recruitment cycles in their total length, while synergistic effects with gonadotropin stimulation appeared a possibility based on the Baylor group's report that gonadotropins augment adrenocortical DHEA (sulfate) secretion.

More importantly, however, we started to view DHEA supplementation no longer as just a potential tool in overcoming ovarian resistance to stimulation and increase oocytes yields, but as a potential remedy to positively affect ovarian reserve (OR).

OR is a widely held concept, which assumes that a woman's OR is reflective of chances for conception. In principle, OR is defined by the size of the remaining follicular pool within ovaries but, in parallel, also assumes a qualitative component.

The new focus on OR represented a significant conceptional change because it suggested that DHEA may not only impact oocyte and embryo numbers but also oocyte and embryo quality. It was this consideration, which led towards investigations of egg and embryo quality and, ultimately, of pregnancy success.

Improvements in Oocytes and Embryo Quality

The first 25 DOR patients supplemented with DHEA at our center, in paired analysis of pre- and post-DHEA cycles, once more confirmed statistically significant increases in oocytes and embryo numbers. This study, however, for the first time, also demonstrated that DHEA improves to significant degrees embryo quality parameters, including embryo grades and average embryo scores. Most importantly, however, this study for the first time presented evidence that DHEA significantly increases transferred embryo numbers.

Since in women with severe DOR the number of embryos available for transfer is almost always inadequately low, that DHEA could improve embryo transfer numbers suggested that DHEA also may positively affect pregnancy rates.

FIG. 17 is a table showing comparisons of pre- and post-DHEA cycles in 25 women with DOR*. *=25 patients were evaluated in their respective IVF cycle outcomes pre- and post-DHEA. This study design potentially biases outcome against positive DHEA effects since patients who entered DHEA supplementation after a prior failed IVF cycle, quite obviously, reflected, in view of their prior IVF treatment failure a negatively selected patient population. Pre- and post DHEA cycles occurred at ages 39±0.8 and 40.4±0.8 years, respectively, also mildly biasing the study against positive DHEA findings. Post-DHEA patients were on supplementation 17.6±2.13 weeks by time of second IVF cycle. The uniformity of results of this study, all suggesting quantitative and qualitative IVF outcome improvements (FIG. 17), therefore, strongly encouraged the center's continuous research efforts.

Improvements in Pregnancy Rates

Aside from abstracts, the next publication was a case controlled study involving 89 DOR patients, prior to IVF, for up to four months, supplemented with DHEA. One-hundred-and-one infertile DOR patients, without DHEA supplementation, served as historical controls. The primary purpose of this study was to assess potential effects of DHEA on pregnancy rates.

Despite significantly older age (41.6±0.4 vs. 40.0±0.4 years) of DHEA patients, this study for the first time demonstrated that DHEA improves time to pregnancy and overall pregnancy chances. Cumulative clinical pregnancies after DHEA (28.1%) were significantly higher than in controls (10.9%; 95% CI 1.2-11.8; $p<0.05$). These results were obtained even though controls were prognostically a more favorable patient group.

They produced more oocytes ($p<0.01$), normal day-3 embryos ($p<0.05$) and even received more embryos at time of transfer ($p<0.05$). Clinical pregnancies were, yet, still significantly higher amongst DHEA supplemented women.

To us this observation suggested primacy of egg and embryo quality over egg and embryo quantity and, going forward, this paradigm became a guiding principle in how to prepare and stimulate DOR patients for IVF.

Expanded and successful DHEA utilization world-wide is also documented by quite a number of published abstracts Likely the largest experience has been accumulated in Toronto, Canada, by Ed Ryan and his team, who report significantly improved clinical pregnancy rates in hundreds of IVF and insemination cycles, using varying ovarian stimulation protocols (Ryan E, Personal communication, 2009).

In cooperation with Robert F Casper's group at Toronto's Mount Sinai Hospital, they recently reported on 47 patients with prior clomiphene citrate failures who were supplemented with 75 mg daily of DHEA for at least 60 days prior to inseminations, with stimulation by either clomiphene citrate or letrozole in combination with FSH. Controls were 46 women, matched by age and baseline FSH without DHEA supplementation. DHEA patients demonstrated significantly higher antral follicle counts, significantly improved pregnancy rates (29.8 vs. 8.7%; CI 1.3-14.8) and live births (21.3% and 6.5%, respectively), numbers remarkably similar to those reported by our group.

We are also aware of, still unpublished data sets, from Israel, Turkey and Japan, which all uniformly suggest treatment outcome improvements after DHEA supplementation. Conversely, we are unaware of any data sets that failed to demonstrate such benefits.

Premature Versus Physiologic DOR

With an increasing size data set, it became possible to separate DOR patients into women with age-dependent DOR and younger females with so-called premature ovarian aging (POA). Based on age-specific FSH, we defined POA as abnormally elevated FSH under age 40 years, and considered every woman above age 40 to automatically suffer from physiologic, age-dependent DOR.

Figures 20A, 20B:
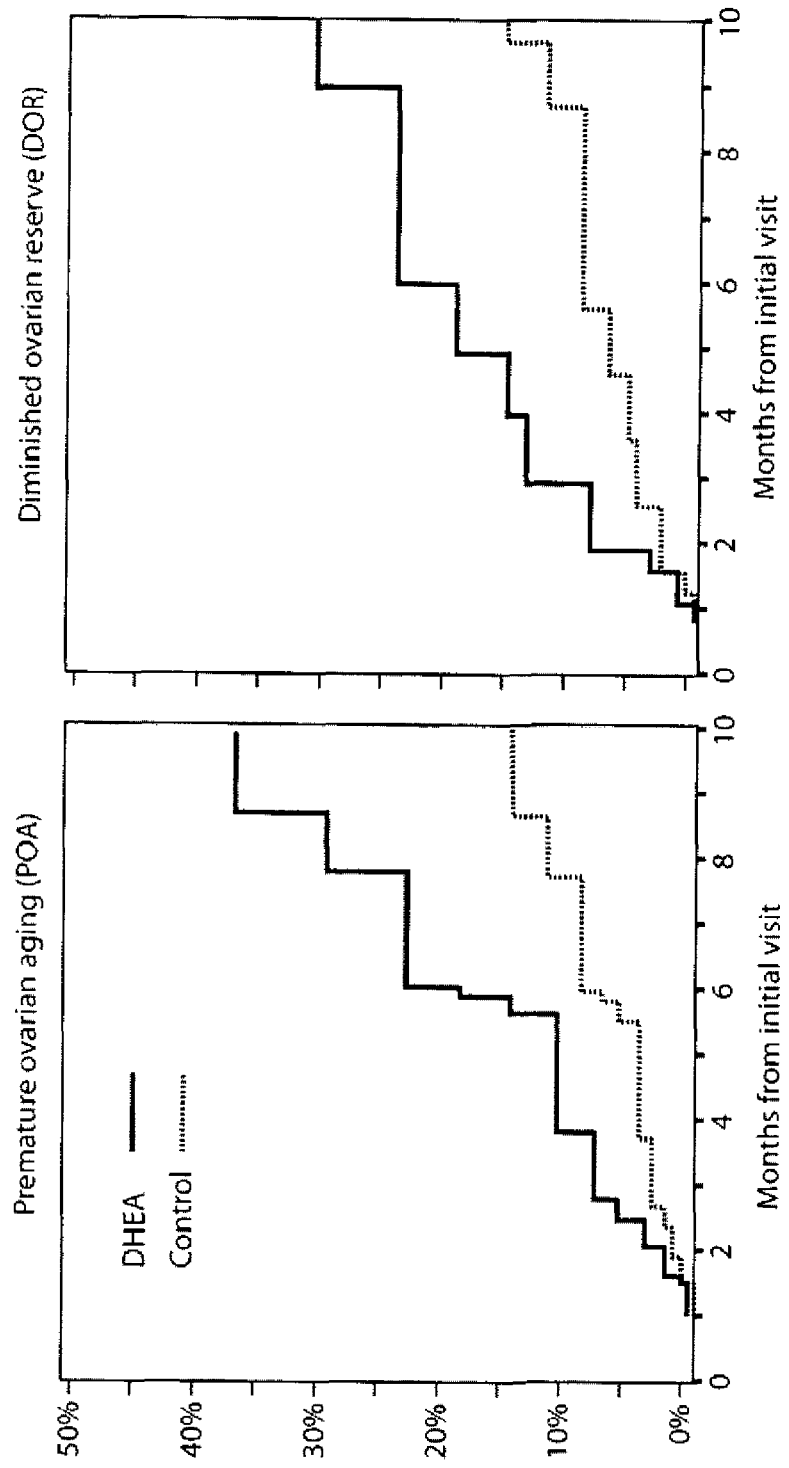
FIG. 20A is a graph showing cumulative pregnancy rates in women with DOR with and without DHEA supplementation—premature ovarian aging (POA). The figure demonstrates cumulative pregnancy rates in DHEA and control patients with POA.
FIG. 20B is a graph showing cumulative pregnancy rates in women with DOR with and without DHEA supplementation—diminished over reserve (DOR). The figure demonstrates cumulative pregnancy rates in women above age 40 years.

FIG. 20A is a graph showing cumulative pregnancy rates in women with DOR with and without DHEA supplementation—premature ovarian aging (POA). The figure demonstrates on the left side cumulative pregnancy rates in DHEA and control patients with POA (for definition see text). Both patient population demonstrate similar treatment benefits for DHEA, though POA patients appear to have a slight pregnancy advantage, further confirmed in later data presentations. FIG. 20B is a graph showing cumulative pregnancy rates in women with DOR with and without DHEA supplementation—diminished over reserve (DOR). The right side of the figure demonstrates cumulative pregnancy rates in women above age 40 years.

DHEA supplementation proved similarly effective in both groups, though POA patients, as FIG. 20 demonstrates, do mildly better. The figure also demonstrates that beneficial effects of DHEA increase with increasing length of DHEA supplementation since discrepancies in cumulative pregnancy rates between DHEA and control patients increase with time.

These data confirm observations originally made in the index patient: DHEA effects are relatively quick but do not peak for months. This led us to require at least six weeks of DHEA supplementation prior to IVF cycle starts. We, however, if clinical circumstances allow, do not hesitate to extend this time period, especially in younger women, to three to four months. Considering the severity of DOR in DHEA supplemented patients, we observed surprising numbers of spontaneously conceived pregnancies during this waiting period.

Premature Ovarian Failure (POF)

Women who suffer from POA/DOR are distinct from women in outright premature ovarian failure (POF), or primary ovarian insufficiency (POI), an acronym recently increasingly applied to this condition. As above summarized, until recently, DHEA was only investigated in POA/DOR patients. At our center all successfully treated patients had baseline FSH levels below 40.0 mIU/ml.

Mamas and Mamas, from Athens, Greece, however, recently reported a case series of five alleged POF/POI patients, who succeeded in spontaneously conceiving after DHEA supplementation.

While intriguing in concept, this report has to be viewed with caution. Not only is this case series very small, but three of the five reported patients do not qualify for the diagnosis of POF/POI under standard definitions and, likely, resemble previously described POA/DOR patients.

In a brief review Mamas and Mamas more recently reiterated their claim, though without much additional detail. In a personal communication, one of the authors advised us that they observed additional spontaneous pregnancies in DHEA supplemented POF/POI patients (Mamas L, Personal communication, ESHRE Annual Meeting, Amsterdam, The Netherlands, July 2009). Our center has registered and initiated a prospectively randomized study of DHEA supplementation in POF/POI patients (trial number NCT00948857) but has so far, in a very small number of patients, not yet observed a pregnancy.

This study welcomes collaborating centers and/or referrals of patients. Study participation is free of charges to patients.

Effects on Embryo Ploidy, Miscarriage Risk and Live Birth Rates

We noted earlier that our index patient gave us in her last IVF cycle the opportunity to investigate 10 of her embryos for aneuploidy. Amongst those, only one was found euploid. Recognizing current limitations to accurate preimplantation genetic screening (PGS), we have had limited opportunities to perform PGS in women with DOR. They usually produce only small embryo numbers and, in our opinion, therefore, are not qualified for PGS.

In a small pilot study we, however, in 2007 noted that 100 percent of DHEA treated but only 53 percent of control IVF cycles gave us at least one euploid embryo (p<0.05). These results were obtained, even though DHEA treated patients were older than controls and, therefore, expected to have more aneuploidy.

Though this difference reached statistical significance, the number of cases available for investigation was too small to reach a statistically robust enough conclusion that DHEA, indeed, beneficially affects embryo ploidy. Because larger patient numbers appeared unlikely in the foreseeable future, we decided to seek alternatives to explore this question further. The close statistical association between embryo aneuploidy and spontaneous pregnancy loss appeared suited for further investigation. An opportunity presented itself when Ed Ryan, MD (Toronto, Canada), unannounced, offered his center's DHEA data for joint analysis. Combined, our two centers had produced large enough post-DHEA pregnancy numbers to allow for a statistically robust analysis of miscarriage rates. Since approximately 80 to 85 percent of all miscarriages are the consequence of chromosomal abnormalities, we concluded that a positive DHEA effect on ploidy should be statistically reflected in lower miscarriage rates.

A since published study, indeed, confirmed this hypothesis. DHEA pregnancies demonstrated significant reduction in spontaneous pregnancy loss in comparison to national U.S. IVF pregnancy rates. Depending on statistical method utilized, the observed decline in miscarriages was in the range of 50 to 80 percent.

Figure 21:
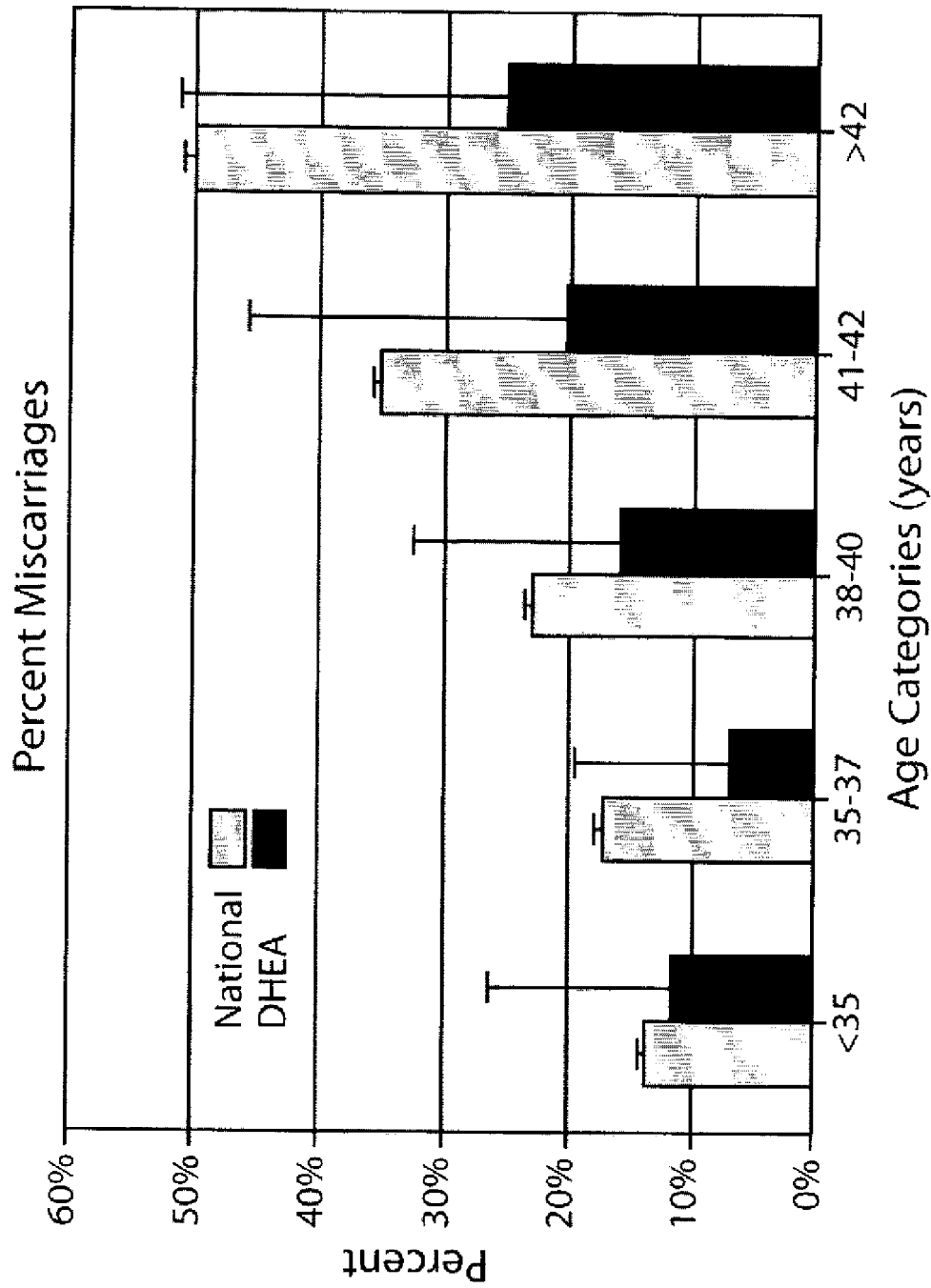
FIG. 21 is a graph showing age-stratified miscarriage rates in DHEA supplemented DOR patient in comparison to national U.S. IVF pregnancies.

Additional observations even further strengthened these findings: [1] Miscarriage rates in Toronto and New York were practically identical (15.2 and 15.0%, respectively). [2] In contrast to DHEA patients, who uniformly suffered from DOR, the U.S. national IVF registry reflects a DOR diagnosis in only a small minority of patients. Since DOR patients demonstrate significantly higher miscarriage rates than other infertility patients, the national control population was strongly biased against discovery of a DHEA effect on miscarriages. [3] The observed combined miscarriage rate of 15.1 percent in DHEA pretreated patients mimics spontaneous miscarriage rates reported in normal, fertile populations. [4] The DHEA benefit on miscarriage rates was small under age 35 years, but, after that age, progressively increased (FIG. 21 is a graph showing age-stratified miscarriage rates in DHEA supplemented DOR patient in comparison to national U.S. IVF pregnancies. DHEA pretreated patients demonstrated significantly lower miscarriage rates at all ages. The difference was, however, relatively small under age 35 years and progressively increased after that age.).

All of these observations offer strong additional support for the assumption that DHEA, to a significant degree, beneficially affects age-related miscarriage rates. Such large effects on miscarriage rates are unachievable unless DHEA beneficially affects ploidy. We, therefore, based on the earlier PGD- and this miscarriage-study, are now convinced that DHEA beneficially affects embryo ploidy and that it does so increasingly successfully with advancing female age.

Figure 22:
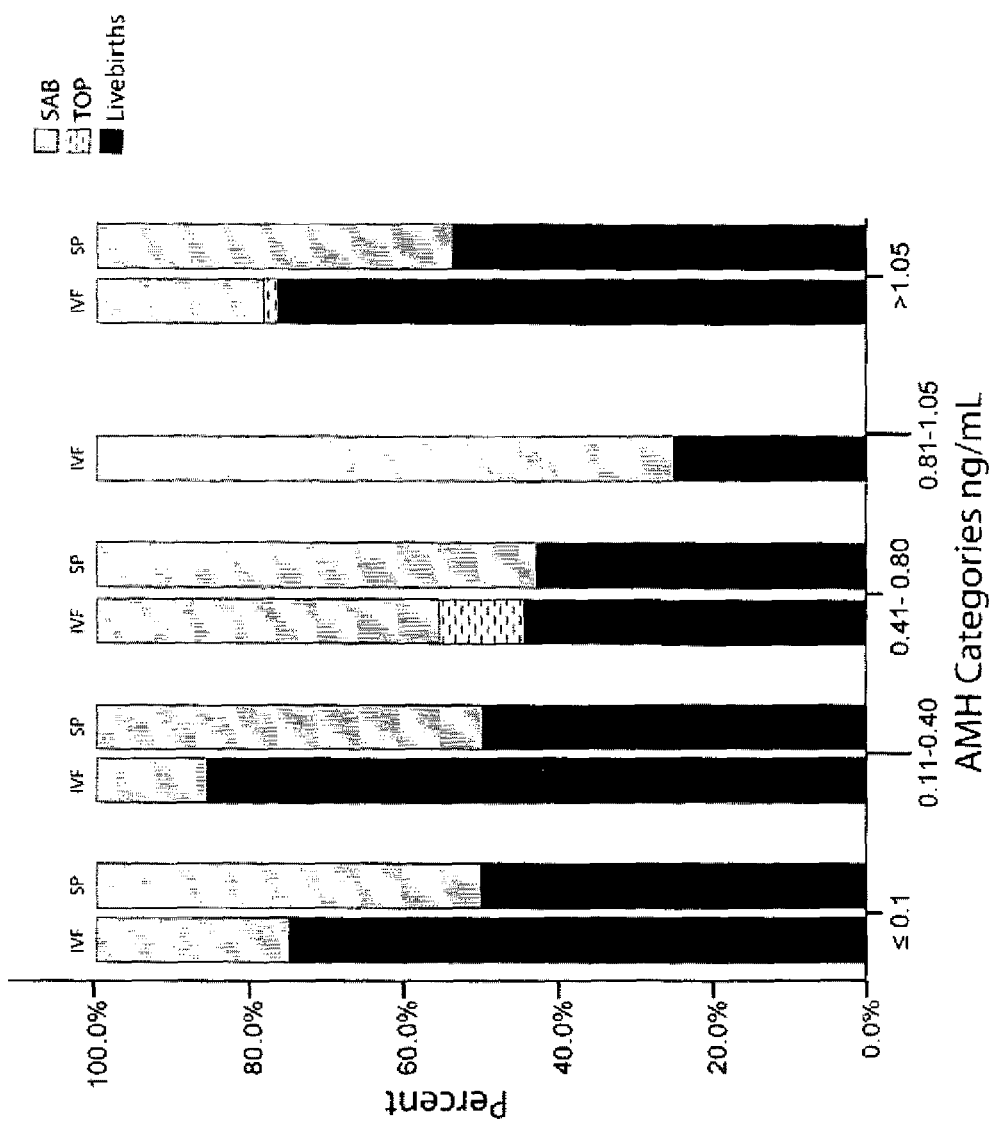
FIG. 22 is a graph showing spontaneous pregnancy loss in spontaneous and IVF pregnancies at various AMH levels.

Another study from our center further supports these conclusions (FIG. 22). FIG. 22 is a graph showing spontaneous pregnancy loss in spontaneous and IVF pregnancies at various AMH levels. The figure depicts at various AMH levels in the left column IVF pregnancies (IVF), as previously reported (26), and in the right column spontaneously conceived pregnancies (SP). Each column represents 100% of all pregnancies established, separated for live births (black section), voluntary termination of pregnancy (TOP; usually for aneuploidy) and spontaneous miscarriages (SAB). The figure demonstrates that at very low AMH levels (<0.40 ng/mL) and at AMH≧1.06 ng/mL, IVF pregnancies led to significantly higher live birth rates than spontaneously conceived DHEA pregnancies. Lowest pregnancy and live birth rates were observed with IVF and spontaneously between AMH 0.41-1.05 ng/mL, with no spontaneous DHEA pregnancies at all at AMH 0.81-1.05 ng/mL. While in IVF pregnancies miscarriage rates were clearly reduced at very low and at higher AMH, miscarriages appeared unaffected (~50%) in spontaneously conceived pregnancies.

In that study (FIG. 22), we investigated live birth rates after IVF at extremely low anti-Müllerian hormone (AMH) levels and were surprised how low miscarriage rates were between non-detectable levels of AMH and 0.4 ng/mL. Losses then increased between AMH 0.41-1.05 ng/mL to over 50 percent, the expected rate in DOR patients, only to fall, once again, to very low levels above AMH 1.05 ng/mL.

Since all investigated patients/pregnancies had been pretreated with DHEA, it seems likely that the observed very low miscarriage rates below AMH 0.4 and above 1.05 ng/mL were the consequence of DHEA supplementation. These results, however, raised the question why such a DHEA effect would not also be seen at AMH levels 0.41-1.05 ng/mL?

Since submission of those IVF pregnancy data, we had the opportunity to investigate 39 spontaneous pregnancies, conceived while on DHEA supplementation. FIG. 22 demonstrates miscarriage rates in these patients in comparison to above noted IVF pregnancies. As the figure demonstrates, spontaneous DHEA pregnancies in DOR patients, at all low AMH levels, experience almost identically high miscarriage rates (around 50 percent). Spontaneous DHEA conceptions, thus, do not appear to benefit from DHEA effects on miscarriage rates to the same degree as IVF pregnancies.

This observation suggests two possible explanations: Synergistic gonadotropin stimulation may contribute to the reduction in miscarriage rates observed with DHEA supplementation or women who spontaneously conceived simply did not have equal length of DHEA exposure as IVF patients. We are currently investigating the two explanations.

The possibility of synergistic gonadotropin and DHEA effects is supported by reanalysis of the Toronto groups' previously noted insemination cycles, stimulated with a clomiphene citrate/letrozole and FSH protocols. Calculating miscarriage rates, we noted rates of 28.5% and 25.3%, respectively, for DHEA and control pregnancies, both rates significantly higher, than the 15.2 percent previously reported by Ryan's program, mostly involving IVF cycles. Since patients in this study mostly received clomiphene citrate and/or letrozole, these data potentially favor a synergistically beneficial effect on ovaries between DHEA and gonadotropin stimulation, in line with earlier suggestions by the Baylor group. Final conclusions await, however, further investigations.

Predicting the Effectiveness of DHEA

FIG. 22 also, once again, suggests special ovarian circumstances at AMH levels 0.41-1.05 n/mL: between AMH 0.41-0.80 the trend in spontaneous and IVF DHEA pregnancies is towards more miscarriages. Between AMH 0.81-105 ng/mL, remarkably, no spontaneous pregnancies were registered at all. Combined, these observations suggest that at OR level between AMH 0.41-1.05 ng/mL beneficial DHEA effects on OR may be less pronounce than at lower and higher AMH levels. Why that is, remains to be determined and is currently under investigation.

Our data on women with severe DOR, thus, suggest that AMH levels demonstrate a certain degree of predictability in regards to DHEA utilization.

FIG. 18 summarizes how AMH levels relate to chance of conception and live births in IVF pregnancies with DHEA supplementation.

FIG. 18 is a table showing effectiveness of DHEA supplementation in IVF pregnancies based on AMH.

As the figure demonstrates, under DHEA supplementation, even in absence of detectable AMH, an approximate 5 percent pregnancy chance per IVF cycle can be obtained. Even more remarkably, miscarriage rates at undetectable AMH are exceedingly low, thus practically equating clinical pregnancy and live birth rates. These outcomes remain the same up to AMH 0.4 ng/mL, at which point clinical pregnancy chances per treatment cycle approximately double. Despite higher pregnancy rates, live birth rates remain, however, unchanged since between AMH 0.41-1.05 ng/mL spontaneous pregnancy wastage is surprisingly high. Above those AMH levels pregnancy chances greatly improve and miscarriage risk recedes once again to much lower levels.

AMH 1.05 ng/mL, thus, represents for DOR patients under DHEA supplementation a distinct separation point in regards to live birth chances: Up to AMH 1.05 ng/mL the chance of live birth per treatment cycle is only approximately 5 percent. Above that AMH level, live births chances are significantly improved.

Figure 23:
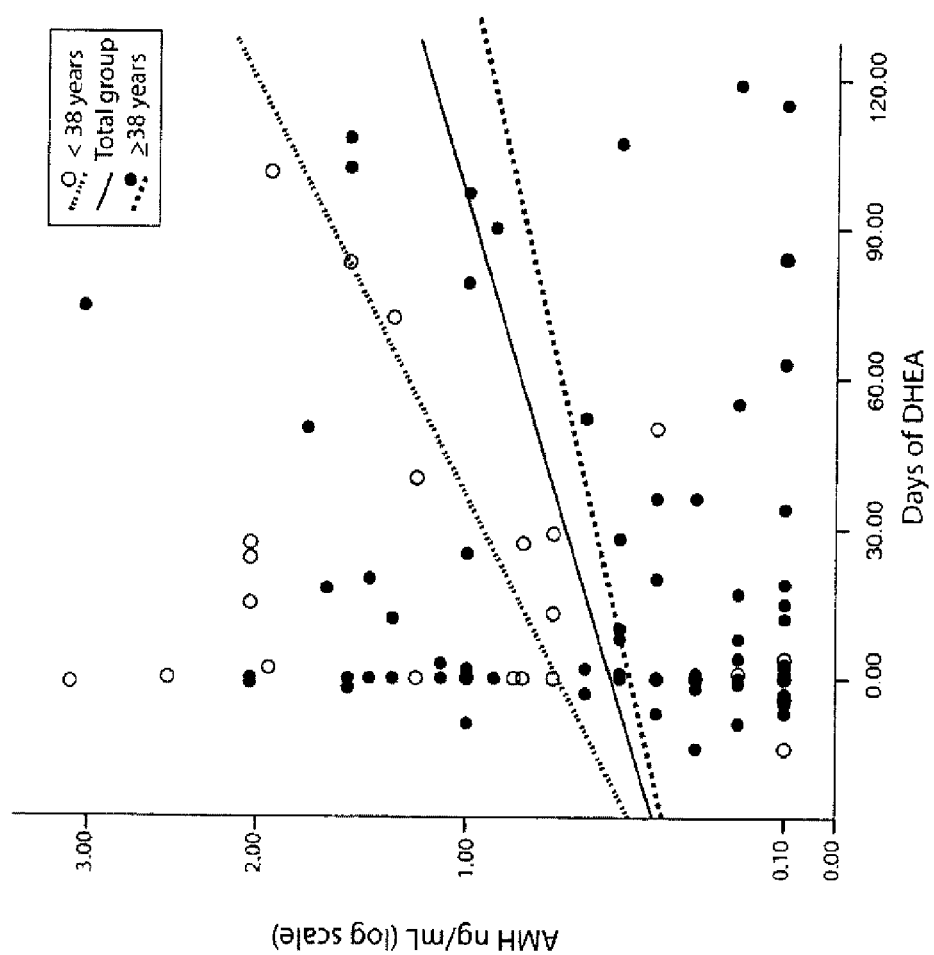
FIG. 23 is a graph showing AMH in POA and DOR patients over time of DHEA exposure.

AMH is, however, also in other ways predictive of treatment success with DHEA. AMH levels increase in parallel to length of DHEA supplementation and this increase is significantly more pronounced in younger POA than older DOR patients with physiologically aging ovaries (FIG. 23 is a graph showing AMH in POA and DOR patients over time of DHEA exposure. As the figure demonstrates, AMH increases significantly with length of DHEA treatment (full line). This effect is more pronounce in young POA patients (top line) than older DOR patients (bottom line).). Most importantly, however, improvements in AMH levels with DHEA supplementation are statistically highly predictive of pregnancy success.

While these data do not yet allow foreseeing which DOR patient will and will not conceive under DHEA supplementation, they, combined, can help offer patients appropriate informed consents. This is particularly important in view of recently issued ethics guidelines on fertility treatments in poor prognosis patients.

Treatment Protocols, Side Effects and Complications

Except for studies by the Baylor group, there are few pharmacological studies, addressing DHEA utilization in reproductive medicine. Those that exist, exclusively address post-menopausal women. Since one of the Baylor group's studies induced our index patient to start supplementation, she, like the Baylor group, supplemented with micronized DHEA, utilizing an over-the-counter product. In the past, over-the-counter DHEA products have been found inconsistent. While products may have improved, we have advised against over-the-counter products, and have recommended pharmaceutical grade, compounded DHEA, by prescription.

We maintained in all studies and treatment protocols the oral medication dosage of about 25 mg TID (three times a day for a total of about 75 mg per day), used by our index patient. Others, so far, uniformly have also used the same dosage, though this does not mean that it is the best dosage with least side effects. Studies to determine best dosaging of DHEA in the treatment of DOR have so far not been performed. There are also no studies in the literature which compare oral DHEA to other delivery systems for the drug in DOR, though studies by the Baylor group in other patients suggested distinct advantages from micronized and orally delivered DHEA.

Side effects of DHEA supplementation at this dosage are small and primarily relate to androgen effects. Few patients develop oily skin, acne vulgaris and hair loss but these side effects immediately reverse upon cessation of supplementation. More frequently patients comment on improved energy levels and sex drives.

In over 1,000 patients supplemented with DHEA so far, we have not encountered even a single complication of serious clinical significance. A recent case report from Israel reported the occurrence of a posttraumatic seizure after one month of DHEA supplementation in attempts to improve oocytes yields. Except for an anecdotal association, there appears, however, no clinical significance to this report. Even long-term therapy of DHEA, in dosages similar to the one described here, has been demonstrated to be safe.

As noted earlier, in the U.S. DHEA is, paradoxically, considered a food supplement and not a drug, and is, therefore, available without prescription. In other developed countries this is not the case. Many, indeed, restrict the compound's availability because of past abuses. DHEA studies reported by our center were until 2007 performed under IRB-approved study protocols. Since 2007 our center has recommended DHEA supplementation routinely to all patients, diagnosed with POA and/or DOR, since we consider these indications as clinically established. DHEA was recently listed amongst drugs with "orphan indications" in fertility therapy. Patients, nevertheless, still have to sign a DHEA-specific informed consent, which details potential risk and benefits.

Two other indications for DHEA supplementation are currently still under investigation in prospectively randomized, placebo controlled trials: unexplained infertility (trial number NCT00650754) and POF/POI (trial number NCT00948857).

How does DHEA Affect OR?

How DHEA improves OR, IVF parameters, pregnancy chances and decreases miscarriage rates is, ultimately, still unknown. Previously discussed evidence for beneficial effects on embryo ploidy may, at least in part, explain improvements in miscarriage rates. Assuming improved ploidy, one can expect more spontaneous pregnancies and pregnancies after IVF since it would suggest a pharmacological way of improving embryo selection, though less invasive to embryos than selection via PGS.

Hodges et al suggested that treatments can be developed which will reduce the risk of age-related aneuploidy by influencing meiotic chromosome segregation. These investigators believe that major disturbances in chromosome alignments on the meiotic spindle of oocytes (congression failure), responsible for aneuploidy, result from the complex interplay of signals regulating folliculogenesis. They thereby increase the risk of non-disjunction errors.

DHEA, indeed, may be a first such treatment!

This is a potentially very important concept because it suggests that the long held believe that oocytes age and that, therefore, aneuploidy increases may be incorrect. Instead, this new concept suggests that the unrecruited egg is suspended in time and, likely, does not age to a significant degree. What causes aneuploidy to increase with age is, therefore, not aging of oocytes but aging of the ovarian environment within which oocytes go through folliculogenesis. By correcting age-related changes in this ovarian environment (declining DHEA levels is only one amongst many such changes), aneuploidy levels can be maintained at levels usually only seen in younger women. Reduction of miscarriage rates in DHEA pregnancies to those of average, fertile patient populations is supportive of such a concept.

An effect on all of folliculogenesis (i.e., the whole follicular maturation cycle) is suggested by a number of already previously noted observations: the continuous improvement in DHEA effects, seen for at least five to six months, strongly supports a DHEA effect that increases as developing follicles are longer and longer exposed to DHEA. Furthermore, AMH is the product of small preantral follicles. Above noted increase of AMH levels with length of DHEA exposure (FIG. 23) further supports this contention. Finally, we also noted earlier that in spontaneously conceived DHEA pregnancies, miscarriages at different AMH levels appear mostly unaffected in contrast to pregnancies following IVF (FIG. 22). One of the possible explanations for this observation is the shorter time of DHEA exposure of spontaneously conceived pregnancies. Such an explanation would, of course, also be supportive of the concept and is further discussed below.

Other potential modes of DHEA action have, however, also to be considered: We noted earlier that the Baylor group suspected increases in ovarian IGF-1 to cause DHEA effects. IGF-1, indeed, appears reduced in poor responders to ovarian stimulation.

There is also increasing evidence that androgens, in general, may (within a therapeutic range) enhance ovarian function. In the mouse, androgens, years back, have been demonstrated to increase follicular recruitment. Increasing intrafollicular androgen levels augment granulose cell AMH and inhibin-B production. Androgen receptors have been described in ovarian stroma and granulose cells of primordial follicles, primary follicles and at more advanced stages of folliculogenesis; and ovarian androgens but not estrogens correlate with systemic inflammation during ovarian stimulation with gonadotropins.

Frattarelli and associates initially reported that day three testosterone levels at or under 20 ng/dL were associated with poorer IVF pregnancy rates. They later reported only an association with IVF stimulation parameters but no longer with pregnancy success. Iranian investigators, however, recently reported that testosterone levels on day 14 after embryo transfer are predictive of IVF pregnancies. Lossl et al published contradictory papers, one claiming and one refuting that treatment with aromatase inhibitors (which increases intrafollicular androgens) improves embryo quality. Contradictory results have also been reported by French investigators on short-term transdermal testosterone administration, with Massin et al reporting no benefit, while Balasch's group in two publications stress the beneficial effects of transdermal testosterone supplementation on ovarian resistance to stimulation with gonadotropins.

In combination, all of these studies raise the possibility that DHEA may not be the only androgen that positively affects ovarian functions. Further studies will, however, be needed to determine whether other androgens can reproduce effects like those reported here for DHEA. As the concluding section, below, will suggest, the really important question to be answered may, however, be even broader, and may, indeed, be a preview of the next big step forward in understanding ovarian physiology.

D. New Concepts

A New Concept of Age-Related Declining Fecundity

IVF has revolutionized infertility care in many different ways. Amongst the most significant are changes that go beyond medical considerations and, indeed, may have societal impacts. For example, IVF gives us the tools to maximize pregnancy chances while minimizing multiple pregnancy risks. It, however, has also revolutionized our clinical approach towards women with significant degrees of DOR. Pregnancy and live birth rates in women at very advanced reproductive ages are better than ever, and women above age 40 represent now the proportionally most rapidly growing age group of U.S. women giving birth.

Young women, with normal age-appropriate OR, now conceive quickly with IVF.

Figure 24C:
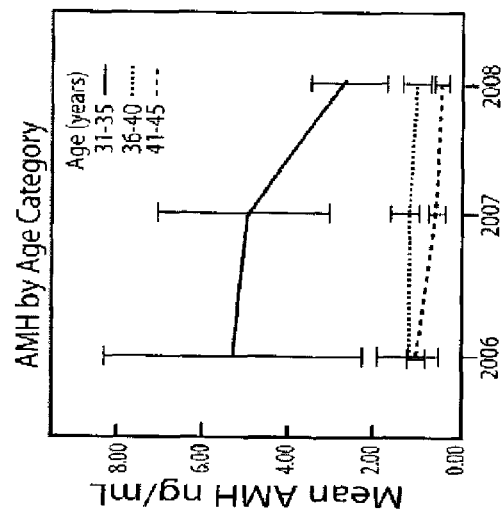
FIG. 24C is a graph showing trends in patient characteristics of our center's IVF population—AMH by age category. Graph C demonstrates that this age shift is also accompanied by a significant fall in AMH levels in younger women (ages 31-35 years) and, therefore, increasing DOR in these younger (POA) patients.
Figure 24B:
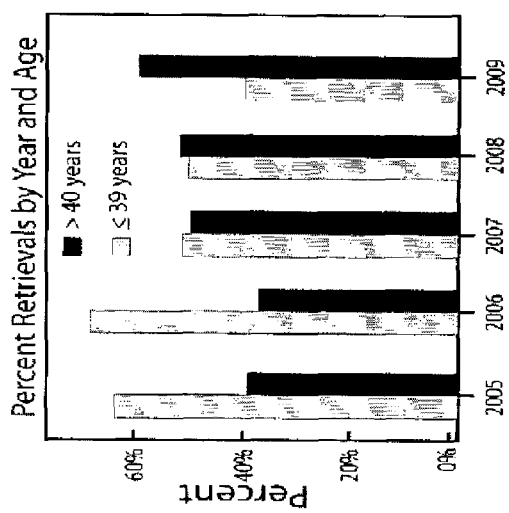
FIG. 24B is a graph showing tends in patient characteristics of our center's IVF population—percent retrievals by year and age. Graph B demonstrates the proportional shift from younger patients (<39 years) to older women (≧40 years).
Figure 24A:
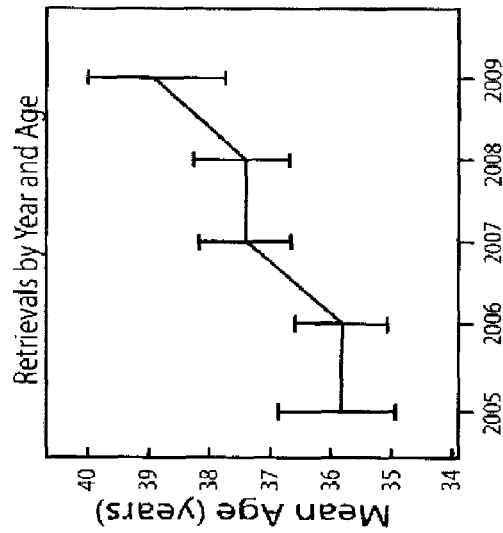
FIG. 24A is a graph showing trends in patient characteristics of our center's IVF population—retrieval by year and age. Graph A demonstrates mean ages for IVF patients between 2005 and year-to-date 2009.

Fertility centers, therefore, proportionally, now serve larger numbers of women with POA and/or DOR, as those accumulate disproportionally due to their lower pregnancy chances. At our center, mean patient age in 2009 has risen to approximately 39.5 years, and patients with premature and age-dependent DOR represent close to 90 percent of all patients (FIGS. 24: FIG. 24A is a graph showing trends in patient characteristics of our center's IVF population—retrieval by year and age. Graph A demonstrates mean ages for IVF patients between 2005 and year-to-date 2009. FIG. 24B is a graph showing tends in patient characteristics of our center's IVF population—percent retrievals by year and age. Graph B demonstrates the proportional shift from younger patients (<39 years) to older women ($\geq$40 years). FIG. 24C is a graph showing trends in patient characteristics of our center's IVF population—AMH by age category. Graph C demonstrates that this age shift is also accompanied by a significant fall in AMH levels in younger women (ages 31-35 years) and, therefore, increasing DOR in these younger (POA) patients. Combined, these data explain why in 2009 close to 90% of the center's population was affected by either POA or DOR.). Our center's demographics may be extreme, and a biased reflection of the center's areas of special clinical expertise and research interests. Infertility populations in all developed countries have, however, been graying.

The clinical problem of DOR has, therefore, progressively been moving from the periphery towards the center of priorities in infertility care. Effective clinical approaches towards DOR have, as a consequence, attracted considerable attention. We noted earlier that the index patient, aside from DHEA, found other potential remedies to enhance oocytes yields in her literature search. Yet others have been added since and, even more importantly, a better understanding of underlying pathophysiologies appears on the horizon.

Over the last few decades, and especially since IVF entered main stream clinical practice, ovarian stimulation protocols have been at the forefront of clinical research. Ovarian stimulation affects the ovary, however, only during approximately the last two weeks of folliculogenesis, when follicles become sensitive to gonadotropin stimulation. One of the reasons why, beyond their obvious clinical significance, here summarized effects of DHEA supplementation are potentially important, is their relevance for a much broader understanding of ovarian physiology.

Present dogma suggests that women are born with their oocytes and that these oocytes age as women age. Our current understanding of declining female fecundity with age, as previously noted, is based on declining follicle numbers and deteriorating egg quality with advancing female age. Here described DHEA work, however, raises serious questions about the concept of declining egg quality with advancing ovarian age.

Young POA patients, while exhibiting other typical signs of ovarian aging, like elevated FSH, low AMH and ovarian resistance to stimulation, fail to demonstrate increased aneuploidy. Oocytes at that young age, thus, apparently are not yet functionally "old" enough to exhibit the damage that would lead to aneuploidy. As noted earlier, oocytes in older women do, leading to the well recognized increase in aneuploidy and miscarriage rates with advancing female age.

As here summarized, DHEA supplementation apparently reduces these effects of age. This is best demonstrated by concentrating on available miscarriage data, which strongly suggest that DHEA supplementation in women of all ages significantly reduces miscarriage risk, and progressively more effectively so, with advancing female age. We previously already noted that the large decline in observed miscarriages can statistically not be achieved without reduction in aneuploidy, and that spontaneous pregnancy loss in very high risk populations for miscarriages is reduced to rates of normal fertile populations. Indeed, women with extremely low ovarian reserve, if they conceive, appear to have the lowest miscarriage rates (FIG. 22).

In absence of normal oocytes, such low miscarriage rates are inconceivable. Whatever effects DHEA, therefore, may exert, they either have to be able to revert "old" eggs into "young" ones (—a rather unlikely option—) or one has to consider that oocytes, by themselves, really do not age.

Primordial oocytes, which make up the unrecruited egg pool that constitutes a woman's true OR, therefore, most likely do not really age, as current dogma holds. Indeed, they, likely, similar to cryopreserved gametes, hibernate at metabolic rates close to zero until recruited into folliculogenesis. Once recruited, they pass the various stages of folliculogenesis within the age-dependent environment of a woman's ovary, which, of course, changes significantly as women age.

Under this concept it is not the egg that ages but the ovarian environment within which (—ever young—) oocytes mature through folliculogenesis. DHEA effects, under this concept, therefore, suddenly make sense: DHEA supplementation into a (in comparison to younger age) deficient ovarian DHEA environments would be expected to cause environmental "rejuvenation," and for upcoming cohorts of follicles to improve folliculogenesis to levels usually found only in younger women.

Assuming this to be the correct concept, a revolution in treating DOR appears possible, which will concentrate on maximizing conditions for all of folliculogenesis, rather than only its last two weeks of gonadotropin sensitivity. Should progress be made in this direction, it seems likely that the female's reproductive lifespan can be significantly extended. While egg numbers, of course, irreversibly decline with advancing age, even menopausal ovaries still contain follicles and oocytes. In the Squirrel monkey, older animals, immediately prior to cessation of reproduction, still demonstrate an abundance of well-differentiated granulosa cells, Assuming that unrecruited oocytes maintain their youth and that an aged ovarian environment can be rejuvenated, smaller, but healthier, egg cohorts may allow for pregnancy into very advanced female ages.

DHEA, therefore, likely only represents a first drug in a whole new class of pharmacological agents with potential to revert the ovarian environment to conditions, mimicking younger ages. Based on the known loss of mitochondrial functions with advancing age, Bentov et al, for example, recently suggested the use of mitochondrial nutrients, like coenzyme Q10 (CoQ10), in women with ovarian senescence after demonstrating that CoQ10 increases oocytes numbers in older mice. On a side note, androgens positively affect mitochondrial function.

We, therefore, see DHEA as a forerunner for many new drug-developments, with the goal of recreating an ovarian environment in DOR patients, mimicking that of younger women. To get to this point, it will become necessary to determine the key differences between younger and older ovaries, which make the latter a relatively inhospitable environment for folliculogenesis. Good potential technology for such studies has recently been developed.

Utilization Outside of Infertility

Above discussed findings and principles have so far been exclusively presented within the context of established infertility. Ovarian aging, however, does not only affect the infertile women. Indeed, the concept of age-dependent fecundity is driven by the recognition that ovaries age in normally fertile populations with expected age-dependent adverse consequences. These include progressively longer times to conception, increased aneuploidy and increased miscarriage risks, in principle similar to infertility patients.

One, therefore, can conceive of similar use of DHEA (and other pharmaceutical compounds) in normal, fertile populations, attempting to conceive. Like folic acid, in attempts to prevent neural tube defects, supplementation of healthy individuals above certain ages, attempting to conceive, may have similar favorable public health consequences.

XIV. Additional Information on a New Evolving Concept of Ovarian Aging

Under currently widely held dogma, women are born with a pool of primordial follicles. As women age, eggs in these "stored" follicles age in parallel. Older women, therefore, have "poorer quality" eggs, which lead to fewer pregnancies and more miscarriages. Summarizing current understanding of ovarian aging, one, therefore, can say "it's the eggs, stupid!"

But, if that is really the case, and if eggs really age, how come women with poorest OR, if they conceive, produce such good embryos that hardly any pregnancies are miscarried? It is this question that has preoccupied us here at CHR for quite some months now and for which we, finally, believe to have found a reasonable answer. Moreover, should this answer turn out to be correct, then our understanding of ovarian aging needs to be completely revamped.

Here is a short summary: We no longer believe that the eggs a woman is born with age. Instead, we believe that these eggs are maintained in a state of, more less, physiologic suspension, akin to cryopreserved eggs or embryos, which, once frozen, remain in status quo. Once primordial follicles are, however, recruited into folliculogenesis (a ca. 4.5 months long process of follicular maturation), these very immature eggs are entering a journey towards maturation, which is depending on the ovarian environment of the moment, which, of course, changes as women age.

It, therefore, is not eggs that age, as women age, but the ovarian environment in which eggs mature.

This distinction is of crucial importance: It seems unlikely that aged eggs can be returned to youth. An aged environment, however, may potentially be reversed with appropriate pharmaceutical therapies. Indeed, we now have come to believe that DHEA represents a first drug which has this kind of rejuvenating effect on the ovarian environment. By "correcting" the ovarian environment, DHEA allows for a follicular maturation process in some patients that mimics that of younger women. As a consequence, egg and embryo quality is improved, pregnancy rates are better and miscarriage rates are lower, as one would expect in younger women.

Pharmacologic infertility treatments, practically since inception, have concentrated on the last two weeks of folliculogenesis, when follicles become sensitive to gonadotropins. Under the here described new concept of ovarian aging, DHEA, likely, represents the first of a new class of fertility drugs, which, in contrast, affect folliculogenesis during the preceding four months.

The following examples are to be construed as merely illustrative and not limitative of the disclosure in any way.

EXAMPLE 1

Improved Ovulation

A study including a 43 year old woman, Patient A, undergoing IVF with banking of multiple cryopreserved embryos for future aneuploidy screen and transfer is administered an androgen, namely DHEA. In ten months she undergoes eight treatment stimulation cycles while continuously improving her ovarian response, resulting in oocyte and embryo yields far beyond those previously seen in a woman her age. Patient A's history is unremarkable except for two previous malarial infections. She is allergic to sulfa medications and has a history of environmental allergies. Her surgical history includes umbilical hernia repair at age one and cholecystectomy at age 21. She had used oral contraceptives for over 10 years. She has no history of irregular menstrual cycles.

Day three serum FSH and estradiol (E2) in her first IVF cycle are 11 mIU/ml and 18 pg/ml, respectively. In subsequent cycles her baseline FSH is as high as 15 mIU/ml. She is given an ovulation induction protocol which is prescribed for patients with evidence of decreased ovarian reserve. Briefly, the protocol includes the following medications: norethindrone acetate tablets (10 mg) for 10 days, starting on day two of menses, followed three days later by a "microdose" dosage of 40 µg of leuprolide acetate, twice daily, and, after another three days, by 600 IU of FSH (Gonal-F; Ares-Serono, Geneva, Switzerland) daily. Peak serum E2 concentration on day nine of stimulation is 330 pg/ml. Following injection of 10,000 IU human chorionic gonadotropin (hCG), she undergoes oocyte retrieval. Only one oocyte is obtained and one embryo is cryopreserved.

Because of the poor response to ovulation stimulation, she is advised to consider donor oocyte or embryo donation. She rejects both options. She starts a second cycle using the same stimulation protocol with one exception: instead of 600 IU of FHS daily, Patient A received 450 IU of FSH and 150 IU of human menopausal gonadotropin (HMG, Pergonal, Ares-Serono, Geneva, Switzerland). This stimulation protocol is continued in identical fashion for the remaining cycles. However, two weeks before starting her second cycle, she begins administration of 75 mg per day of oral micronized DHEA. The date on which she begins administration of 75 mg per day of oral micronized DHEA is Oct. 6, 2003.

Methods of Example 1

The eight treatment cycles are divided into three groups to allow statistical comparison: pre-initiation and very early use of DHEA (early=cycles 1 and 2), initial cycles (mid=cycles 3-5), and later cycles (late=cycles 6-8). Comparison between these categories is by one-way analysis of variance (ANOVA) and multiple comparisons by Student-Neuman-Keuls (SNK) test. The homogeneity of variances and used orthogonal linear contrasts are tested to compare groups and polynomial contrast to test for linear and quadratic trends. All outcomes are presented as mean±1 standard deviation. Rate of change of oocyte counts, cryopreserved embryos and (log transformed) peak estradiol between subsequent cycles is estimated by linear regression.

Embryos are evaluated by the embryologists on day three post-insemination for cell-count and grading. Embryo grading is based on a 1 to 4 scale depending on symmetry, percent fragmentation and appearance of the cytoplasm. All viable embryos are cryopreserved. Statistics are performed using SPSS for Windows, Standard version 10.0.7 (SPSS Co., Chicago, Ill.). Assay of E2 and FSH are performed using the ACS: 180 chemoluminescence system (Bayer Health Care LLC, Tarrytown, N.Y.).

A method of preconditioning ovulation induction in a human female is conceived, comprising administering an androgen in a female for at least about four consecutive months. In one embodiment, the androgen is DHEA. Administration of DHEA for at least about four consecutive months may further comprise administering high dose gonadotropins to the female. Furthermore, DHEA may be administered along with follicle stimulating hormone, human menopausal gonadotropin, norethindrone acetate, leuprolide acetate, and human chorionic gonadotropin. DHEA may be administered orally.

The length of time the androgen is administered to the female can be at least four consecutive months. The DHEA treatment may continue for more than four months. In one embodiment, the androgen administered is DHEA.

Results of Example 1

The results of ovulation induction are displayed in FIG. 1. After eight stimulation cycles and approximately eight months of DHEA treatment, Patient A produced 19 oocytes and 11 cryopreservable embryos. A total of 50 viable embryos have so far been cryopreserved. Significantly more oocytes (p=0.001) and cryopreserved embryos (p<0.001) are obtained in the late cycles (cycles 6-8, 4+consecutive months of DHEA treatment) compared to the combined early and mid cycles (cycles 1-5, 0-4 consecutive months of DHEA treatment). There is no significant difference in average embryo cell count (6.83±1.37 vs. 7.2±1.15) or morphology (3.6±0.5 vs. 3.7±0.5) between early and mid compared to late cycles. Peak E2, total oocyte, and embryos cryopreserved increase linearly from cycle to cycle, as shown in FIG. 1. Oocyte yield increase 2.5±0.34 oocytes per cycle (p<0.001), cryopreservable embryo yield increase 1.4±0.14 embryos per cycle (p<0.001) and (log) peak E2 increase 0.47±0.06 (p<0.001) across treatment cycles.

The linear increase in (log) peak E2 shown in FIG. 2 represents a cycle to cycle rate of increase from 123 pg/ml/cycle to 1491 pg/ml/cycle over the eight cycles of treatment. After adjusting for cycle day, the (harmonic) mean E2 is 267 pg/ml (95% confidence intervals (CI) 143 to 498 pg/ml) in the early phase, 941 pg/ml (95% CI 518 to 1712 pg/ml) in the mid phase, and 1780 pg/ml (95% CI 1121 to 2827 pg/ml) in the late phase of treatment. Each of these homogeneous subsets is significantly different from the other (p<0.05) by SNK multiple comparison testing.

The dramatic increase in oocyte and embryo yield experienced by this 43 year old woman is completely surprising and unexpected. Patient A's post-DHEA response to ovulation induction has become more like that of a younger woman with PCO, than that of a 43 year old woman. Since starting DHEA treatment, Patient A has produced 49 embryos of high enough quality to undergo cryopreservation. Sixty percent of those embryos were produced in the last three cycles of treatment, which took place after at least about four consecutive months after starting treatment. After producing only one embryo prior to starting DHEA treatment, Patient A improved by an order of magnitude and produced 13 oocytes and 9 embryos in a cycle after at least about four consecutive months of DHEA treatment, 16 oocytes and 10 embryos in a cycle after at least about five and a half consecutive months of DHEA treatment, and 19 oocytes and 11 embryos in a cycle after at least about seven consecutive months of DHEA treatment.

The increasing numbers of cryopreservable embryos due to DHEA supplementation suggest improved embryo quality.

EXAMPLE 2

Improved Oocyte Fertilization and Cumulative Embryo Score

In another study, thirty (30) patients with evidence of decreased ovarian reserve were given supplemental DHEA 25 mg three times a day, for a total of 75 mg per day, for an average of about 4 months before beginning ovulation induction for IVF. Twelve patients contributed data from cycles both pre-DHEA and post-DHEA, eleven patients contributed data from cycles only pre-DHEA, and seven patients contributed data from cycles only post-DHEA. Patients' response to ovulation induction before DHEA treatment was compared to patients' response to ovulation induction after DHEA treatment with regard to peak estradiol, oocyte production, and embryos transferred and embryo quality.

The thirty patients contributed to data for 42 total cycles, 23 cycles prior to and 19 cycles after starting DHEA supplementation. In comparing the patients as a group pre- and post-DHEA treatment cycles, there were improvements in cancellation rate, peak estradiol, average day 3 embryo cell counts, and embryo grade. However, average oocyte numbers, eggs fertilized, day-three embryos, embryos transferred and cumulative embryo scores increased significantly after DHEA treatment. In logistic regression models adjusted for oocyte number, there was evidence of improved fertilization rates ($p<0.005$), increased numbers of day-three embryos ($p<0.05$), and of improved overall embryo score ($p<0.01$). In 34 IVF cycles that reached the embryo transfer stage, a positive pregnancy test was obtained in zero of 16 cycles with less than an average of about 4 months of DHEA treatment and in 4/18 cycles after an average of 4 months of DHEA treatment.

This case series illustrates that some ovarian function can be salvaged, even in women of advanced reproductive age.

TABLE 1

Univariate comparison of results of in vitro fertililization before and after treatment with DHEA.

|  | Pre DHEA | Post DHEA | p |
| --- | --- | --- | --- |
| N | 23 | 19 |  |
| Age | 40.9 ± 0.7 | 42.8 ± 0.7 | ns |
| Weeks of DHEA | — | 16.1 ± 2.4 | — |
| Cancellation | 5/21 (21%) | 1/19 (5%) | ns |
| Peak Estradiol | 1018 ± 160 | 1192 ± 904 | ns |
| Oocytes | 3.3 ± 0.7 | 5.8 ± 1.0 | 0.04 |
| Fertilized eggs | 1.3 ± 0.3 | 4.6 ± 0.8 | <0.001 |
| Average Day 3 embryo cell count | 3.1 ± 0.6 | 4.5 ± 0.5 | ns |
| Average Day 3 embryo grade | 2.4 ± 0.3 | 2.8 ± 0.3 | ns |

TABLE 1-continued

Univariate comparison of results of in vitro fertilization before and after treatment with DHEA.

|  | Pre DHEA | Post DHEA | p |
| --- | --- | --- | --- |
| Cumulative Embryo Score | 34 ± 6.8 | 98 ± 17.5 | 0.001 |
| Transferred embryos | 1.0 ± 0.2 | 2.6 ± 0.4 | 0.001 |
| Number of Day 3 embryos | 0.9 ± 0.2 | 3.2 ± 0.6 | 0.001 |
| Positive hCG (per transfer cycle) | 0/16 | 4/18 | ns |

Cycle characteristics and responses to treatment are shown in Table 1. The average age of the patients who began DHEA was 41.6±0.6 years. Women in the DHEA group used DHEA for a median value of 16 weeks before their IVF cycle. The cycle cancellation rate was 5 of 21 cycles (21%) pre-DHEA and 1 of 19 (5%) post-DHEA. There was no statistically significant difference in peak estradiol levels between pre- and post-DHEA cycles.

Continuing with the cycle outcomes presented in Table 1, there are improvements in average cell count of day-three embryos and mean embryo grade after DHEA treatment, however the differences are not significant. Mean oocyte numbers, fertilized eggs, day-three embryos, embryos transferred and cumulative embryo scores, all increased significantly after DHEA treatment. In the models adjusted for oocyte number, there was still evidence of increased fertilization rates (1.93 fertilized oocytes, 95% C.I. 0.82-3.04; $p<0.005$), increased numbers of day-three embryos (1.36 embryos, 95% C.I. 0.34-2.4; $p<0.05$), and of improved overall embryo score (32.8, 95% C.I. 9.6-56; $p<0.01$).

FIG. 3 shows paired comparisons of fertilized oocytes (average increase 2.5±0.60; p=0.002) among 12 patients with DHEA treatment cycles of less than about 4 weeks to fertilized oocytes in the same 12 patients after at least about 4 weeks of DHEA treatment. FIG. 4 shows paired comparisons of day 3 embryos (average increase 2.0±0.57; p=0.005) among 12 patients with DHEA treatment cycles of less than about 4 weeks and at least about 4 weeks during IVF cycles. The paired comparisons shows that the mean increase in the number of fertilized oocytes was modest, but significant, (1.42±0.63 increased numbers of fertilized oocytes; $p<0.05$).

The mean increase in embryo scores was 57±14.7 ($p<0.01$). The increase in the number of day 3 embryos was 2.0±0.57 (p=0.005) (See FIG. 4) and the increased fertilization quantity was 2.5±0.60 fertilized oocytes per patient (p=0.002) (See FIG. 3). DHEA supplementation improves the average oocyte numbers, eggs fertilized, day three embryos, embryos transferred, and cumulative embryo score.

In addition, DHEA supplementation also improves pregnancy rates and decreases time to pregnancy. Two patients achieved ongoing pregnancies while taking DHEA without IVF; one (43 year old) while using DHEA during a stimulated IUI (intrauterine insemination) cycle and a second (37 year old) conceived spontaneously following an unsuccessful IVF cycle. A third patient (40 year old) also conceived spontaneously while preparing for an IVF cycle; however that pregnancy ended in a spontaneous abortion. In all 7 of 45 (16%) patients using DHEA have conceived and 5 of 45 patients (11%) have experienced continuing pregnancies.

EXAMPLE 3

Increased Euploidy Rate

In another study (data not shown), patients were analyzed after four weeks of DHEA treatment. Seven patients had embryos tested by pre-implantation genetic diagnosis (PGD). In three women who had PGD after less than four weeks of DHEA usage and a mean age 41.5±5.1 at the time of starting IVF cycles, the euploidy, or normal chromosome number, rate was 2/30 embryos (6.6%). In six patients who had PGD after more than four weeks of DHEA usage, and a mean age of 43.7±1.3 years at the time of starting IVF cycles, the euploidy rate increased to (8/27; 29.6%), though this trend did not reach statistical significance. There is a mean age difference between patients who underwent IVF after less than four weeks of DHEA usage (mean age 41.5±5.1) and patients who underwent IVF after at least four weeks of DHEA usage (mean age 43.7±1.3).

As women age, there is a substantial decline in euploidy rates in embryos produced. Thus, the increase in euploidy results in older women is dramatic evidence of the effectiveness of DHEA in improving embryo quality.

EXAMPLE 4

DHEA Treatment Increases Euploidy Number

In a series of studies, it has been documented that DHEA supplementation in women with diminished ovarian reserve (DOR) increases egg and embryo count, improves egg and embryo quality, increases pregnancy rates, and shortens time to conception.

The reports of the studies point towards improvements in follicular recruitment after treatment with androgenic compounds. Since DHEA effects are statistically significant after approximately four months, and since this time period is approximately reflective of the full follicular recruitment cycle, we concluded that DHEA may, at least in part, affect follicular recruitment processes, possibly by influencing apoptosis. Androgens have been reported to affect granulosa cell apoptosis.

While women with prematurely DOR appear to have normal embryonic aneuploidy rates, older women, with physiologic aging ovaries, demonstrate very high aneuploidy rates of their embryos. Increasing aneuploidy rates with advancing female age are, therefore, considered a primary cause for diminishing pregnancy chances, and an increasing miscarriage risk, in older women. Since treatment with androgenic compounds in such patients appears to improve embryo quality and pregnancy chances, it is likely that such treatment positively affects aneuploidy rates.

Materials and Methods of Example 4

All the IVF cycles performed at the Center for Human Reproduction (CHR) in New York, N.Y., between 2004 and 2006 for cycles performed in women with a diagnosis of DOR were retroactively reviewed. The study population, involving 27 IVF cycles, was selected amongst those cycles which, in addition, had undergone preimplantation genetic diagnosis (PGD).

The diagnosis of DOR was made based on previously reported abnormally high, age stratified baseline FSH levels. In practical terms, this meant that a diagnosis of DOR was reached if baseline FSH levels exceeded the 95% confidence interval of age appropriate levels, independent of prior IVF retrievals and/or oocyte numbers. At, or above age 43, all patients were considered to suffer from DOR, independent of baseline FSH level.

Since the year 2004, women with proven DOR, who had undergone at least one prior ovarian stimulation, demonstrating ovarian resistance based on inadequately low oocyte numbers, routinely were offered oral DHEA supplementation (25 mg TID) prior to any further IVF cycle starts. If under age 40, DHEA was given for up to four months prior to IVF. Women of older age received DHEA, if possible, for at least two months.

Women with DOR, who had no proof of ovarian resistance, were not placed on DHEA supplementation until such proof was obtained, unless they were at, or above, age 43 years. IVF cycles on DHEA supplementation have, therefore, to be considered as more severely affected by DOR than those cycles that were conducted without such supplementation. This fact is also reflected by the baseline cycle characteristics of DHEA-treated, and untreated, patients (Table 2), which demonstrate trends towards older age and higher baseline FSH levels in DHEA treated patients.

TABLE 2

Baseline characteristics of DHEA-treated, and -untreated, patients[1]

| | DHEA - TREATED n = 8 | DHEA - UNTREATED n = 19 |
|---|---|---|
| Age (±SD, year) | 41.2 ± 4.7 | 38.9 ± 5.1 |
| Baseline FSH[2] ± SD (mIU/ml) | 12.4 ± 9.2 | 9.0 ± 2.7 |
| Baseline Estradiol[2] ± SD (pg/ml) | 59.7 ± 32.2 | 68.1 ± 59.1 |

[1]None of the baseline parameters, listed in the table, differed to a statistically significant degree between the two groups.
[2]Reflects highest baseline level of each patient, and not necessarily the baseline level of the IVF cycle.

For the purpose of this analysis, a patient had to be for at least one month (30 days) on DHEA supplementation in order for the IVF cycle to be considered amongst DHEA—treated cycles. All other DOR patients were considered to have received no DHEA treatment. Following this definition, 19 DOR patients had received no DHEA supplementation, and eight had.

All women with DOR, independent of DHEA supplementation, were stimulated with identical protocols, as previously reported in detail elsewhere. In short, they, without exception, received a microdose agonist protocol with maximal goanotropin stimulation of 600 IU to 750 IU daily, with preponderance of FSH, and a smaller daily amount of human menopausal gonadotropin (hMG).

PGD was performed in routine fashion, as also previously described in detail, and involved the analysis of chromosomes X, Y, 13, 16, 18, 21 and 22 by fluorescence in situ hybridization (FISH) on day three after fertilization. Embryo transfer occurred on day five after fertilization.

Patients were represented by only one cycle outcome in each group. If patients had undergone more than one cycle, either with, or without, DHEA supplementation, only their latest cycle was included in the analysis. Three patients underwent both a pre-DHEA and a post-DHEA cycle and in those cases both cycles were included in the analysis.

Statistical analysis was performed using SPSS for windows, standard version 10.0.7. Data are presented as mean±one standard deviation, unless otherwise noted, and statistical differences between the two study groups were tested by Chi-square and (two-sided) Fisher's Exact Test, where applicable, with significance being defined as p<0.05.

Results of Example 4

A total of 27 consecutive IVF cycles in women with DOR who also had undergone preimplantation genetic diagnosis (PGD) were identified and evaluated. Amongst those, 19 had entered IVF without DHEA treatment and 8 had received DHEA supplementation for at least four weeks prior to IVF start.

Table 3 summarizes cycle outcomes.

TABLE 3

IVF cycle and PGD outcomes

|  | DHEA - TREATED | DHEA - UNTREATED |
|---|---|---|
| Peak Estradiol ± SD (pg/ml) | 2310.3 ± 1108.1 | 2123.3 ± 1054.7 |
| Oocytes ± SD | 10.4 ± 7.3 | 8.5 ± 4.6 |
| Embryos ± SD[1] | 9.1 ± 7.3 | 5.7 ± 2.7 |
| n Euploid ± SD | 2.1 ± 1.4 | 1.6 ± 2.3 |
| % Euploid ± SD | 44.1 ± 37.8 | 21.4 ± 27.5 |
| n Aneuploid ± SD | 4.4 ± 3.0 | 3.5 ± 0.3 |
| % Aneuploid ± SD | 55.9 ± 37.8 | 78.6 ± 27.5 |
| Patients with euploid embryos (%) | 8/8 (100)[2] | 7/13 (53.8)[2] |

SD, standard deviation of mean;
[1]Reflects total number of embryos. Since only high quality 6-cell to 8-cell day-3 embryos undergo PGD, the number of embryos tested for ploidy was smaller.
[2]Reflects a statistically significant difference by Likelihood ratio (p = 0.004) and (two-sided) Fisher's Exact Test; p = 0.026. Other comparisons in this table did not reach statistical significance.

DHEA treatment resulted in trends towards higher oocyte numbers (10.4±7.3 vs. 8.5±4.6). A significantly larger number of DHEA treated IVF cycles (eight out of eight, 100%) had at least one euploid embryo for transfer than in untreated cycles (10/19, 52.6%; Likelihood ratio, p=0.004; Fisher's Exact Test, p=0.026). In other words, the primary result reaching statistical significance was the difference in the percentage of IVF cycles which resulted in the transfer of at least one euploid embryo, with DHEA treated patients reaching embryo transfer in 100 percent of cycles, while untreated patients did so in only 52.6 percent of cases.

As can be seen in Table 3, peak estradiol levels, oocyte and embryo numbers and the results of PGD, all demonstrated trends towards a beneficial effect of DHEA. Peak estradiol levels were higher and oocyte, as well as embryo numbers, were larger. There was also a trend towards more euploidy in embryos from treated cycles, both in absolute numbers and in percentages of embryos evaluated by PGD.

Amongst the 27 reported cycles, three patients contributed pre- and post-DHEA cycles. When these cycles were separately analyzed, they demonstrated similar trends as observed for the whole study (Table 4).

TABLE 4

IVF cycle parameters in 3 women
with DHEA and -no-DHEA cycles[1]

| Age ± SD (years) | 38.2 ± 5.5 |
|---|---|
| Baseline FSH[2] ± SD (mIU/ml) | 10.5 ± 1.5 |
| Baseline Estradiol[2] ± SD (pg/ml) | 54.4 ± 21.7 |

|  | DHEA - TREATED | DHEA - UNTREATED |
|---|---|---|
| Time pre-/post DHEA (months) | 2.4 ± 2.5 | 1.9 ± 2.2 |
| Oocytes ± SD | 6.0 ± 4.8 | 4.8 ± 1.0 |
| Total Embryos ± SD | 4.0 ± 2.7 | 4.5 ± 0.6 |
| Aneuploid Embryos | 2.0 ± 1.8 | 3.5 ± 0.6 |

SD, standard deviation;
[1]None of the differences between the two study groups reached statistical significance.
[2]Reflects highest baseline level of patients, but not necessarily baseline level during IVF cycle.

Discussion of Example 4

The here presented study demonstrates evidence that DHEA improves, to a statistically significant degree, the number of euploid embryos available for embryo transfer after IVF, and may be at least a partial explanation of why DHEA supplementation improves pregnancy chances in women with DOR. The study also demonstrates a trend towards higher percentages of euploid embryos after DHEA and higher absolute numbers of euploid embryos. The here observed effect of statistically more transferable, euploid embryos, may be due to larger oocyte and embryo numbers, lower aneuploidy rates, or both effects combined.

The mean number of euploid embryos increased after DHEA treatment by approximately one-half embryo. One-half additional embryo, especially if proven euploid, represents significant additional pregnancy potential in women with DOR, who usually produce only relative small embryo numbers. Indeed, this reflects approximately a one-third improvement in euploid embryo yield, and results in the availability of at least one embryo for transfer in all post-DHEA cycles. In comparison, only 52.6% of untreated cycles achieved the same goal. This is a statistically significant difference in embryo transfers. Pretreatment with DHEA of women with DOR significantly increases their chances for the transfer of at least one euploid embryo and may, therefore, at least in part, explain the higher pregnancy rates reported with DHEA supplementation.

Based on the incremental improvement in DHEA effects for up to four months, and the correlation of the time span to a full cycle of follicular recruitment, it is suspect that DHEA may affect apoptotic processes during follicular recruitment. As a consequence, more healthy follicles survive maturation, reach the stage of gonadotropin sensitivity and become subject to exogenous gonadotropin stimulation. These, in turn, also could be expected to have a higher probability of euploidy.

Increasing aneuploidy rates with female age are considered the principle cause of decreasing spontaneous female fertility, increasing infertility and rising miscarriage rates. DHEA may improve euploidy rates as will be discussed in more detail herein, and in turn, improves spontaneous female fertility, decreases the rate of female infertility and reduces miscarriage rates.

EXAMPLE 5

DHEA Substitution Improves Ovarian Function

In a further study, a case of probable 17, 20-desmolase deficiency, resulting in abnormally low estradiol, DHEA, androstenedione and testosterone levels, is presented in a woman with a clinical history of, initially, unexplained infertility and, later, prematurely aging ovaries.

This patient started attempting conception in 1996, at age 33. After failing to conceive for over one year, she was diagnosed with hypothyroidism and was placed on levoxyl. She, thereafter, remained euthyroid for the whole period described in this case report. She entered fertility treatment at a prominent medical school based program in Chicago, in August of 1997, where, now age 34, she failed three clomiphene citrate cycles. No further treatment took place until a laparoscopy was performed in October of 1999, at a prominent Atlanta-based infertility center (where the couple had relocated to), revealing stage II endometriosis which was laser vaporized. Following surgery, a fourth clomiphene citrate cycle and a first gonadotropin-stimulated cycle failed. Table 5 presents selected key lab data for all ovarian stimulation cycles the patient underwent. A first in vitro fertilization (IVF) cycle was performed, at age 36, in October of 2000.

This cycle resulted in expected oocyte and embryos yields. Three embryos were transferred, resulting in a chemical pregnancy. Three other embryos were cryopreserved. However, because of a persistently thin endometrium, a number of attempts at transfer were cancelled.

In April of 2001, the patient was, based on an abnormal glucose tolerance test, diagnosed with insulin resistance, and was placed on metformin, 500 mg thrice daily. She had no signs of polycystic ovarian disease: her ovaries did not look polycystic, she was not overweight, had no signs of hirsutism or acne, and androgen, as well as estradiol, levels were in a low normal range (Table 2). In June of 2001 (age 37), a second IVF cycle was initiated. In this cycle the patient demonstrated the first evidence of ovarian resistance to stimulation in that she produced only six oocytes. Only one out of five mature oocyte fertilized, despite the utilization of intracytoplasmic sperm injection (ICSI). The previously cryopreserved embryos were, therefore, thawed and transferred, together with the one fresh embryo from the current cycle. The transfer was unsuccessful.

In August of 2001, the female's FSH level for the first time was abnormally elevated (11.4 mIU/ml), with estradiol levels remaining low-normal. Subsequent FSH levels were 19.1, 9.7 and 9.8 mIU/ml in November and December (twice), respectively, all with low-normal estradiol levels. FSH levels continued to fluctuate in 2002, with levels reported as 11.4 mIUI/ml in February, 8.7 in March, 13.6 in June and 19.6 in September, while estradiol levels remained persistently low-normal (Table 2).

A third IVF cycle was started in October of 2002, with a baseline FSH of 11.3 mIUI. Ovarian stimulation, which in the prior two cycles had been given with only recombinant FSH (and antagonists), was now given in a combination of recombinant FSH and hMG at a combined dosage of 300 IU daily. Estradiol levels reached only 890 pg/ml and only 5 oocytes were retrieved. All four mature oocytes fertilized and four embryos were transferred. A twin pregnancy was established by ultrasound and a singleton by heart beat. This pregnancy was, however, miscarried and confirmed as aneuploid with a Trisomy 22.

The fact that this cycle, after the addition of hMG to the stimulation protocol, appeared more successful, led the patient to a search of the medical literature. Like our previously reported patient (Barad and Gleicher, 2005), this patient discovered a case series. The paper attracted the patient's interest. In follow up, she asked a medical endocrinologist to evaluate her adrenal function. An initial evaluation revealed very low DHEA, DHEA-S, androstenedione and testosterone levels (Table 2). An ACTH-stimulation test was ordered which showed the expected increase in cortisol level, but unchanged, low DHEA, DHEA-S and testosterone levels (Table 3). The patient was advised by her medical endocrinologist that the most likely explanation for such a finding was a 3-beta hydroxysteroid dehydrogenase deficiency. This enzyme defect is, however, associated with an accumulation of DHEA and, therefore, high levels of the hormone. (Speroff et al., 1999a). Such a diagnosis for the patients is, therefore, unlikely. Instead, abnormal 17,20-desmolase (P450c17) function would be expected to result in exactly the kind of hormone profile, reported in this patient after ACTH stimulation, characterized by persistently low DHEA, androstenedione, testosterone and estradiol levels, but normal aldosterone and cortisol levels.

In July of 2003, the patient was started on 25 mg daily of micronized DHEA. After five weeks of treatment, DHEA, DHEA-S and androstenedione levels had normalized into mid-ranges. (Even though androstenedione is partially produced through the activity of 17,20-desmolase from 17-hydroxyprogesterone, part is also derived from DHEA through the activity of 3-beta hydroxysteroid dehydrogenase [Speroff et al., 1999a]. The normalization of androstenedione, after DHEA administration, therefore, also speaks for an underlying 17,20-desmolase defect, and not a 3-beta hydroxysteroid dehydrogenase deficiency.) In the third and fourth month, following the start of DHEA supplementation, the patient ovulated spontaneously with estradiol levels of 268 and 223 pg/ml (Table 2), respectively, measured on the day of LH surge.

On Jan. 28, 2004 (age 39), and after DHEA therapy of approximately six months, a fourth IVF cycle was initiated. Her baseline FSH level in that cycle was 9.6 mIU/ml, estradiol 56 pg/ml. Stimulation took place with 300 IU of recombinant FSH (without hMG) and with an agonist flare protocol. Estradiol levels reached a peak of 1764 pg/ml, 8 oocytes were retrieved, six out of seven mature oocytes fertilized and six embryos were transferred. A triplet pregnancy was established with heart beats. Two, out of the three fetuses lost heart beat spontaneously, and the patient delivered by cesarean section, at term, a healthy singleton male infant.

At surgery, her ovaries were closely inspected and described as "old" and "small", with the left one being described as "almost dead." DHEA and DHEA-S levels at six months of pregnancy were reported at "record lows." DHEA-S, six weeks post-delivery, was still very low (Table 5). At time of this report, the male offspring is nine months old and the mother has been re-started on DHEA in an attempt at another pregnancy.

DHEA substitution resulted in apparently normal peripheral DHEA levels, spontaneous ovulation and normal estradiol production by the ovaries. An IVF cycle, after approximately six months of DHEA substitution, showed, in comparison to a pre-DHEA IVF cycle, improved peak estradiol levels, increased oocyte and embryo numbers and resulted, at age 39, after 6 years of infertility therapy, in a triplet pregnancy and a normal singleton delivery.

Low DHEA levels appear associated with female infertility and ovarian aging. DHEA substitution normalizes peripheral DHEA levels and appears to improve ovarian response parameters to stimulation.

The reported patient exhibited some of the classical signs of prematurely aging ovaries (Nikolaou and Templeton, 2003; Gleicher N, 2004) which include ovarian resistance to stimulation, poor egg and embryo quality and prematurely elevated FSH levels. The patient was initially thought to have largely unexplained infertility. She later developed quite obvious signs of prematurely aging ovaries and, finally, even showed elevated FSH levels.

It has been previously suggested that the decrease in DHEA levels, with advancing female age, may be an inherent part of the ovarian aging process and may, at least in part, and on a temporary basis, be reversed by external DHEA substitution (Barad and Gleicher, 2005, 2005a). This case demonstrates that low DHEA levels are, indeed, associated with all the classical signs of both prematurely and normally aging ovaries. While association does not necessarily suggest causation, the observed sequence of events in this patient supports the notion that low DHEA levels adversely affect ovarian function.

Once the patient was administered oral DHEA, a reversal of many findings characteristic of the aging ovary, were noted. First, the patient's DHEA and DHEA-S levels normalized. In subsequent natural cycles an apparently normal spontaneous follicular response was observed, with normal ovulatory estradiol levels in a patient with persistently low estradiol levels before DHEA treatment (Table 5). The response to ovarian stimulation improved, quantitatively and qualitatively, as the patient improved peak estradiol levels, oocyte and embryo numbers and, as the successful pregnancy may suggest, also embryo quality.

One cannot preclude that other factors contributed. For example, the ovarian stimulation protocol had switched from an antagonist to an agonist flare protocol. The data demonstrates that a maximal effect of DHEA is achieved after at least about four consecutive months of use. This patient was on DHEA treatment for approximately six months before she conceived the pregnancy that led to her first live birth.

This case is well documented in its DHEA deficiency and in its most likely cause. The reported adrenal response to ACTH stimulation (Table 5) lends itself to the explanation (FIG. 1) of 17,20-desmolase deficiency.

TABLE 5

Relevant laboratory results

| Date | TEST | RESULT (Normal values)* | | COMMENTS |
|---|---|---|---|---|
| August 1997 | TSH | 7.8 mIU/l | (0.4-5.5) | Diagnosis of hypothyroidism |
| May 1999 | FSH | 4.0 mIU/ml | | |
| April 2001 | Glucose tolerance test | Elevated ½ hour insulin levels Normal Glucose levels | | Diagnosis of insulin resistance |
| June 2001 | FSH | 7.7 mIU/ml | | |
| | Estradiol | 33 pg/ml | | |
| August 2001 | Testosterone | 2 ng/dl | (3-29) | |
| | free/weakly bound | | | |
| | free only | 1 pg/ml | (1-21) | |
| | total | 13 ng/dl | (15-70) | |
| | DHEA-S | 96 mcg/dl | (12-379) | |
| | Total Cortisol | 14.2 mcg/ml | (4-22) | |
| | FSH | 11.4 mIU/ml | | Diagnosis of prem. ov. aging |
| | Estradiol | 45 pg/ml | | |
| October 2001 | Estradiol periovulatory | 119 pg/ml | | |
| November 2001 | Testosterone total | 23 ng/ml | (14-76) | |
| | Androstenedione | 98 ng/ml | (65-270) | |
| | Ovarian antibodies | negative | | |
| | FSH | 19.1 mIU/ml | | |
| | Estradiol | 23 pg/ml | | |
| December 2001 | FSH | 9.7 mIU/ml | | |
| | Estradiol | 27 pg/ml | | |
| February 2002 | Testosterone total | <20 ng/dl | (20-76) | |
| | Androstenedione | 76 ng/dl | (65-270) | |
| | FSH | 11.4 mIU/ml | | |
| | Estradiol | 28 pg.ml | | |
| March 2002 | Testosterone total | 16 ng/dl | (15-70) | |
| | FSH | 8.7 mIU/ml | | |
| | Estradiol | 29 pg/ml | | |
| May 2002 | FSH | 13.6 mIU/ml | | |
| | Estradiol | 30 pg/ml | | |
| | periovulatory | 139 pg/ml | | |
| June 2002 | periovulatory | 50 pg/ml | | |
| September 2002 | Testosterone total | 15 ng.dl | (15-70) | |
| | free | 1.6 pg/ml | (1-8.5) | |
| | % free | 0.0107 | (0.5-1.8) | |
| | Estradiol periovulatory | 136 pg/ml | | |
| October 2002 | FSH | 11.3 mIUI/ml | | |
| | Estradiol | 43 pg/ml | | |
| February 2003 | FSH | 13.6 mIU/ml | | |
| | Estradiol | 33 pg/ml | | |
| March 2003 | FSH | 8.9 mIU/ml | | |
| | Estradiol | 67 pg/ml | | |
| May 2003 | Anti-adrenal antibodies | negative | | |
| | Estradiol periovulatory | 139 pg/ml | | |
| | DHEA | 132 ng/dl | (130-980) | |
| | DHEA-S | 79 mcg/dl | (52-400) | |
| | Testosterone total | 34 ng/dl | (20-76) | |
| | free | 3 pg/ml | (1-21) | |
| July 2003 | DHEA TREATMENT START | | | |
| | DHEA | 296 ng/dl | (130-980) | |
| | DHEA-S | 366 mcg/dl | (52-400) | |
| | Androstenedione | 121 ng/dl | (65-270) | |
| September 2003 | Estradiol periovulatory | 268 pg/ml | | |
| October 2003 | FSH | 14.7 mIUI/ml | | |
| | Estradiol | 44 pg/ml | | |
| | periovulatory | 224 pg/ml | | |
| November 2003 | FSH | 17 mIU/ml | | |
| | Estradiol | 38 pg/ml | | |
| December 2003 | DHEA | 278 ng/ml | (130-980) | |
| | DHEA-S | 270 mcg/dl | (52-400) | |
| | Testosterone total | 25 ng/ml | (20-76) | |

TABLE 5-continued

Relevant laboratory results

| Date | TEST | RESULT (Normal values)* | | COMMENTS |
|---|---|---|---|---|
| | free and weekly bound | 4 ng/dl | (3-29) | |
| | free | 2 pg/ml | (1-21) | |
| January 2004 | FSH | 18 mIU/ml | | |
| | FSH | 9.6 mIU/ml | | 4th IVF |
| | Estradiol | 56 pg/ml | | CYCLE START |
| August 2004 | MID_PREGNANCY DHEA | 74 ng/dl | (135-810) | |
| | DHEA-S | 27 mcg/dl | (**) | |
| October 2004 | | | | DELIVERY |
| December 2004 | DHEA-S | 52 mcg/dl | (44-352) | |

*Laboratory tests were performed at varying laboratories
**No Pregnancy levels available from laboratory

TABLE 6

ACTH stimulation test

| HORMONE | BASELINE | +30 MINUTES | +60 MINUTES |
|---|---|---|---|
| DHEA-S (mcg/ml) | 87 | 88 | 83 |
| Cortisol total (mcg/dl) | 15 | 26 | 27 |
| Testosterone total (ng/dl) | 28 | 32 | 33 |
| free and weakly bound | 5 | 5 | 5 |
| free | 3 | 3 | 3 |

This case report presents further evidence for DHEA deficiency as a cause of female infertility and as a possible causative agent in the aging processes of the ovary. It also presents further confirmation of the value of DHEA substitution whenever the suspicion exists that ovaries may be lacking of DHEA substrate. Finally, this case report raises the important question what the incidence of adrenal 17,20-desmolase (P450c17) deficiency is in women with prematurely aging ovaries.

EXAMPLE 6

Increase Male Fetus Sex Ratio

Androgenization of females with dehydroepiandrosterone (DHEA), as we recently have been utilizing in the fertility treatment of women with diminished ovarian reserve, in combination with the investigation of spontaneous, versus in vitro fertilization (IVF)—conceived, pregnancies allows for an investigation of the basic theory of sex allocation and its possible pathophysiologic mechanisms.

The treatment protocol for long-term supplementation with DHEA that may improve oocyte and embryo quantity, quality, pregnancy rates and time to conception in women with diminished ovarian reserve, involves 25 mg of micronized, pharmaceutical grade DHEA, TID will usually uniformly raise levels of unconjugated DHEA above about 350 ng/dl, and, therefore, raise baseline testosterone. Estradiol baseline levels may also be raised.

A retroactive review of either ongoing or delivered pregnancies beyond 20 weeks gestational age, conceived while on DHEA treatment for at least 60 days, revealed 23 women. A total of 19 pregnancies were recorded with 16 singleton and 3 twin pregnancies. The medical records of all 19 women were reviewed in order to determine whether they conceived spontaneously, defined as including pregnancies conceived with intrauterine inseminations, or by IVF. If conception had occurred by IVF, it was recorded whether fertilization was spontaneous or by intracytoplasmic sperm injection (ICSI).

As a control group, seven women were selected who had undergone one IVF cycle with preimplantation genetic diagnosis (PGD), while for at least 60 days on DHEA supplementation, but had not conceived. The PGD data, defining each embryo's gender, were recorded. Statistics were performed using a binomial runs test, comparing seen distributions with an expected distribution of 50 percent, with $p<0.05$ defining significance.

Sixteen singleton pregnancies resulted in 11 males and 5 females (N.S.). Two of three twin pregnancies were heterozygous and one homozygous. If outcomes of both heterozygous twins, but of only one homozygous twin, were added, the final gender distribution was 15 males and 6 females ($p=0.078$, N.S.)

Amongst six pregnancies, spontaneously conceived, the distribution between female and male offspring was equal, at three and three, respectively. Whereas amongst the remaining 15 offspring, which were products of pregnancies achieved through IVF, the distribution was 12 males and 3 females ($p=0.035$). Only one IVF patient failed to have ICSI. Amongst women undergoing IVF and PGD, 53 embryos were analyzed from 17 IVF cycles, all having undergone ICSI. The gender distribution was not significantly skewed, with 27 being male and 26 female.

This study allows for the dissection of the conception process into its various stages and, therefore, permits an analysis of, not only the basic question whether androgenization does indeed, affect gender selection in the human, but also how such a selection may be influenced.

The here presented data, demonstrating a strong trend towards significance overall, and significance ($p=0.035$) amongst IVF patients, suggest, convincingly that gender determination may be influenced by hormonal environment. Assuming an effect of androgens on gender selection, such women should give birth to a preponderance of male offspring. Confirming such a finding could present a potential additional explanation for the evolutionary preservation of PCOS in practically all human races.

EXAMPLE 7

Increase Pregnancy Rates

In an additional study, a retrospective analysis of a 190 women with diminished ovarian function above 30 years old, who were treated between 1999 and December 2005 was completed to assess the impact of DHEA supplementation on the time interval to the establishment of pregnancy.

A prequalification for each patient's diagnosis of diminished ovarian function was either a sub-diagnosis of premature ovarian aging (POA) or a sub-diagnosis of diminished ovarian reserve (DOR). POA was, in turn, defined as baseline follicle stimulating hormone (b-FSH), on Day 2/3 of a cycle as <12 mIU/ml, but exceeding the 95% CI of the mean value for the patient's age group.

Specifically, this meant b-FSH≧7.4 mIU/ml at age 30-34 years and ≧8.6 mIU/ml at age≧35 years. DOR, in turn, was defined as b-FSH≧12 mIU/ml and/or a baseline estradiol level≧75 pg/ml. 49 patients were confirmed with POA and 52 patients were confirmed with DOR, creating a control group of 101 women. Because of potential impending loss of ovarian function in the control group women, the control group women were treated with IVF as soon as possible.

During the time studied, the study group consisted of 89 patients, with diminished ovarian function (POA 24, DOR 65). Each person in the study group was placed on DHEA supplementation. The DHEA supplementation included administering about 25 mg of (pharmaceutical grade) micronized DHEA, three times daily, for up to about four months (mean 3.8±0.3 months). In contrast to the control group, women in the study group did not enter IVF right away. This delay of IVF treatment allowed the possibility of spontaneously conceived pregnancies. Those patients who did not conceive spontaneously within four months of beginning DHEA entered IVF.

Methods of Example 7

Ovarian stimulation was identical for study and control groups and comprised microdose agonist flare, followed by maximal dosage gonadotropin stimulation, using about 300-450 IU of FSH and about 150 IU of HMG. Study patients received DHEA continuously until a positive pregnancy test was obtained or until the patient dropped out of treatment. DHEA and DHEAS levels were monitored monthly, and patients were interviewed at each visit about adverse reactions to DHEA supplementation. Because of the dynamics of the DHEA treatment algorithm, at the time of this data analysis, 16 women in the study group were at various stages of DHEA supplementation, prior to any intervention, 9 women received ovarian stimulation while on DHEA, and 64 have undergone an IVF cycle.

In order to assess the impact of DHEA supplementation on time interval to the establishment of pregnancy, this study was designed as a life-table analysis, measuring not only total pregnancy rates but also the time between initial presentation and end of last treatment intervention.

Each recorded clinical pregnancy, defined as positive fetal cardiac activity on ultrasound examination after 6 weeks, was recorded as a positive outcome. Patients who continued treatments beyond the study period or stopped treatments were considered right censored data at the end of the study period, or at treatment cessation, respectively.

The following factors were compared between study and control groups: female age, months of infertility prior to initial visit, length of treatment from first presentation, gravidity, race, IVF treatments, maximal baseline FSH levels, maximal baseline estradiol levels, IVF cycle cancellation rates, oocyte numbers, number of embryos transferred, implantation rates, cumulative clinical pregnancy rates and miscarriage rates.

A Cox regression analysis was used to evaluate time-to-event. The model that we used stratified for level of ovarian reserve (POA and DOR) and adjusted for age, day 3 FSH, fertility treatments (none, Intrauterine Insemination and controlled ovarian hyperstimulation (IUI/COH), or IVF) and race/ethnicity. A trend in pregnancy rates over months of DHEA exposure with an interaction term for time and DHEA months of exposure was tested. SPSS for Windows, Standard version 10.0.7 (SPSS Co. Chicago, Ill.) was utilized for data analysis. Continuous outcomes are presented as mean±1 standard error. Univariate comparisons were made with analysis of variance, or by using Fisher's exact test.

Results of Example 7

Table 7 summarizes patient characteristics. As can be seen, study patients were slightly older than the controls at 41.6±0.4 and 40.0±0.4 years (p<0.05) respectively. Pregnancy histories, duration of infertility and of treatment (in months) were similar between the two groups. Controls represented a non significant larger proportion of minorities, received more treatment cycles overall (1.6±0.9 versus 1.3±1.0; p<0.05) and differed significantly in the various treatments they received (p<0.001). Study patients demonstrated a non-significantly higher b-FSH 16.0±1.2 13.6±1.0 mIU/ml) and a significantly higher baseline estradiol level (366±53 versus 188±24 pml/ml; p<0.05). More women in the study group had b-FSH≧10 mIU/ml that amongst controls (73% versus 51.5%; p<0.05). In addition, greater proportion of women in the study group had DOR (p<0.005).

TABLE 7

Characteristics of DHEA Treated and Controls

|  | DHEA | Control | p |
|---|---|---|---|
| N | 89 | 101 |  |
| Age | 41.8 ± 0.4 | 40.0 ± 0.4 | <0.05 |
| Months Infertility | 44.5 ± 4.8 | 41.8 ± 6.9 | ns |
| Months from First Visit | 8.1 ± 0.7 | 7.8 ± 1.0 | ns |
| Race |  |  | ns |
| White | 62 (70.5%) | 57 (56.4%) | — |
| Hispanic | 7 (7.9%) | 12 (11.9%) | — |
| Black | 9 (10.2%) | 14 (13.9%) | — |
| Asian | 11 (12.5%) | 18 (17.8%) | — |
| Cycles of Treatment | 1.3 ± 1 | 1.6 ± 0.8 | <0.05 |
| Treatment |  |  | <0.01 |
| No Treatment | 16 (18.2%) | 0 (0%) | — |
| IUI/COH | 9 (10.2%) | 0 (0%) | — |
| IVF | 64 (71.8%) | 101 (100%) | — |
| Day 3 FSH (mIU/ml) | 16.0 ± 1.2 | 13.6 ± 1.0 | ns |
| Day 3 E2 (pmol/ml) | 366 ± 53 | 188 ± 24 | <0.05 |
| Ovarian Function |  |  | <0.005 |
| POA | 24 (27%) | 49 (43.5%) | — |
| DOR | 65 (73%) | 52 (51.5%) | — |

Table 8 lists the results of univariate comparisons of treatment outcomes. As can be seen, confirming a more severe degree of diminished ovarian function, the study group produced significantly fewer oocytes, normal day-3 embryos (2.4±0.03 versus 3.5±0.2; p<0.05) and transferred embryos (2.1±0.2 versus 2.7±0.2; p<0.05). Cycle cancellations were, however, nominally higher among the controls (25.7% versus 14.3%).

TABLE 8

Univariate Comparison of Results Between Control and DHEA Treated Patients

|  | DHEA | Control | p |
|---|---|---|---|
| N total; (IVF) | 69 (64) | 101 |  |
| Months of DHEA | 3.8 ± 0.3 | — | — |
| Cancellation (IVF) | 9/63 (14.3%) | 26/101 (25.7%) | ns |
| Oocytes | 3.9 ± 0.4 | 5.8 ± 0.5 | <0.01 |

TABLE 8-continued

Univariate Comparison of Results Between
Control and DHEA Treated Patients

|  | DHEA | Control | p |
|---|---|---|---|
| Normal Day 3 embryos | 2.4 ± 0.3 | 3.5 ± 0.2 | <0.05 |
| Transferred embryos | 2.1 ± 0.2 | 2.7 ± 0.2 | <0.05 |
| Positive hCG (>25 mIU/ml) | 26/88 (30%) | 18/101 (18%) | ns |
| Implantation (FH/Embryos trans) | 13/101 (11.4%) | 11/148 (6.9%) | ns |
| Clinical Pregnancy | 25/89 (28.1%) | 11/101 (10.9%) | <0.01 |
| No Treatment | 6/16 (35.3%) | — | — |
| IUI/COH | 6/9 (66.7%) | — | — |
| IVF | 13/64 (20.6%) | 11/101 (11.9%) | ns |
| Miscarriage (per clinical Pregnancy) | 5/25 (20%) | 4/11 (38%) | ns |

Overall clinical pregnancy rates were significantly higher in study patients (28.1% versus 10.9%; p<0.01). Remarkably, almost one-half of all pregnancies in the study group were established spontaneously before IVF start; however, even within the patients reaching IVF, there was a strong trend towards higher pregnancy rates (20.6% versus 11.9%).

Approximately two months after initiation of treatment the mean DHEA and DHEAS levels at cycle day 2 blood drawing were in the low normal ranges. Few patients reported side effects from DHEA use. These included mild transient acne on the face, chest or back, oily skin and mild hair loss. No facial or body hair growth was reported, nor was there any deepening of voice. Some patients reported an increased sense of well-being or increased libido.

Figure 6:
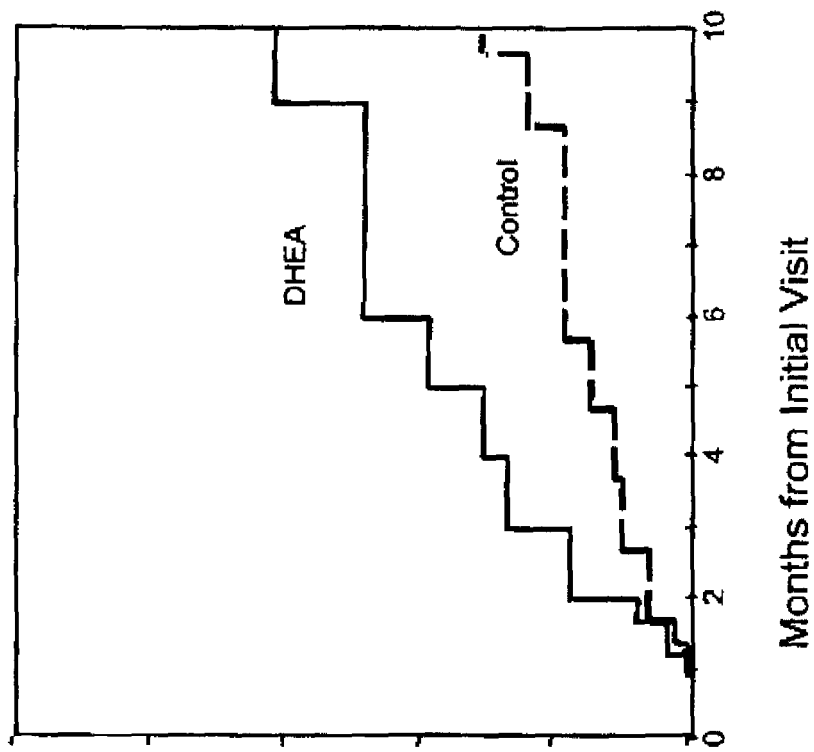
FIG. 6 is a graph showing cumulative pregnancy rate of time from initial visit to clinical pregnancy or censor by DHEA for women with premature ovarian aging.
Figure 7:
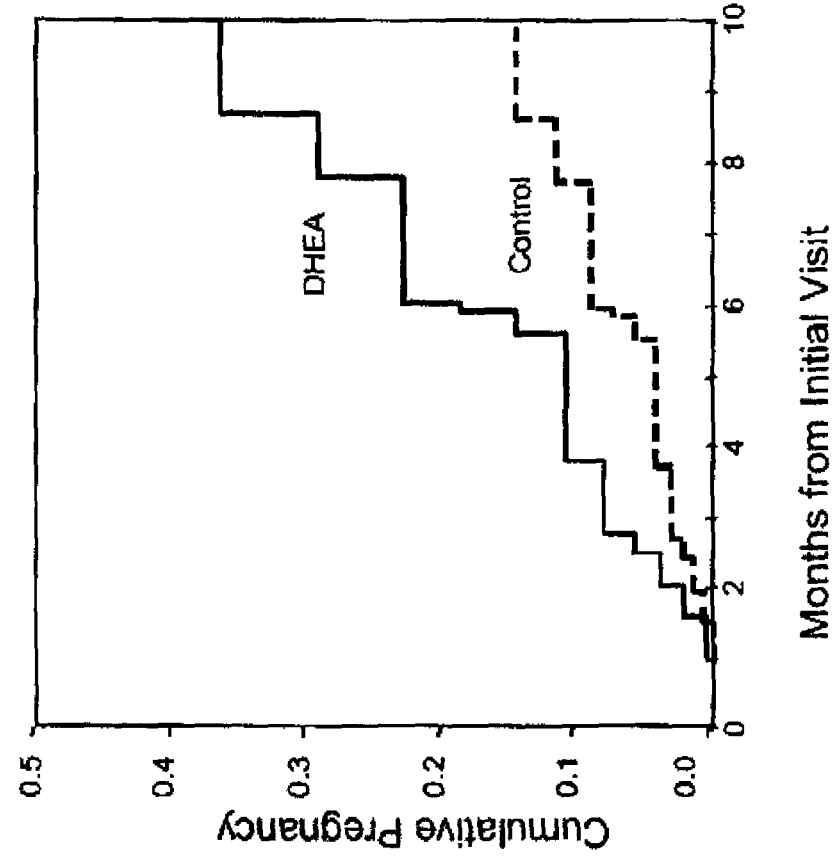
FIG. 7 is a graph showing cumulative pregnancy rate of time from initial visit to clinical pregnancy or censor by DHEA for women with diminished ovarian reserve.

Cox regression of months from initial visit until clinical pregnancy, adjusted for age, race/ethnicity, fertility treatment, and stratified for level of ovarian reserve (POA and DOR), revealed that DHEA treated patients had a significantly increased proportional hazards ratio for clinical pregnancy relative to controls (HR 3.8; 95% CI 1.2 to 11.8; p<0.05). FIGS. 6 and 7 show proportional hazard curves of clinical pregnancy by months from their initial visit. Specifically, FIG. 6 is a graph showing cumulative pregnancy rate of time from initial visit to clinical pregnancy or censor by DHEA for women with premature ovarian aging, and FIG. 7 is a graph showing cumulative pregnancy rate of time from initial visit to clinical pregnancy or censor by DHEA for women with diminished ovarian reserve. The curves reveal a rapidly separating increase in cumulative clinical pregnancies between study and control groups from the first month on.

Extended Cox models with correction for time dependent variables "months of DHEA use" and "Treatment" did not decrease the proportional hazards estimation of pregnancy associated with DHEA treatment (HR 4.8; 95% CI 1.6 to 14.2; p=0.005).

Discussion of Example 7

A significantly increased pregnancy rate in a group of women with a very poor prognosis for pregnancy has been determined. A strength of this study is its rather large sample size.

Spontaneous background pregnancy rates in average infertile women occur at an approximate rate of one to two percent per month. Spontaneous pregnancies in women with clear evidence of diminished ovarian function are obviously an even rarer occurrence. Given the degree of loss of ovarian reserve in this group, a 28.1% cumulative pregnancy rate in a patient population, previously largely referred into oocyte donation, is quite remarkable.

DHEA supplementation can improve ovarian function in women with diminished ovarian reserve. Study and control patients received identical ovarian stimulation protocols during IVF cycles. IVF protocols during the study years 1999-2005 did not significantly change during this time. Specifically, the protocols may include administering microdose agonist/gonadotropin stimulations in women with diminished ovarian reserve.

The mechanism of DHEA's action on the ovary remains speculative. DHEA declines with age and DHEA supplementation may simply improve the substrate pool for steroidogenesis, since DHEA is a precursor hormone for estradiol and testosterone.

Androgens may, however, influence ovarian follicular growth not only by acting as metabolic precursors for steroid production, but also by serving as ligands for androgen receptors or by other, non-classical mechanisms. During ovulation induction with exogenous gonadotropins, DHEA is the prehormone for up to 48% of follicular fluid testosterone, which is, in turn, the prehormone for estradiol. There is evidence that androgens act, together with FSH, to stimulate follicular differentiation. Androgens are also known to promote steroidogenesis and follicular recruitment and to increase insulin-like growth factor (IGF-1) in the primate ovary. DHEA-treated rat ovaries express elevated levels of IGF-1 in pre-antral and early antral follicles.

A transient increase in IGF-1 in patients undergoing exogenous gonadotropin ovulation induction after pretreatment for only eight weeks of DHEA has previously been reported and it was hypothesized that the effect of DHEA on ovulation induction might have been mediated by increased IGF-1.

Higher baseline testosterone levels have been associated with improved IVF outcomes, and higher serum testosterone has been correlated with higher oocyte numbers retrieved at IVF. Some authors have suggested that improved outcomes in women with diminished ovarian reserve after co-treatment with aromatase inhibitors may be the consequence of induction of FSH receptors on granulosa cell by androgens. The resultant ovarian response may then lead to improved follicular survival, increased follicle numbers and higher estradiol levels during stimulation, as classically also observed in polycystic ovarian disease.

Human polycystic ovaries have been described as representing a "stock-piling" of primary follicles, secondary to an alteration at the transition from primordial to primary follicle. It is possible that DHEA treatment may create PCO like characteristics in the aging ovary. Long term exogenous androgen exposure can induce PCO-like histological and sonographic changes. Androgens have been reported to suppress apoptosis. Exogenous DHEA exposure may occur during the first two weeks of pregnancy.

In summary, a significant increase in the odds of pregnancy among DHEA treated women has been determined. This increase appears to be rapid in onset and to continue progressively within eight months of initial observation.

EXAMPLE 8

Decrease Miscarriage Rates

In a further study, women (i.e, women with progressively declining ovarian function) with diminished ovarian reserve were administered DHEA to assess the effect of DHEA on miscarriage rates.

Since women with diminished ovarian reserve produce only few oocytes and embryos, preimplantation genetic diagnosis (PGD) in association with IVF is only rarely indicated, and, indeed, may be detrimental. To accumulate direct ploidy data on a large enough statistical patient sample is, therefore, difficult. Because spontaneous miscarriage rates are reflective of aneuploidy rates, the study presented herein includes pregnancy outcomes after DHEA supplementation from two independent North American fertility centers and compares those with age-specific national outcome data after IVF.

Materials and Methods of Example 8

Based on reported clinical experiences, the indications for DHEA supplementation have changed over the years, with women above age 40 since 2007 receiving routine supplementation, and younger women receiving supplementation only selectively. This means that under age 40 women receive supplementation only if they demonstrate elevated age-specific baseline follicle stimulating hormone (FSH) levels and have demonstrated in at least one cycle inappropriately low oocyte yield with in vitro fertilization (IVF) following standard ovarian stimulation with gonadotropins.

DHEA supplementation involves the use of pharmaceutical grade micronized DHEA at a dosage of about 25 mg, three times daily. Patients are on DHEA supplementation for at least about two months prior to oocyte retrieval. This period of minimal pretreatment is based on the recognition that at two months pregnancy curves between DHEA pretreated and control patients statistically diverge. DHEA is maintained until pregnancy is established and is discontinued with positive pregnancy test.

Toronto West Fertility Associates, in Toronto, Canada, started utilizing DHEA independent of the use of DHEA at the Center for Human Reproduction (CHR) in New York, N.Y. In December of 2007, Toronto's medical director forwarded a detailed electronic record of the center's all-inclusive DHEA experience for analysis to CHR. This study, therefore, reports on the miscarriage rate of pregnancies, independently established under DHEA supplementation at both fertility centers, and compares these rates, age-stratified, to miscarriage rates reported in a national IVF data base in the U.S. for the year 2004. The definitions of clinical pregnancy, and of miscarriage, used herein follow the reporting requirements of this national data base, defining a clinical pregnancy as a pregnancy, confirmed by ultrasound examination.

It is important to note that DHEA supplemented patients universally suffered from severely diminished ovarian reserve. Their pregnancy expectations were, therefore limited. Patients who conceived a clinical pregnancy, thus, represented only a minority of DHEA supplemented patients at both centers.

Miscarriage rates of DHEA supplemented patients were compared with national IVF outcome statistics, reported annually under Federal mandate by the Centers for Disease Control. The data utilized for this study reflect 2004 United States national statistics. Pregnancy and miscarriage rates at the two centers were pooled after confirmation of homogeneity of variance. Common odds ratios of the pooled miscarriage rates among age stratified pregnant patients were compared between the pooled rates and the 2004 US national rates utilizing the Mantel-Haenszel common odds ratio. Statistical analyses were performed using SPSS Windows, standard version 15.0.

Results of Example 8

New York reported 40 and Toronto 33 DHEA pregnancies, for a combined DHEA pregnancy experience of 73 pregnancies. New York reported six miscarriages, for a clinical miscarriage rate of 15.0%, and Toronto reported five miscarriages, for a clinical miscarriage rate of 15.2%, for a combined miscarriage rate of 11/73 (15.1%). For analysis, the 2004 miscarriage rate in the national U.S. registry of 17.6% was used.

Figure 8:
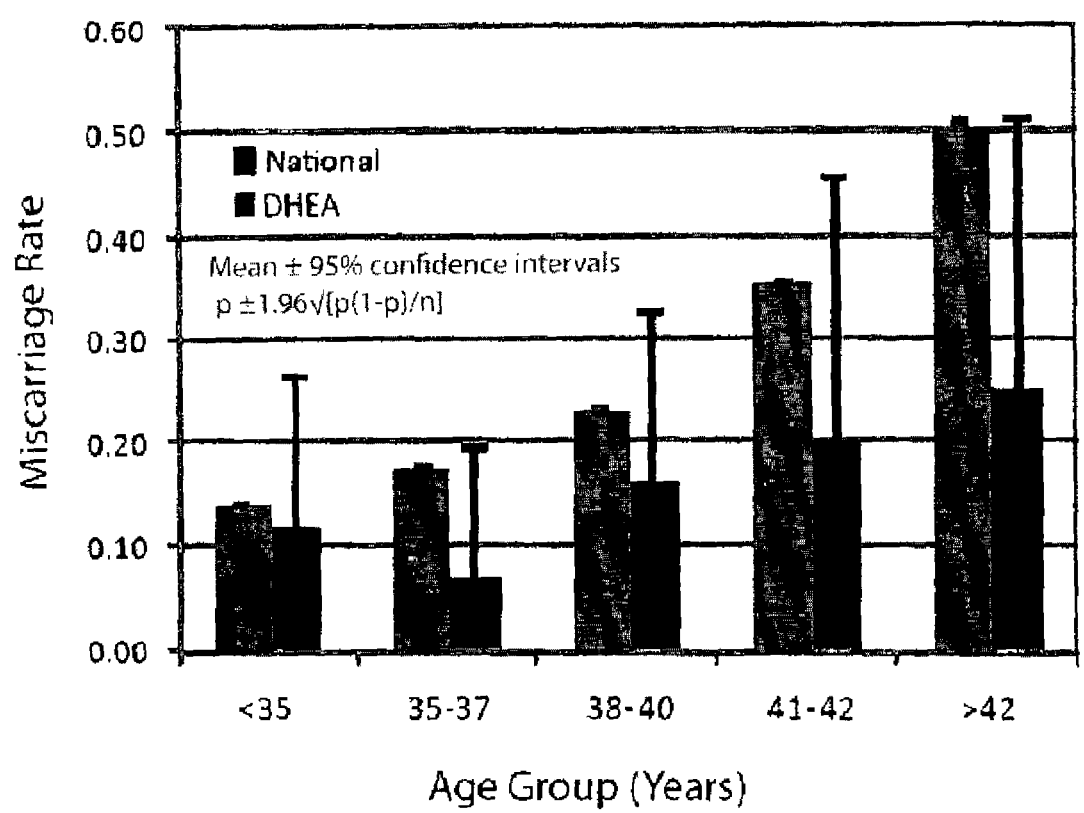
FIG. 8 is a graph showing a comparison of miscarriage rates between DHEA treated infertility patients and 2004 national US IVF data.

As seen in Table 9 (below) and FIG. 8, miscarriage rates after DHEA supplementation, stratified for age, were lower at all ages [OR 0.49 (0.25-0.94; p=0.04)]. The decrease in miscarriage rate was, however, especially apparent above age 35 years.

TABLE 9

Age-stratified pregnancy and miscarriage rates

| | Age (years) | | | | |
|---|---|---|---|---|---|
| | <35 | 35-37 | 38-40 | 41-42 | >42 |
| DHEA Pregnancies | | | | | |
| NY | 10 | 5 | 6 | 10 | 9 |
| TO | 7 | 10 | 13 | 0 | 3 |
| Miscarriages | | | | | |
| NY | 1 | 0 | 0 | 2 | 3 |
| TO | 1 | 1 | 3 | 0 | 0 |
| Misc. Rate (%) | | | | | |
| NY | 10.0 | 0.0 | 0.0 | 20.0 | 33.3 |
| TO | 14.3 | 10.0 | 23.1 | — | 0.0 |
| TOTAL | 11.8 | 6.7 | 15.8 | 20.0 | 25.0 |
| (±95% CI) | (15.0) | (13.0) | (16.0) | (25.0) | (25.0) |
| NATIONAL | | | | | |
| Misc. Rate (%) | 14.0 | 17.1 | 23.1 | 36.6 | 50.1 |
| (±95% CI) | (1.0) | (1.0) | (1.0) | (2.0) | (5.0) |
| Decrease in Misc. Rate with DHEA (%) | −15.7 | −60.8 | −31.6 | −45.3 | −50.1 |

Miscarriage rates after DHEA supplementation, stratified for age, were lower at all ages [OR 0.49 (0.25-0.94; p = 0.04)]. The decrease in miscarriage rate was, however, especially apparent above age 35 years.
NY, - Center for Human Reproduction, New York;
TO, - Toronto West Fertility Associates, Toronto, Canada Discussion of Example 8

The data reported herein demonstrate a significantly diminished miscarriage rate in women with diminished ovarian reserve, in comparison to a standard IVF population, if pretreated for at least two months with DHEA. Specifically, as shown in Table 9, the percentage decrease in miscarriage rate with DHEA supplementation for women with diminished ovarian reserve under the age of 35 was 15.7, for women between the ages of 35-37 was 60.8, for women between the ages of 38-40 was 31.6, for women between 41-42 was 45.3, and for women above the age of 42 was 50.1. This effect appears particularly pronounced above age 35 years.

This is a remarkable observation that is further strengthened by the fact that, due to their severely diminished ovarian reserve, the studied DHEA supplemented women represent a highly unfavorable patient population. It has been reported that women with diminished ovarian reserve experience exceedingly high miscarriage rates, far in excess of standard IVF patients with normal ovarian reserve. For example, miscarriage rates of 57.1 percent under age 35 in women with diminished ovarian reserve, 63.5 percent between ages 35 and 40 in women with diminished ovarian reserve, and as high as 90 percent above age 40 years in women with diminished ovarian reserve have been reported. Considering the fact that national U.S. IVF data represents only a minority of women with diminished ovarian reserve, the finding that DHEA supplementation significantly reduced miscarriage rates in all age groups below those of an average national IVF population is remarkable.

While on first glance the larger degree of reduction in miscarriage rate in older women may surprise, it should not. Aneuploidy rates increase with age and, indeed, age 35 is generally considered the age cut off, where more aggressive prenatal genetic screening becomes indicated. If DHEA affects aneuploidy rates, then one would, indeed, expect a much larger beneficial effect after, rather than before, age 35, because older women usually produce fewer embryos, and the relative benefit from a decrease in aneuploidy rate on the number of euploid embryos transferred in IVF will, therefore, increase with advancing female age.

Aneuploidy is a frequent finding even in young women. As women age, the prevalence of aneuploidy increases further, at times reaching close to 90 percent in women above age 40. Interestingly, women who demonstrate clinical evidence of prematurely aging ovaries do not also demonstrate prematurely enhanced aneuploidy rates. They maintain the expected age-specific aneuploidy, dictated by their chronological age, and therefore, experience similar implantation— and pregnancy rates, though, because of decreased oocyte and embryo numbers, reduced cumulative pregnancy rates. It, therefore, should not surprise that women under age 35, even though suffering from a significant degree of prematurely diminished ovarian reserve, did not benefit as much from DHEA as older women.

This study demonstrates a statistical association between DHEA supplementation and decreased miscarriage rates. The reported data offers enough circumstantial evidence to suggest that DHEA both decreases miscarriage rates and reduces aneuploidy rates in human embryos.

The presented data helps to explain why DHEA supplementation increases egg and embryo quality, improves pregnancy rates and speeds up time to conception. Egg and embryo quality is, of course, at least partially a reflection of ploidy. Embryos with less aneuploidy can be expected to lead to more pregnancies, resulting in more, and quicker, conceptions.

The concept of embryo selection by improving ploidy has been the basis for attempts at improving pregnancy rates and reducing miscarriage rates via preimplantation genetic screening (PGS). The utility of PGS has recently, however, been seriously questioned since, especially in women with only few embryos, the necessary embryo biopsy may cause more harm to pregnancy chances than the potential benefits, derived from embryo selection offer. DHEA supplementation, therefore, may represent a much simpler, more cost effective and, most importantly, safer method of embryo selection for ploidy than PGS.

It should not be overlooked that the here presented study addresses only infertile women with a significant degree of diminished ovarian reserve. As already noted, they represent a very unfavorable patient population, with exceedingly high expected miscarriage rates. However, even though infertile women with normal ovarian reserve have significantly lower miscarriage rates, they in general still experience higher miscarriage rates than the average population. While the here-reported miscarriage rates in DHEA patients are remarkably low, caution should, therefore, be exercised in concluding automatically that the observed DHEA effect can be extrapolated to a general population. It is, however, quite remarkable that the here-reported miscarriage rates in women with severely diminished ovarian reserve at both study centers, stratified by age, were practically identical to those reported for the general population.

Based on the hypothesis that congression failure (gross disturbances in chromosome alignment on the meiotic spindle of oocytes) results from the complex interplay of signals regulating folliculogenesis (thus increasing the risk of non-disjunction errors), it has been suggested that it may be possible to develop prophylactic treatments that can reduce the risk of age-related aneuploidy. DHEA may, indeed, be a first such drug.

Assuming such a more universal effect of DHEA supplementation on aneuploidy rates, supplementation should also be investigated for infertile women in general and, maybe, even for normally fertile women above age 35, who could receive DHEA as a routine preconception supplement, akin to prenatal vitamins. Should efficacy of DHEA supplementation in such a general population be proven, the potential significance of such a finding on public health could be considerable.

As stated herein, and supported at least by the examples herein, DHEA supplementation for at least two months increases egg numbers and egg quality and, therefore, also embryo numbers and quality. DHEA also improves spontaneous pregnancy rates, IVF pregnancy rates, cumulative pregnancy rates and time to conception in prognostically otherwise highly unfavorable patients. Further, DHEA statistically reduces miscarriage rates, probably, at least partially, by reducing aneuploidy rates. Moreover, DHEA probably also increases the male/female birth ratio. The effects of DHEA increase over time, reaching peaks after approximately four to five months of supplementation. It is suggested that the peak occurs at four to five months because this time period is similar to the time period of a complete follicular recruitment cycle.

EXAMPLE 8 Continued

Background

Dehydroepiandrosterone (DHEA) supplementation may improve selected aspects of ovarian function in women with diminished ovarian reserve.

DHEA supplementation improves response to ovarian stimulation with gonadotropins by increasing oocyte yield and embryo numbers. DHEA effects increase over time, reaching peaks after approximately four to five months of supplementation. DHEA, however, also increases oocyte and embryo quality, spontaneous pregnancy rates in prognostically otherwise highly unfavorable patients on no further active treatments, pregnancy rates with in vitro fertilization (IVF), time to pregnancy and cumulative pregnancy rates.

DHEA may effect insulin-like growth factors (IGF-1)-mediated. On the other hand, because DHEA effects peak at four to five months, a time period similar to the complete follicular recruitment cycle, we have speculated that DHEA may effect follicular recruitment, possibly mediated via suppressive effects on apoptosis. Additionally, DHEA may reduce aneuploidy in embryos.

Since approximately 80 percent of spontaneous pregnancy loss is the consequence of chromosomal abnormalities, reduced aneuploidy should also reduce miscarriage rates. As women get older, and ovarian function progressively declines, miscarriage rates rise because of increasing aneuploidy. If DHEA, indeed, were to beneficially affect ploidy, DHEA supplementation should, as an additional benefit in older women with severely diminished ovarian reserve, therefore, result in reduced miscarriage rates.

Since women with diminished ovarian reserve produce only small oocyte and embryo numbers with IVF, preimplantation genetic diagnosis (PGD) in association with IVF is only rarely indicated, and, indeed, may be detrimental. To accumulate direct embryo ploidy data in such patients is, therefore, difficult. Seeking alternatives, we were attracted by the fact that spontaneous miscarriage rates to such a large degree reflect aneuploidy rates. This study, therefore, presents pregnancy outcomes after DHEA supplementation from two independent North American fertility centers and compares those with age-specific national USA outcome data after IVF.

Methods

DHEA supplementation: After approval by the center's institutional review board, the Center for Human Reproduction (CHR) in New York City has been utilizing DHEA supplementation in women with diminished ovarian reserve since 2004. Based on reported clinical experiences, the indications for such supplementation have changed over the years: In initial stages, only older women, above age 42, were supplemented and only if they had failed at least one IVF cycle and less than 4 oocytes had been retrieved in confirmation of ovarian resistance to stimulation. By mid-2005, indications were expanded to all women above age 40 with evidence of ovarian resistance and a history of one failed prior IVF cycle. By early 2006 indications were further expanded to women under age 40 if they demonstrated elevated baseline follicle stimulating hormone (FSH) levels above 10mIU/ml and had shown ovarian resistance in at least one failed IVF cycle. By mid-2006 FSH baseline criteria were changed from absolute FSH elevations to elevations in age-specific FSH levels. All women above age 40 have been offered routine supplementation since January 2007, while younger women, under age 40, are continuing to be only selectively supplemented if demonstrating elevated age-specific baseline follicle stimulating hormone (FSH) levels and, as previously reported, inappropriately low oocyte yield in at least one IVF cycle.

DHEA supplementation in all patients involves oral, pharmaceutical grade micronized medication at a dosage of 25 mg, three times daily (TID). Only morbidly obese women receive an increased daily dosage of 100 mg and no such women were involved in this study. This supplementation dosage was chosen and is continued to be used since DHEA use ahs shown to result in only minor side effects. Limited patient volume and funding sources have prevented dose response studies and 25 mg DHEA TID daily has, therefore, remained the only standard treatment dosage. Patients receive at least two months of DHEA supplementation prior to oocyte retrieval, unless they conceive spontaneously during that time period. This minimum pretreatment period is based on the recognition that at two months pregnancy curves between DHEA pretreated and control patients statistically diverge. DHEA is maintained until pregnancy, and is discontinued with second positive pregnancy test.

Collaboration between centers: The utilization of DHEA at the Toronto based center was independently initiated, after that center's medical director (E.R.) at a lecture (by N.G.) learned about the New York center's DHEA experience. Toronto's data accumulation was unknown to the New York center until in December of 2007, unsolicited, a detailed electronic record of Toronto's DHEA experience was forwarded to New York with a request for combined analysis. The Canadian data were sequestered to the New York center's confidential research data base, which is restricted to one computer. Confidentiality and anonymity of submitted records was, therefore, maintained.

Control population: This study reports on miscarriage rates, at both fertility centers, independently established under DHEA supplementation, and compares these rates, age-stratified, to miscarriage rates reported in a national USA IVF outcome data base, which involves unselected infertility patients. While study populations at the New York and Toronto centers, thus, involve women with significantly DOR, the national control data reflect only a rather small percentage of women with this primary diagnosis.

DOR patients have in the past resisted prospective randomization. Two registered prospectively randomized, placebo controlled trials, one in new York City and a second in Europe, had to be abandoned for lack of enrollments (Gleicher N and Barad DH, Unpublished data, 2006 and 2007). In the absence of such prospectively controlled studies, the question arose how to establish statistically valid controls for observed miscarriage rates: A control population should involve infertile women under treatment. It also should have maximal size, vary in age distribution (to facilitate age stratification) and be all encompassing (to avoid selection biases). Since here presented DHEA data were generated in North America, a USA-based data base, fulfilling all of these criteria, was chosen.

The literature does not offer a unified definition of DOR. We define all women above age 40 years to suffer from DOR. In women under age 40 the diagnosis is only reached if age-specific ovarian function parameters.

Definitions of clinical pregnancy and of miscarriage follow the reporting requirements of this national data base, defining clinical pregnancy, as confirmed by ultrasound.

Since patients at both study centers, as a prerequisite to DHEA supplementation, had to suffer from DOR, their expectation of pregnancy success is very limited. Even considering a higher conception rate in such patients after supplementation with DHEA, conceptions will occur in only a small minority of DHEA supplemented cycles. The here reported number of consecutive pregnancies, therefore, represents a range of approximately 450 to 570 initiated DHEA treatment cycles.

Statistics: Miscarriage rates of DHEA supplemented patients were statistically compared with national IVF outcomes, reported annually under federal mandate by the Centers for Disease Control and Prevention, U.S. Department of Health and Human Services. The data utilized as controls for this study reflect 2004 United States IVF statistics, report cycle numbers, pregnancy percentages and live birth percentages, stratified for age. These detailed national data allowed calculation of number of clinical pregnancies and number of live births for each age group, since neither is offered in the original data set. We then subtracted live births from pregnancies, to derive number of failed pregnancies (i.e., all failed pregnancies were for purpose of this study considered miscarriages) overall, and in each age category. Counts of pregnancies and miscarriages were then entered into a series of two by two tables, stratified by age, and using the cross tabulation module of SPSS 15.00.

Pregnancy and miscarriage rates at both fertility centers were pooled after confirmation of homogeneity of variance. Common odds ratios of the pooled miscarriage rates among age stratified pregnant patients were compared between the pooled centers and 2004 national rates, utilizing the Mantel-Hanszel common odds ratio (tests for homogeneity of the odds ratio across layers were not significant, meeting assumption for use of this test) and using dichotomous exposure (DHEA versus controls) and dichotomous outcomes (live births versus spontaneous miscarriages), stratified by five age categories.

A secondary statistical analysis of the data was performed, by recalculating for all five investigated age groups (<35, 35-37, 38-40, 40-42 and >42 years) expected miscarriage rates for both patient groups, equalized for size. Both statistical analyses are presented in sequence and were performed using SPSS Windows, standard version 15.0.

Institutional Review Board: The investigation of DHEA in women with DOR has been repeatedly approved by the center's Institutional Review Board (IRB). Since the here reported study only involved the evaluation of (electronic) medical records, and maintained their confidentiality, the here presented study, based on a patient consent signed at time of initial registration, did not require further IRB approval. A confirmatory written statement from the chairman of the IRB is available upon request.

Results and Discussion

New York reported 40 and Toronto 33 DHEA pregnancies, for a combined DHEA pregnancy experience of 73 pregnancies. Among those pregnancies, New York registered six and Toronto five miscarriages, for clinical miscarriage rates of 15.0% and 15.2%, respectively, and a combined miscarriage rate of 11/73 (15.1%). In comparison, the total 2004 miscarriage rate in the national USA registry was 17.6%. The odds ratio and 95% confidence interval (CI), stratified for age, that a woman would miscarry was, thus, statistically significantly lower after DHEA supplementation [OR 0.49 (0.25-0.94; p=0.04), suggesting a reduction in miscarriage risk of approximately 50 percent (data not shown; Mantel-Hänszel, distributed as Chi-square with one degree of freedom, 4.285; p=0.038).

When expected miscarriage rates were compared in both patient groups, equalized for number of patients, women after DHEA supplementation demonstrated even more significant reductions in miscarriage rate (p<0.0001) suggesting an almost 80% reduction in miscarriage risk (data not shown; Mantel-Haenszel, distributed as Chi-square with one degree of freedom, 12.482; p<0.0001).

Differences between DHEA treated patients and the national IVF data became even more obvious after age-stratification. Table 9 and FIG. 8 summarize age-specific rates in numerical and graphic formats: Miscarriage rates at all ages were lower in DHEA patients than in the 2004 national IVF data. Those differences were, however, only after age 35 years pronounced.

Here reported data, after DHEA supplementation, demonstrate in women with DOR significantly lower miscarriage rates than in a standard IVF control population, a finding particularly pronounced above age 35 years. This remarkable observation is further enhanced by the well recognized and reported excessive miscarriage risk of women with DOR. Levi et al, for example, reported that women with DOR experience miscarriage rates far in excess of standard IVF patients with normal ovarian reserve: 57.1 percent under age 35; of 63.5 percent between ages 35 and 40 and as high as 90 percent above age 40 years.

Patients in the here reported study that suffered from DOR is best documented by them receiving DHEA supplementation. Under our center's DHEA protocols, except for women above age 40 years, DHEA supplementation is offered only to women who have failed at least one prior IVF cycle with retrieval of less than four oocytes and, therefore, have been designated resistant to ovarian stimulation. Moreover, younger women receive DHEA supplementation only if they also demonstrate elevated age-specific FSH levels. Finally, DHEA supplementation is voluntary, allowing for the assumption that more severely compromised patients, with poorer past IVF experiences, will more likely choose supplementation.

In contrast, USA IVF outcome data only in a minority represent women with diminished ovarian reserve. As Levi et al demonstrated, control populations, therefore, should demonstrate significantly lower miscarriage rates than our study patients. The finding that women on DHEA supplementation demonstrate in all age groups, but especially above age 35, significantly lower miscarriages than the much more favorable national IVF population is, therefore, noteworthy.

That this difference is less obvious under age 35, only strengthens the validity of the here utilized controls. Indeed, the larger degree of reduction in miscarriage rates in older women should not surprise: Aneuploidy rates increase with age, and age 35 is generally considered the cut off, when invasive prenatal genetic prenatal screening becomes indicated. Assuming a beneficial effect of DHEA on aneuploidy rates, a larger effect after age 35 should, therefore, be expected.

Levi et al, reported in women with diminished ovarian reserve above age 40 an approximately 90% miscarriage rate. Since older women produce fewer embryos, the relative benefits from decreases in aneuploidy rate on number of euploid embryos, transferred into the uterus, will increase with advancing female age.

Aneuploidy is, however, even in young women a frequent finding. In women with diminished ovarian reserve Levi et al reported an almost 60 percent miscarriage rate under age 35 years. As women physiologically age, the prevalence of aneuploidy continues to increases, reaching close to 90 percent in the mid-40ies. Premature ovarian aging, however, does not prematurely enhance aneuploidy rates, and instead maintains expected age-specific aneuploidy rates. Though demonstrating features of ovarian aging, affected women, therefore, still experience age-appropriate implantation and pregnancy rates. Because of decreased oocyte and embryo yields, they, however, do demonstrate reduced cumulative pregnancy rates. Even though significantly affected by prematurely diminished ovarian reserve, a smaller benefit from DHEA under age 35 in our study population should, therefore, not surprise.

By demonstrating in a very high risk population for spontaneous pregnancy loss a statistical association between DHEA supplementation and decreased miscarriage rates, this study does not proof causation. The study, therefore, does not prove that DHEA decreases miscarriage or aneuploidy rates in human embryos. The here reported data, however, offer enough circumstantial evidence to suggest that DHEA may, indeed, exert both of these effects and, therefore, warrant further investigations. A suggestion of improved euploidy after DHEA supplementation was, after all, also observed in human embryos.

Our center's miscarriage rates in women with DOR, prior to introduction of DHEA supplementation, were higher than the national rate seen in the here utilized control population. The program's pregnancy rates in these women were then only in low single digits. The gradual introduction of DHEA supplementation between 2004 and 2007 progressively improved pregnancy rates at our center. Increasing pregnancy numbers anecdotally suggested a concomitant decline in miscarriage rates. This observation, in turn, lead to the previously noted investigation of aneuploidy rates in embryos after DHEA supplementation, which, though statistically underpowered, was supportive of a beneficial DHEA effect on ploidy.

The New York center's pregnancy and miscarriage data, alone, were, however, not large enough to allow for statistically valid conclusions about factual miscarriage rates. Such conclusions became possible, once the independently collected Toronto data became available, and statistical analysis demonstrated that the two data sets could be unified. At this point the question arose how to control the two centers' miscarriage experiences. A statistical comparison to a large and unselected, national data set appeared appropriate.

While such a comparison cannot replace the gold standard of study design, —the prospectively randomized and placebo controlled study, the here presented data, nevertheless, offer valuable new information. We in this study used carefully vetted statistical methodologies, which are appropriate for the kind of comparisons offered. Moreover, we even performed a second statistical analysis, based on a different statistical model, which suggested an even bigger beneficial statistical effect of DHEA supplementation, increasing the potential benefit from an approximately 50 percent to an approximately 80 percent reduction in miscarriage risk.

Whether the benefit of DHEA supplementation is, indeed, 50 or 80 percent can as of this moment not be ascertained with certainty, but also should not matter. What seems of importance is the observation that DHEA supplementation, at least in women with DOR, who characteristically demonstrate abnormally high miscarriage rates, appears to significantly reduce the risk for spontaneous pregnancy loss.

Our here presented data may help to explain why DHEA supplementation increases egg and embryo quality, improves pregnancy rates and speeds up time to conception. Egg and embryo quality is, of course, at least partially a reflection of ploidy. More euploid embryos will lead to more pregnancies, thus shortening time to conception.

It is important to note that DHEA supplementation, as described, appears safe and results in only minor side effects. Since DHEA is a mild androgen but is converted into testosterone (and estradiol), it should not surprise that observed mild side effects, such as oily skin, mild acne vulgaris and hair loss are mostly androgenic in nature.

Embryo selection and improving embryo ploidy have been the rational for attempts at improving pregnancy rates and reducing miscarriage rates via preimplantation genetic screening (PGS), a concept recently seriously questioned. Here presented data suggest that DHEA supplementation may result in more cost effective improvements in ploidy without laboratory intervention.

Though infertile women with normal ovarian reserve experience significantly lower miscarriage rates than DOR patients, they still experience higher miscarriage rates than average populations. Here reported miscarriage rates in DHEA treated DOR patients are, therefore, remarkably low and practically identical to those reported for general populations. Caution should, however, nevertheless, be exercised in concluding that observed DHEA effect can automatically be extrapolated to normal, fertile populations, though such a possibility deserves further investigation. If confirmed, one could perceive DHEA as a routine preconception supplement, akin to prenatal vitamins, even in women with no fertility problems.

Conclusions

Based on the hypothesis that major disturbances in chromosome alignment on the meiotic spindle of oocytes (i.e., congression failure) result from complex interplay of signals, regulating folliculogenesis (increasing the risk of non-disjunction errors), Hodges et al suggested that it may be possible to develop prophylactic treatments which can reduce the risk of age-related aneuploidy. This study suggests that DHEA may, indeed, be a first such drug.

Should efficacy of DHEA supplementation be proven not only in infertile patients but also in general populations, the potential significance on public health could be considerably and by far exceed the more imminent utilization of DHEA in fertility practice.

EXAMPLE 9

Amidst considerable gains in the treatment of infertility, diminished ovarian reserve (DOR), whether due to physiologic aging of the ovaries or premature ovarian aging (POA), represents one of the few unresolved problem of modern infertility care. Indeed, as treatment success with other infertility problems has improved, POA patients increasingly appear to concentrate in infertility centers, and women above age 40 years have become the proportionally most rapidly growing age group in U.S. maternity wards, concomitantly graying the population under infertility treatments.

Dehydroepiandrosterone (DHEA) supplementation of women with DOR may positively impact ovarian function by increasing oocyte yields after stimulation with gonadotropins. We confirmed, and expanded on this observation by demonstrating that DHEA also improves egg and embryo quality, pregnancy rates, time to conception and reduces miscarriage rates.

Women with significant degrees of DOR usually have limited time left to conceive with use of autologous oocytes and, as two recently cancelled clinical trials (in the U.S. and Europe) demonstrate, are, therefore, reluctant to enter prospectively randomized studies that may assign them to placebo. All so far published DHEA data are, therefore, either cohort or case controlled studies, representing lower levels of evidence.

In the absence of prospectively randomized, placebo controlled studies, we searched for alternatives. Since DHEA apparently increases oocytes yield, it, likely, positively affects ovarian reserve (OR). OR has traditionally been investigated utilizing baseline follicle stimulating hormone (FSH). More recently, anti-Müllerian hormone (AMH) has, however, been suggested as a more specific reflection of OR. Its utilization in association with prematurely DOR has been advocated. This study, therefore, utilized AMH to assess OR following DHEA supplementation.

Materials and Methods of Example 9

The study is a cross-sectional analysis of 120 consecutive women with DOR in whom AMH levels were evaluated as a reflection of OR. They presented during 2007/8 to our center for initial infertility consultation. First AMH levels obtained were used for INITIAL analysis. Post DHEA initiation, exposure to the supplement ranged from 34 to 119 days (mean 73±27 days). Women with two or more consecutive AMH levels comprised patients in the longitudinal study evaluation of OR after initiation of DHEA supplementation.

Our center defines DOR in women under age 40 by elevated age-specific FSH levels, as previously reported in detail, or by universal AMH levels below 0.8 ng/ml, which approximately correlate to an FSH of 11.0 mIU/ml. Since OR declines with advancing female age, women above age 40 are uniformly assumed to suffer from DOR. Age-specific FSH levels have in association with in vitro fertilization (IVF) been demonstrated to discriminate between oocytes yields.

FSH and estradiol were evaluated by standard enzyme-linked immunoabsorbent assay (ELISA; AIA-600II, Tohso, Tokyo, Japan). Only results in assay range were considered for statistical evaluation. AMH levels were also obtained by ELISA. In short, the DSL-14400 active Müllerian Inhibiting Substance/Anti-Müllerian Hormone (MIS/AMH) Enzyme-Linked immunoabsorbent (ELISA) was utilized (Diagnostic Systems Laboratories, Inc. Webster, Tex. 77598-41217, USA). This is an enzymatically amplified two-site immunoassay, which does not cross react with other members of the TGF-β superfamily, including TGF-β1, BMP4 and ACT. Theoretical sensitivity, or minimum detection limit, as calculated by interpolation of the mean plus two standard deviations (SD) of eight replicates of the 0 ng/ml MIS/AMH Standard, is 0.006 ng/ml. Intra-assay coefficient of variation for an overall average AMH concentration is <20 percent.

Since 2007, DOR patients are at our center, before being advanced into IVF, for at least two months supplemented with pharmaceutical grade, micronized and pharmacy compounded DHEA at a dosage of 25 mg TID. DHEA is continued throughout all IVF cycles until conception (second, normally rising positive pregnancy test) or until patients discontinue treatment with autologous oocytes.

Results of Example 9

The patient population comprised 74% Caucasians, 11% African American and 15% Asian patients. A large majority (85%) were recorded with a primary diagnosis of DOR, 3% with male factor infertility and 12% with tubal factor.

Table 10 below summarizes the characteristics of the study populations, separately for cross-sectional (n=120) and longitudinal assessments (n=55). Obviously, low baseline AMH and high FSH levels are confirmatory of significant DOR in the study population. Age ranges also confirm that the younger patient population, indeed, does reflect relatively young infertility patients and, therefore, with a considerable prevalence of POA, while the older age group in principle represents women above age 40 years.

TABLE 10

Characteristics of study patients

| | Cross-sectional Study Group | Longitudinal Study Group | | | |
|---|---|---|---|---|---|
| | | All | <38 years | >38 years | p-value |
| Number of patients | 120 | 55 | 18 | 37 | |
| Age (years); mean ± SD | 39 ± 3.9 | 39 ± 3.1 | 34.9 ± 3.1 | 42.1 ± 1.2 | <0.001 |
| AMH (ng/ml); Mean ± SD | 0.32 ± 0.20 | 0.22 ± 0.22 | 0.20 ± 0.16 | 0.23 ± 0.17 | n.s. |
| Baseline FSH (mIU/ml); Mean ± SD | 15.9 ± 14.1 | 15.4 ± 9.1 | 14.2 ± 8.2 | 18.0 ± 10.8 | n.s. |
| Estradiol (pg/ml) Mean ± SD | 60.0 ± 50.0 | 52.3 ± 28.6 | 56.1 ± 13.6 | 53.2 ± 36.6 | n.s. |
| Maximal DHEA-S (microg/dL)* Mean ± SD | 474 ± 145 | 476 ± 180 | 475 ± 224 | 478 ± 180 | n.s. |

*First value obtained 30 days after initiation of DHEA supplementation

The study population was age-stratified under and above age 38 years, and further stratified, based on whether clinical pregnancy had been achieved or not. Age 38 was chosen as cut off because it has been reported to represents the beginning of accelerated decline in ovarian reserve.

Data are shown as means±standard deviation (SD) or as raw numbers and percentages. Data analysis was performed using SPSS windows, version 17.0. Demographic and biochemical data were analyzed with paired or unpaired Student's t-test. A generalized linear model was performed to evaluate the interaction of pregnancy status with days of DHEA exposure, adjusted for age at start of treatment.

DHEA utilization at our center was initially approved by the center's institutional review board (IRB) under various study protocols. After publication of a number of studies, the utilization of DHEA was in 2007 routinely expanded to all women above age 40 and to younger women with evidence of diminished ovarian reserve. Patients, nevertheless, are still mandated to sign a DHEA-specific informed consent, which, amongst other facts, advises them that DHEA by prescription is not approved by the Food and Drug Administration to treat DOR, and is in the United States commercially available as a food supplement without prescription.

The center's IRB allows for expedited review of studies, which only involve review of medical records since all patients at initial consultation sign an informed consent, which allows for such reviews for research purposes as long as the medical record remains confidential and the identity of the patient is protected.

Figure 9:
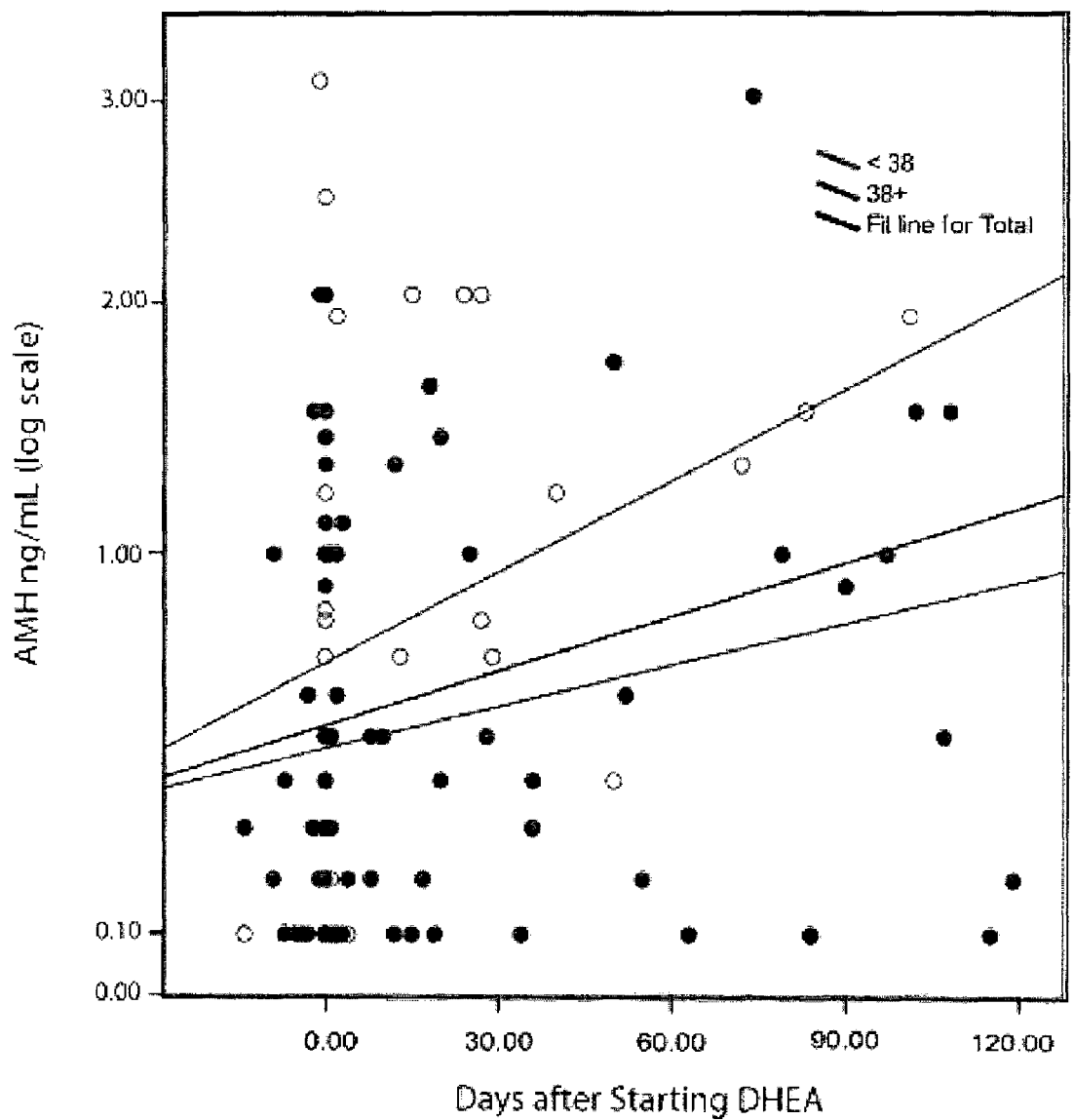
FIG. 9 is a graph showing a cross-sectional evaluation of AMH levels in correlation to time from DHEA initiation.

Cross-sectional evaluation of the whole patient population (FIG. 9) demonstrates, unadjusted for age, AMH levels as a function of length of DHEA supplementation. FIG. 9 very clearly demonstrates a steady increase in AMH over time until 120 days after initiation of DHEA (p=0.002). Age (p=0.007) and length of DHEA supplementation (p=0.019) were independently associated with AMH levels. Younger women, under age 38 years, demonstrated higher AMH levels from baseline, and proportionally improved AMH levels over time after initiation of DHEA more than older women at, or above, 38 years.

Very similar results were obtained in longitudinal evaluation: Here, AMH levels improved from 0.22±0.22 ng/ml at baseline, before start of DHEA, to 0.35±0.03 ng/ml at highest measured peak, an almost 60 percent improvement in mean (p=0.0001).

Figure 10:
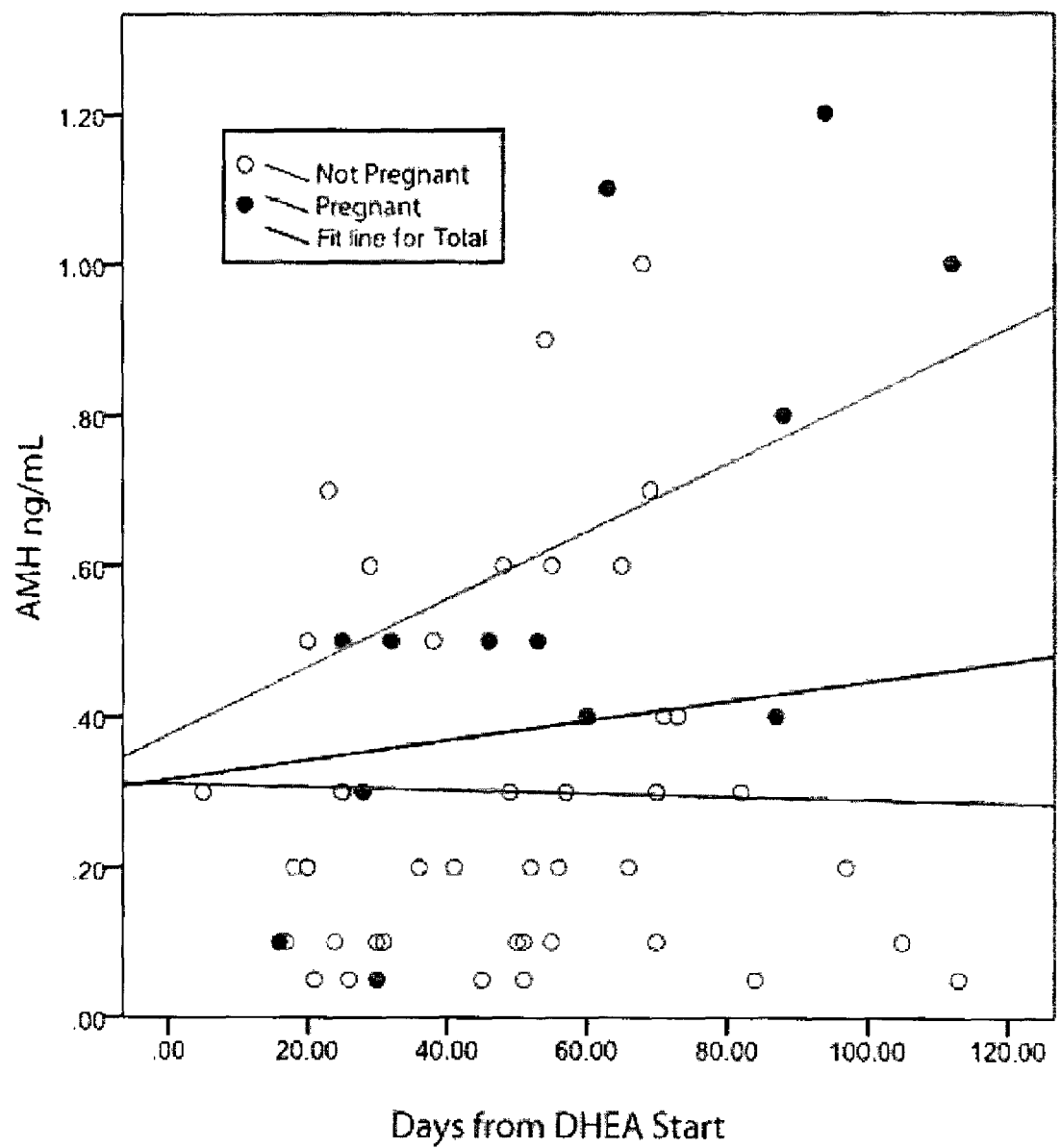
FIG. 10 is a graph showing levels over time from DHEA initiation in women who did and did not conceive.

Amongst 55 women who had undergone IVF, by time of analysis, 13 (23.64%) conceived a clinical pregnancy. FIG. 10 demonstrates a comparison of AMH levels after DHEA supplementation in women who did and did not conceive. As the figure demonstrates, those who conceived demonstrated a significantly better AMH response, following DHEA supplementation, than unsuccessful patients, whose AMH response remained flat (interaction of pregnant versus non-pregnant, Wald Chi Square 11.6; df=1; p=0.001).

Discussion of Example 9

By assessing changes in AMH levels, this study for the first time presents objective evidence that DHEA supplementation positively affects diminished ovarian reserve. In concordance with our prior clinical observations, this DHEA effect is visible in younger and older ovaries (FIG. 9), though is more pronounced in younger women with POA.

This study also strongly suggests that observed improvements in OR after DHEA supplementation lead to better pregnancy rates. As Table 10 demonstrates, AMH and FSH levels in the here-utilized study population are highly confirmatory of a significant degree of DOR.

Indeed, over half of the here-investigated patients consulted with our center for the first time after receiving advice elsewhere to discontinue fertility attempts with autologous oocytes and proceed into egg donation.

That in such an adversely selected patient population approximately one in four women still conceived with use of autologous oocytes is, in itself, a remarkable accomplishment. It is, however, especially remarkable that, as FIG. 10 demonstrates, the ovarian response pattern to DHEA is so dramatically different between those women who ended up conceiving and those who did not. While those with future pregnancies demonstrated remarkable improvements in AMH levels, unsuccessful women demonstrated generally no response whatsoever to DHEA. They, thus, for practical purposes can be seen as a control group: where DHEA does not improve OR, as indicated by generally flat AMH levels, pregnancy is very unlikely.

While associations in non-randomized studies always have to be viewed with caution, here reported results appear convincing. First, the observed pregnancy rate corresponds well to previously published clinical observations at our center, following DHEA supplementation. Improved pregnancy rates following DHEA have since also been reported by investigators in Greece and Canada.

While we and others have in the past speculated about possible mechanisms, why DHEA would improve conception rates in women with DOR has remained unknown. We recently suggested that at least part of DHEA's effect may be a reduction in oocytes and embryo aneuploidy. This study, however, for the first time offers a more direct and clinically practical explanation for DHEA effects in women with DOR.

The concept of OR has been based on a presumed remaining follicular pool within ovaries. As this pool shrinks, OR, and with it female fecundity, decline. In the process, the size of immature follicular cohorts, recruited each month, also declines. As cohorts decline in size, smaller and smaller follicle numbers reach gonadotropin sensitivity—the last stage of follicular maturation. As a consequence, follicle numbers and oocytes yield in IVF decline with advancing female age, as does female fecundity in general.

In fertility practice follicle numbers and oocytes yield are considered ultimate measures of OR. Indeed, AMH is increasingly considered a better reflection of OR because it better predicts oocytes yield in IVF than FSH. AMH, a dimeric glycoprotein and a member of the transforming growth factor (TGF) superfamily, is exclusively produced by granulose cells of early developing follicles, from primary to antral follicle stages. AMH is, thus, reflective of small, preantral follicles but not of the later stage follicular pool, better represented by FSH levels. AMH appears to better reflect total quantity and, possibly, quality of the remaining follicular pool, and, therefore, to be a better marker of declining reproductive age, an observation which potentially explains how DHEA affects ovarian function.

By demonstrating improving AMH levels, this study suggests that in selected patients with DOR, DHEA progressively improves OR at follicular stages at which AMH is produced. This means that over time DHEA increases the pool of follicles up to pre-antral stage, in this study causing a steady improvement in AMH up to 120 days post DHEA initiation. In prior clinical studies, with longer follow up periods, we demonstrated that follicular numbers and oocytes yield increase up to approximately five months of DHEA supplementation, equal to the approximate time period from primordial stages to gonadotropin sensitivity.

Combined, these observations suggest two possible mechanisms by which DHEA exerts its effects, both reflective of impacts on the follicular maturation cycle and improvements in number of AMH producing follicles: DHEA either positively affects recruitment from the dormant follicular pool or it progressively reduces apoptosis of originally recruited follicles, which represents the primary process by which originally recruited follicles are eliminated during follicular maturation. Either way, progressively more preantral follicles accumulate, resulting in the here documented increase in AMH over time from initiation of DHEA supplementation.

The effect of DHEA on follicular recruitment has not been investigated. Androgens, in general, appear, however, capable of positively affecting follicular recruitment in the mouse.

Similarly, nothing is known about DHEA effects on apoptosis, and androgens, in general, have been reported to have both enhancing and suppressing effects on ovarian granulose cell apoptosis.

Our previously published clinical observations suggested that approximately two months of DHEA supplementation were required before statistically significant differences in outcomes could be observed. FIG. 10 suggests that beneficial effects of DHEA may already become apparent even earlier, and may be reflected in spontaneous pregnancies we and others have reported in a small number of prognostically highly unfavorable patients, preceding other therapeutic interventions.

While improving AMH levels in women with DOR appear closely associated with pregnancy success, AMH is, unfortunately, not sensitive enough to predict who will or will not conceive.

Pregnancies can even be established at undetectable AMH levels. This means that AMH levels alone will not allow discrimination between who does and does not deserve further infertility treatments.

As this study, however, demonstrates, AMH offers objective evidence for the therapeutic efficacy of DHEA in women with DOR, and especially under age 38 years. Moreover, a good AMH response to DHEA supplementation clearly discriminates between good and poor prognosis patients in regards to pregnancy success. This information alone will greatly improve patient counseling in women with significant DOR. We are currently investigating other markers of OR in attempts to even better predict success of DHEA supplementation and, thus, avoid such treatment in women who will not improve pregnancy chances in response to DHEA supplementation.

EXAMPLE 10

AMH Levels

Introduction of Example 10

Functional ovarian reserve (OR) declines with advancing female age (Knauff et al. 2009); yet, ovarian function tests traditionally utilize cut-off values for normal ovarian function in age-independent ways. For example, with the most frequently utilized OR-test, follicle stimulating hormone (FSH), cut-off values of 10.0-12.0 mIU/mL have traditionally been considered the upper limit of normal (Barad et al. 2007).

More recently, anti-Müllerian hormone (AMH) has found increasing application in determining OR (Ebner et al. 2006; Fleming et al. 2006; Nelson et al. 2007; Broer et al. 2009; Carlsen et al. 2009; Knauff et al. 2009; Nelson et al. 2009). We demonstrated that, while AMH and FSH correlate (Singer et al. 2009), AMH is superior to FSH in predicting oocytes yields (i.e. OR) and IVF outcomes (Barad et al. 2009). Gnoth et al. suggested that a minimum level of 1.26 ng/mL denotes diminished ovarian reserve (DOR) in women of all ages (Gnoth et al. 2008).

We previously pointed out that, in determining OR, age-specific (as-) FSH levels are preferable to non-age-specific (nas-) cut-off values, discriminate between better and poorer oocyte yields in association with in vitro fertilization (IVF), and allow for a more accurate diagnosis of DOR, especially in younger women under age 38 years (Barad et al. 2007). In similar fashion, one can expect as-AMH levels to be superior to nas-cut-off levels. Such as-cut-offs have, however, so far not been defined.

This study, therefore, analyzed as-cut-offs in an infertility population of women and attempted to determine to what degree as-AMH levels could discriminate between women with better and poorer OR, based on oocytes yields in IVF.

Materials and Methods of Example 10

778 consecutive female patients in 2007 and 2008 represented an unselected initial study population. To define as-AMH levels based on 95% CI cut off values, women with obviously elevated baseline FSH above 12.0 mIU/ml were eliminated from establishing as-AMH cut off values, leaving 206 patients for statistical analysis. They were separated into four age categories: below 30 years, 31 to 35 years, 36 to 40 and 41 years and above.

Within each age group, as-AMH levels were determined, based on the 95% confidence intervals (CI) of the mean, using first AMH sampling results at the center.

Since 2007, our center assesses AMH routinely at time of a new patient's initial blood draw. A total of 288 amongst the original 778 women had reached IVF by time of data analysis. They were utilized to analyze oocytes yields in reference to the as-OR parameters AMH and FSH.

Patients sign at time of initial consultation an informed consent, which permits for use of data from their medical record for clinical research purposes, as long as the medical record remains confidential, and the identity of the patient remains protected. Such record-based studies are then only subject to an expedited review process by the Institutional Review Board.

Race/ethnicity of patients are determined at initial consultation. Clinical circumstances and infertility diagnoses are periodically reevaluated as new clinical and laboratory data are obtained. Selected clinical patient data are, aside from each patient's medical record, also maintained in the center's electronic research data base, which is written in Microsoft Access, and is only accessible to authorized clinical investigators.

Normal as-AMH levels were defined as within the 95% CI of each age group. DOR was diagnosed if AMH levels were under the lower cut off for an age group's normal range. A possible diagnosis of polycystic ovarian syndrome (PCOS), and, therefore, of potential OHSS risk, was considered at as-AMH levels above the upper 95% CI for an age group.

The 288 women who by time of data analysis had reached a first in vitro fertilization IVF) cycle, were separately analyzed from the whole study group Like the complete study population, they were divided into the same age categories. Oocyte yields were then assessed within each age category, based on whether a patient demonstrated normal, low or high as-AMH.

As previously reported (Barad et al. 2009), a commercially available enzyme-linked immunoabsorbent assay (ELISA) is utilized to assess AMH. In brief, this is the DSL-10-14400 active Müllerian Inhibiting Substance/Anti-Müllerian Hormone (MIS/AMH) enzyme-linked immunoabsorbent (ELISA) (Diagnostic Systems Laboratories, Inc. Webster, Tex. 77598-4217, USA), an enzymatically amplified two-site immunoassay, which does not cross-react with other members of the TGF-β superfamily, including TGF-β1, BMP4 and ACT (Kevenaar et al. 2006). Theoretical sensitivity, or minimum detection limit, calculated by interpolation of mean plus two standard deviations of eight replicates of the 0 ng/mL MIS/AMH Standard, was 0.006 ng/mL. Intra-assay coefficient of variation for an overall average AMH concentration was <10 percent (Kevenaar et al. 2006). Results are presented in ng/mL, with a conversion factor×7.14 to pmol/L (Ebner et al. 2006).

In addition to AMH, OR was assessed via cycle day 2/3 FSH and estradiol levels, obtained in the cycle preceding IVF. Both hormones were assessed utilizing an automated chemiluminescence system (ACS: 180, Bayer Health Care, Tarrytown, N.Y.)

Initial ovarian stimulation protocols of patients are principally determined by their age, with secondary modifications made based on ovarian function assessments. With presumed normal ovarian reserve, women up to age 38 years are routinely stimulated in a long agonist protocol with 150 to 300 IU of human menopausal gonadotropin (hMG) daily. Above age 38, or if women are considered to suffer from DOR at even younger ages, routine stimulation calls for a microdose agonist protocol with at least 450 IU of gonadotropins daily, most given as follicle stimulating hormone (FSH), but 150 IU given as hMG, as previously reported (Karande et al. 1999).

IVF cycles are conducted in routine fashion. In brief, human chorionic gonadotropin (hCG) is administered after leading follicles exceed average diameters of 18 mm, and oocyte retrievals under ultrasound control take place approximately 34 hours after hCG. Retrieved follicular fluids are immediately transferred to the embryology laboratory, where oocyte yields are determined.

All data are expressed as mean±standard deviation (SD). Variables that did not conform to normality were log converted and back-transformed. They are presented as means and 95% CI of the mean. A p-value<0.05 was considered statistically significant.

Differences between normally distributed variables were tested with analysis of variance or co-variance. Differences between groups of variables, not conforming to normality, were tested with the Mann-Whitney test and p<0.05 was, here too, considered statistically significant. All analyses were carried out utilizing SPSS software for Windows, version 17.0, 2005 (SPSS Inc. Chicago, Ill.)

Results of Example 10

FIG. 11 is a table showing patient characteristics. IVF patients did not differ statistically in any parameter from the whole study group. CI is confidence interval; DOR is diminished ovarian reserve; POA is premature ovarian aging.

FIG. 11 summarizes patient characteristics separately for the total, initially presenting patient population of 778 women, and for 288 patients who reached IVF. Amongst the total population, 67.1% were Caucasian, 13.9% African and 19.1% Asian and the racial distribution amongst IVF patients was almost identical.

Primary infertility diagnoses were also very similar in both patient groups. In the total population this included the following: DOR and/or premature ovarian aging (POA, 51.4%), tubal infertility (20.2%), male factor (13.9%) and "other" (6.6%). IVF patients demonstrated an almost identical distribution (FIG. 11).

FIG. 14A is a graph showing as-AMH levels (Anti Mullerian Hormone ng/ml). The figure demonstrates means and 95% CI for AMH (upper panel) relating to female age. FIG. 14B is a graph showing as-FSH levels (Follicle Stimulating Hormone mlU/ml). The figure demonstrates means and 95% CI FSH (lower panel) relating to female age. In accordance with better specificity of as-AMH than as-FSH, reported here (see discussion) and elsewhere (Barad et al., 2009), as-ranges for AMH are narrower than those of as-FSH.

FIG. 14 demonstrates that both, AMH (upper panel) and FSH (lower panel), statistically to a significant degree change with age (p<0.001, each). The figure, however, also demonstrates that as-hormone ranges are narrower with AMH than FSH. Moreover, with both hormones the most narrow range and, therefore, highest specificity is reached at approximately age 35 years, with as-ranges from that point on expanding with younger as well as older ages.

FIG. 12 is a table showing hormone levels among 206 patients with normal baseline FSH. AMH levels decrease significantly between age categories (p<0.001), while FSH increases (p=p<0.001) and estradiol remains unchanged. FIG. 12 summarizes lower and upper cut off values at various ages.

Figure 15:
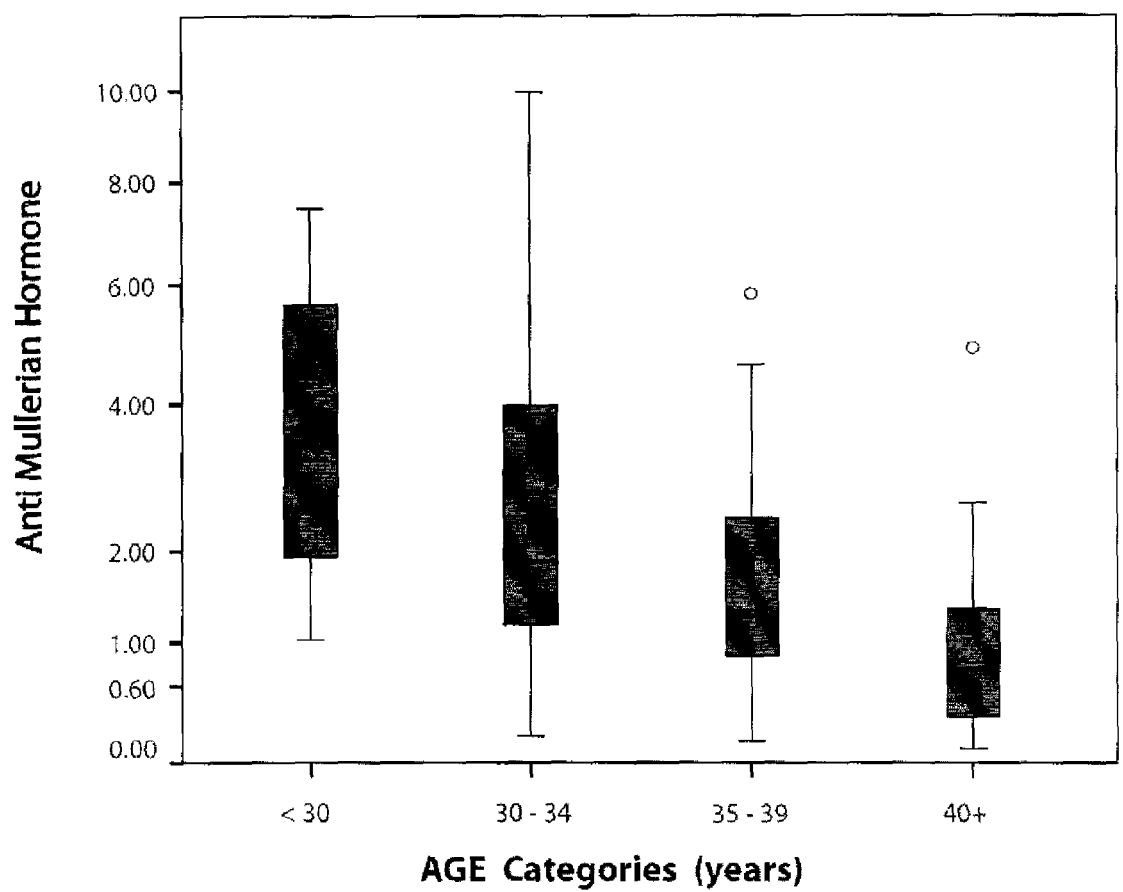
FIG. 15 is a graph showing the definition of as-AMH (Anti Mullerian Hormone).

FIG. 15 is a table showing the definition of as-AMH (Anti Mullerian Hormone). The figure demonstrated means and 95% CI of AMH for 4 age groups. AMH levels declined significantly with age (p<0.001).

When age categories are set for AMH (FIG. 15), statistically robust cut-off values, representing the 95% CI for any given age group, can be established. FIG. 12 offers details: Means of as-AMH, as well as upper and lower cut offs, decrease significantly from age-bin to age-bin as women age. Mean levels decline from 3.8 ng/mL below age 30, to 2.0 ng/mL at age 30 to 34, to 0.9 ng/mL at 35 to 40 and to 0.4 ng/mL at age 40 years.

As FIG. 12 demonstrates, normal as-AMH ranges are under age 30 3.1 to 4.6 ng/mL, at ages 31 to 35 years 1.5 to 2.7 ng/mL, between ages 36 and 40 above 0.8 to 1.1 ng/mL and from age 41 on 0.2 to 1.0 ng/mL.

Based on these criteria, 138/287 (48.1%) women, who reached IVF (one patient had no recorded pre-IVF AMH value), demonstrated abnormally low, 57 (19.9%) normal and 92 (32.1%) abnormally high, as-AMH levels.

Figure 16A:
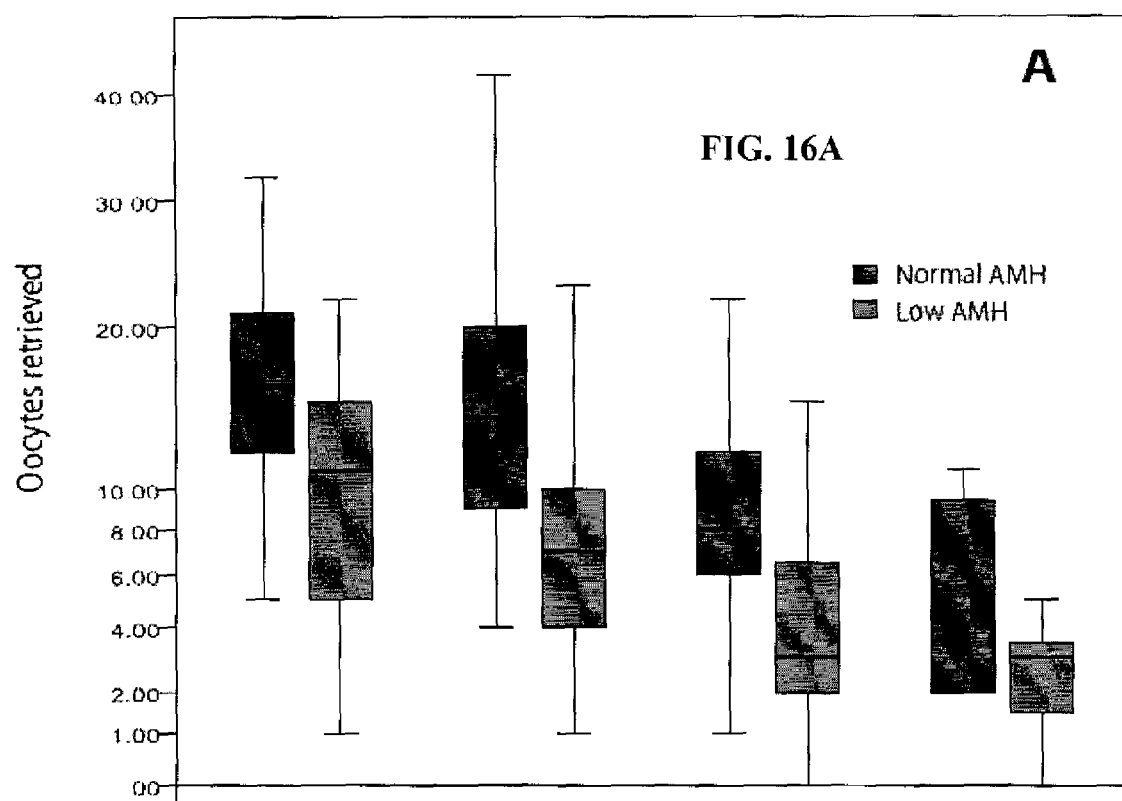
FIG. 16A is a graph showing oocyte yields at different ages and AMH levels.
Figure 16B:
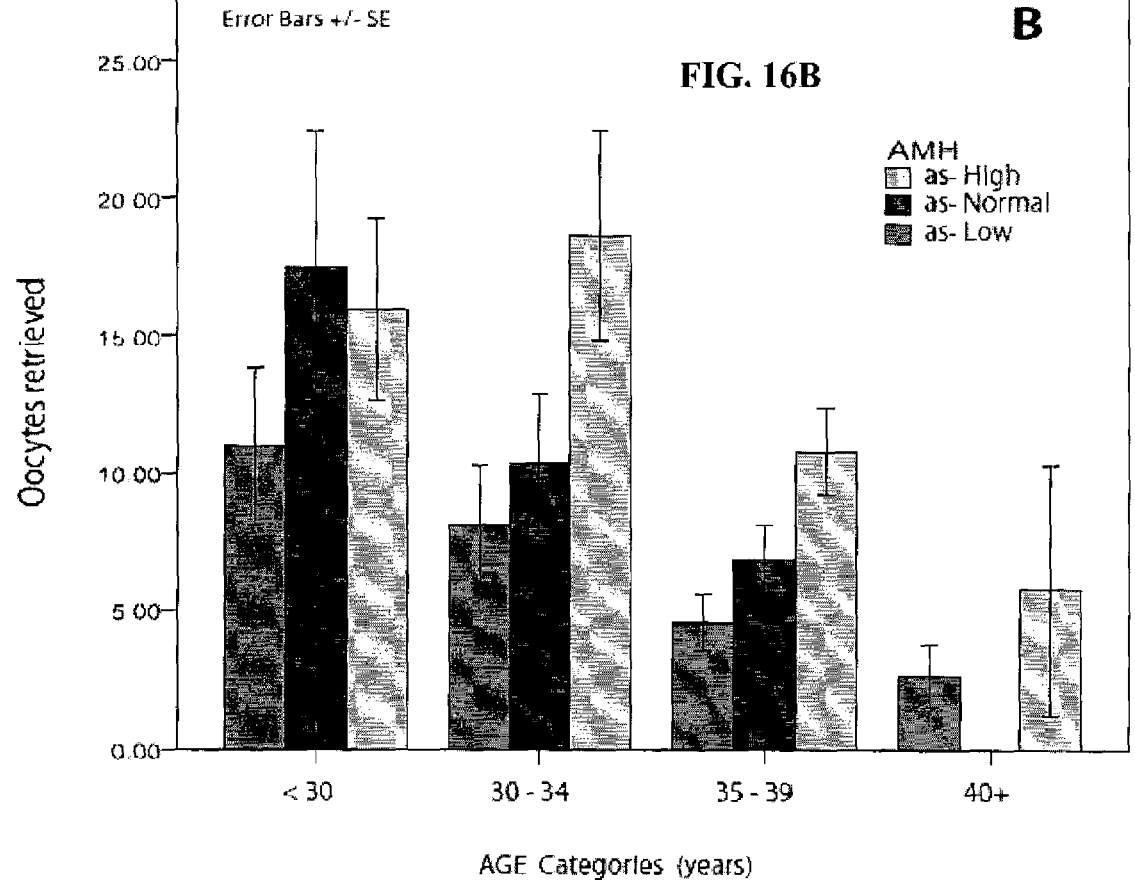
FIG. 16B is a graph showing oocyte yields at different ages and AMH levels.

FIG. 16A is a graph showing oocyte yields at different ages and AMH levels. Upper panel [A] demonstrates oocytes yields with normal and high (red) and abnormally low (blue) AMH. The figure suggests that oocyte yield among women with normal and high as-AMH decline only mildly up to age 30, when their decline accelerates. In contrast women with abnormally low as-AMH appear to decline steadily till age 39, when the decline appears to flatten. Differences were, however, not statistically significant. FIG. 16B is a graph showing oocyte yields at different ages and AMH levels The lower panel [B] defines oocytes yields in each age-group based on abnormally low (blue), normal (red) and abnormally high (beige) as-AMH levels. Normal was defined as the 95% CI for a given age-group. The patient group above age 40 years is too small to offer statistically valid conclusions. Table 13 offers further statistical details.

FIG. 13 is a table showing oocyte yields among patients reaching IVF. Superscripts denote significant difference (p<0.05) from designated column within age categories: [a] denotes low as-AMH; [b] normal as-AMH; [c] high as-AMH; Total ooytes yields in women with as-normal and high AMH were significantly higher than those in women as-low AMH (F=78.9, df=1; p<0.00001).

FIG. 16 and FIG. 13 summarize oocytes yields in the four age categories. Oocyte numbers declined overall with advancing female age (p<0.001).

FIG. 16, however, defines the subtleties of this decline after adjustment for age: FIG. 16A (upper panel) demonstrates oocytes yields in the four age categories, depending on low (in blue) or combined normal and abnormally high (in red) as-AMH. As the figure demonstrates, oocyte yields with abnormally low as-AMH were in all age-categories till age 40 significantly lower than with normal (and high) AMH (p<0.001; for further statistical detail, see FIG. 13). Indeed, oocytes yields, overall, were 5.4-times (95% CI 4.1-6.8) higher in women with normal and abnormally high as-AMH in comparison to those with subnormal levels.

FIG. 16B further defines these data because the figure separates oocytes yield in each age category by abnormally low (blue), normal (red) and abnormally high (beige) as-AMH: At youngest ages (<30 years) as-AMH statistically differentiates low yields with abnormally low AMH from very similar higher yields with normal and even abnormally high as-AMH. In this age group excessively high AMH, however, does not define a high risk group for excessively high oocytes yields since yields do not differ between normal and high as-AMH. FIG. 13 summarizes the statistical details.

This picture, however, changes in the next two age-categories, where abnormally low, normal and abnormally high as-AMH directly correlates with oocytes yields (FIG. 13). Above age 40 years, small patient numbers should be cause for cautious interpretations. Abnormally low as-AMH still appears to differentiate oocytes yields from women with abnormally high as-AMH but, considering low overall oocytes yields in this age category, differences are no longer pronounced. The most interesting observation in this age group may, indeed, be that women with normal as-AMH levels appear rare. All here investigated patients in this age group were either abnormally low or abnormally high in their respective AMH (FIG. 16).

FIG. 13 demonstrates that, among 288 women who reached oocytes retrieval, those with low as-AMH (n=138) yielded at all ages fewer oocytes than women with normal as-AMH (n=57) (p<0.05). Above age 30 years, those with abnormally high as-AMH (n=92) demonstrated significantly higher oocytes yields (p<0.05). Women with abnormally low as-AMH very clearly differentiated themselves in oocytes numbers from all other patients (normal and high as-AMH combined) (F=78.9, df=1; p<0.00001).

Discussion of Example 10

Challenges in assessing OR correctly, and limitations of currently available methodologies have recently been subject to a number of insightful publications (Fleming et al. 2006; Sun et al. 2008; Broer et al. 2009; Knauff et al. 2009). Unanimity appears to evolve that AMH in many ways may represent a more specific marker of DOR than historically utilized FSH (Hazout et al., 2004; Ebner et al., 2006; Barad et al., 2009).

However, with few exceptions (Ebner et al. 2006; Gnoth et al. 2008; Barad, et al. 2009; Singer et al. 2009), the literature so far does not offer cut off values for AMH that may delineate between normal and abnormal OR. Moreover, the literature, with one exception (Barad et al. 2009), also so far does not comment on potential differences in utility of AMH at different female ages, as observed for FSH (Abdalla et al. 2004; Toner 2004).

Based on FSH data, we in 2007 suggested that as-ovarian reserve assessments may be superior to nas-testing in predicting DOR and production of lower oocytes yields in association with IVF (Barad et al. 2007). Sun and associates, who pointed out the importance of differentiating between age-dependent (physiologic) and non-age-dependent (premature) ovarian aging, recently also suggested a similar concept (Sun et al. 2008). Considering such evolving concepts, it appeared important to investigate whether as-AMH levels, like as-FSH, may offer improved specificity in detecting DOR over nas-AMH testing. This study did that and, as previously reported for FSH, AMH-data strongly reemphasize that, judged by oocytes yields in IVF, as-ovarian function tests appear superior to nas-testing.

The study population to a large degree represented infertility patients with significant DOR (FIG. 11). To avoid extremes, we, however, had eliminated DOR patients with FSH elevations (>12 mIU/ml) in establishing as-95% CIs. The effectiveness of this approach is well documented by the fact that the final study populations still demonstrated the well described declines in AMH (and rises in FSH) with advancing female age ((Singer et al. 2009, and FIG. 1).

This study, however, offers important additional insights: It demonstrates for the first time that the range of as-AMH is at all ages narrower than that of as-FSH (FIG. 14). Since narrower testing ranges reflect more specificity, it is not surprising that AMH has been found to be more specific in reflecting OR than FSH (Barad, et al. 2009).

The figure also demonstrates, however, that both, AMH and FSH, demonstrate the narrowest ranges of as-levels at approximately age 35 years. This observation would suggest that at this age both of these OR parameters are probably at their best (i.e., demonstrate highest specificity) in reflecting ovarian function. Below and above that age, normal ranges widen and, hormone levels, therefore, likely, become less specific. This, of course, should not surprise: Abnormally high FSH levels at younger ages have been reported as less predictable of poor treatment outcomes (Abdalla and Thum 2004; Toner 2004), and we previously reported that, though superior to FSH, AMH looses specificity at more advanced female ages (Barad et al. 2009). OR evaluations by FSH and AMH, and even their as-values, therefore, have to be viewed differently at different ages.

This study, thus, sheds further light on the value of AMH testing at different ages. As FIG. 16B well demonstrates, even as-AMH, while still superior to nas-AMH, appears to offer its best diagnostic specificity only at ages 30 to 39 years, correlating well to the narrowest range of as-AMH at approximately age 35 (FIG. 1). Within that age-range, as-AMH discriminates well in regards to oocytes yields at both extremes of AMH: abnormally low levels correlate statistically with abnormally low oocytes yields, while abnormally high AMH is predictive of high oocyte yields.

While abnormally low oocytes yield is often defined as four or less retrieved oocytes, such an age-independent definition does not make physiological sense since expected oocytes yields, of course, are much higher at younger than older ages (Singer et al. 2009). In practical terms this means that four or less oocytes will always represent a low count in younger women but may represent an excellent retrieval result at older age. In the same way, seven or eight oocytes, clearly above this widely utilized cut off value, may still represent a low yield in a 22-year old. The relativity of oocytes yield, based on female age, therefore, needs to be considered when results of this study are assessed.

At younger ages (<30 years), as-AMH still discriminates risk for low oocyte yields, but appears insufficiently specific to discriminate high oocytes numbers from normal yields. Because of small patient numbers, this study is limited in its ability to assess the value of as-AMH in women above age 40 years. The most interesting finding in this age group may, however, be the observation that, at advanced ages, most women represent two specific phenotypes: they either have low or high as-AMH, with few, if any patients, in between. While the small sample size of patients in this age group warrants caution in interpreting these data, this finding is potentially interesting since it correlates well with recent data, developed in DOR patients under dehydroepiandrosterone (DHEA) supplementation. They, largely, either did, or did not, improve AMH levels with DHEA, and occurrence of pregnancy was almost exclusively linked to improvements of AMH (Gleicher et al. 2009).

Combined, these data may suggest that, despite declining specificity with advancing female age, AMH may find a place in defining who, amongst older women above age 40, may benefit from infertility treatments.

The accurate diagnosis of DOR, therefore, appears important at all ages. This may seem counterintuitive to current clinical practice, which largely assumes that younger women, even if afflicted by DOR, still possess adequate OR to conceive (Gleicher et al. 2006) and that, therefore, a timely and more accurate diagnosis of DOR in young women may be less of a priority than in older women.

While this study does not contradict this argument, accurate and timely diagnosis in young women may be even more important than in older patients since DOR is less clinically obvious at younger ages, frequently unsuspected and overlooked and often leads to an inappropriate diagnosis of so-called unexplained infertility (Gleicher et al. 2006; Barad et al. 2007). Younger women, therefore, may actually be the best targets for as-AMH testing. Once suspected of DOR, they then can be followed closely, and consider time adjustments to family building efforts or fertility preserving treatments.

Comparing here reported differences in as- and nas-AMH to our previously published FSH data (Barad et al. 2007), the discriminatory abilities of as-AMH in predicting oocytes yields, and therefore insipient DOR, appear superior at all ages. These findings, of course, correlate well with the better specificity of nas-AMH over nas-FSH (Barad et al. 2009). Whether combining as-FSH and as-AMH further improves assessments of DOR and expected oocytes yields is currently under investigation.

These conclusions also correlate well with previously published work by Austrian colleagues: Ebner and associates not only suggested that AMH appears superior to FSH in predicting oocytes numbers and their quality, but actually defined a nas-AMH range for maximal oocytes quality between 1.7 and 4.5 ng/mL (Ebner et al. 2006). This range, of course, almost perfectly relates to the normal as-AMH range, defined in this study for women up to age 34 years (FIG. 12). It, now, would be interesting to determine whether this ideal AMH range in regards to egg quality also changes with advancing female age or whether the obviously superior quality of young age is not recoverable at later ages.

Historically, AMH has been primarily utilized to rule out the presence of DOR. AMH, however, is also potentially useful at the other end of the OR spectrum, when a diagnosis of PCOS is contemplated (Nelson et al. 2007; Carlsen et al. 2009; Nelson et al. 2009). AMH cut off values have here, however, so far also not been defined well, and where attempts at definition were made, nas-testing was utilized (Nelson et al. 2009).

While this study does not define diagnostic as-AMH levels for PCOS, it very clearly demonstrates that the upper 95% CI of as-AMH, at least in women at ages 30-39 years, discriminates between normal and abnormally high oocytes yields with IVF (FIG. 13 and FIG. 16B).

Nelson et al suggested that already a nas-AMH of above 15 pmol/L (2.1 ng/mL) denotes risk for ovarian hyperstimulation (Nelson et al. 2009). Such an AMH level, on as-basis, is below the lower cut off point in women under age 30 years and in the middle of the normal range of women between ages 30 to 34 years (FIG. 12). It, therefore, would include a majority of young women with normal OR, not appear specific enough to identify patients at risk for ovarian hyperstimulation and clinically be impractical as a screening tool and rational for changes in stimulation protocol, as suggested by these authors (Nelson et al. 2009).

In the here reported study 4.6 ng/mL represents the upper limit of normal in the youngest, and therefore highest risk, group for ovarian hyperstimulation. While none of the women did develop significant clinical hyperstimulation, some produced excessively high oocytes yields (FIG. 13). More importantly, however, in all age groups above age 30 years, the upper 95% CI clearly did define a patient population that produces significantly more oocytes than women in normal as-AMH range.

This study, therefore, suggests that as-AMH at all ages allows for discrimination of oocytes yields, but does so differently at different female ages. Whether the here utilized methodology of defining normal ranges by as-95% CIs represents the best methodology, remains to be seen. The here presented data, however, suggest that as-AMH testing offers clear advantages over nas-testing and that, whatever ultimate cut off values shall be chosen to define risk towards abnormal ovarian responses, they should be age-specific.

By also defining risk towards high oocytes yields, as-AMH thus demonstrates yet another distinct advantage over as-FSH, which has only predictive value for abnormally low oocytes yields (Barad et al. 2007). The prevention of OHS S has, to a degree, remained elusive (Nelson et al. 2007), and is especially important in younger women, where risks are the highest since oocytes production is the largest (Engmann et al. 2008).

Here presented as-AMH ranges, however, need to be viewed with caution: As previously demonstrated for FSH, as-hormone levels will be dependent on study populations (Barad et al. 2007). Since the 95% CI for age will vary dependent on the percentage of women with DOR in each age group, we reported, as one would suspect, different as-FSH levels between IVF centers, dependent on their respective patient populations. More favorably selected patients in one center, therefore, will demonstrate lower FSH and higher AMH cut offs than less favorable patients at another center. In considering the design of this study, we built on above noted experience and removed from considerations women with very obvious DOR, defined by FSH levels above 12.0 mIU/mL.

Considering the adverse patient selection and high prevalence of premature DOR at our center (FIG. 11, Barad et al., 2007), our patient population may, nevertheless, still be more affected by DOR than patients at many other IVF centers. Extrapolating from our previously published FSH data (Barad et al. 2007), it, therefore, seems likely that here reported as-AMH cut off levels will be conservative for a majority of infertility centers. Fertility centers with less adversely selected patients may, therefore, have to utilize slightly higher as-AMH cut offs at all ages. Preferably, of course, fertility centers should establish center-specific as-cut off values until, ideally, universal cut off values have been reported for normal, fertile populations, which would be applicable to all women.

Conclusion of Example 10

This study once more demonstrates the advantages of as-OR testing in comparison to currently still widely practiced nas-testing. By having demonstrated advantages to as-FSH, and now as-AMH, testing over traditional nas-testing, it seems increasingly likely that as-testing is, in general, superior to nas-testing when it comes to OR assessments.

Utilizing multiple ovarian reserve parameter, Verhagen and associates, based on a meta-analysis of published studies, recently argued that the use of more than one OR test can currently not be supported. After reviewing multivariate models for prediction of OR and occurrence of pregnancy with IVF, they concluded that predictive values of various models, utilizing different tests, did not vary significantly from the accuracy of antral follicle counts as a single test (Verhagen et al. 2008).

While the here presented data cannot address the benefits of multiple OR tests over the utilization of only single tests, it is important to note that Verhagen's meta-analysis involved only nas-testing. It seems possible, and maybe even likely, that as-testing of OR may give different results.

Like Verhagen et al, we recently compared predictive values for OR and pregnancy, based on receiver operating characteristic (ROC) curves, and demonstrated a significant advantage of AMH over FSH in predicting both outcomes (Barad et al. 2009). Those comparisons, like those of the Dutch investigators, were based on nas-testing. By now having demonstrated significant advantages of as-over nas-testing for FSH and AMH, it seems increasingly likely that only as-use of all OR tests will further improve sensitivity and specificity of such testing. This means that, whether OR testing is performed using FSH, AMH, antral follicle counts or other testing procedures, all should utilize as-, rather than nas-cut off values.

as-OR tests appear to offer distinct benefits at all ages and may be especially beneficial for younger women in whom a diagnosis of DOR is rarely suspected and, therefore, often overlooked, and who are at highest risk for OHSS.

While the foregoing written description of the invention enables one of ordinary skill to make and use what is considered presently to be the best mode thereof, those of ordinary skill will understand and appreciate the existence of variations, combinations, and equivalents of the specific exemplary embodiments thereof. The invention is therefore to be limited not by the exemplary embodiments herein, but by all embodiments within the scope and spirit of the appended claims.

What is claimed is:

1. A method of using dehydroepiandrosterone (DHEA) to treat a human female with diminished ovarian reserve, said method comprising:
measuring a baseline follicle stimulating hormone (FSH) level of said human female to determine whether the female has ovarian failure; and
when said baseline FSH level is below about 40.0 mIU/ml indicating the female does not have ovarian failure, then administering about 75 milligrams of DHEA per day to said female for at least four months, without requiring concurrent administration of gonadotropin, to treat ovarian follicles in at least one ovary of said female to improve human folliculogenesis during the at least four months.

2. A method according to claim 1, wherein between about 15 mg and about 40 mg of said dehydroepiandrosterone is administered three times a day to the female.

3. A method according to claim 1, wherein said dehydroepiandrosterone is orally administered.

4. A method according to claim 1 wherein said method improves egg quality and embryo quantity, decreases time to pregnancy, improves pregnancy rates, decreases miscarriage rates and improves ovarian environment.

5. A method of treating a human female with diminished ovarian reserve, said method comprising:
   administering about 75 milligrams of dehydroepiandrosterone (DHEA) per day to said female for at least four months, without requiring concurrent administration of gonadotropin, to expose ovarian follicles of said female to DHEA to improve human folliculogenesis during the at least four months;
   evaluating whether said female is pregnant;
   when said female is not pregnant, continue administering about 75 milligrams per day of DHEA, without requiring concurrent administration of gonadotropin, to said female until said female becomes pregnant;
   when said female is pregnant, stop administering DHEA to said female.

6. The method of claim 1 wherein administering the DHEA comprises affecting ovarian follicles of the female, said follicles not yet being sensitive to gonadotropin.

7. The method of claim 5 wherein administering the DHEA comprises affecting ovarian follicles of the female, said follicles not yet being sensitive to gonadotropin.

* * * * *